United States Patent [19]

MacLeay et al.

[11] Patent Number: 5,338,853

[45] Date of Patent: Aug. 16, 1994

[54] DERIVATIVES OF N-HALS-SUBSTITUTED AMIC ACID HYDRAZIDES

[75] Inventors: Ronald E. MacLeay, Williamsville; Harold C. Lange, Grand Island, both of N.Y.

[73] Assignee: Elf Atochem North America, Inc., Philadelphia, Pa.

[21] Appl. No.: 793,741

[22] Filed: Nov. 18, 1991

Related U.S. Application Data

[63] Continuation-in-part of Ser. No. 455,219, Dec. 22, 1989, abandoned.

[51] Int. Cl.$^5$ ............... C08K 5/3432; C07D 211/56; C07D 211/30
[52] U.S. Cl. ............................. 546/224; 546/14; 546/187; 546/190; 546/208; 546/244; 524/99; 524/102
[58] Field of Search ............... 546/224, 14, 187, 190, 546/208, 244; 524/99, 102

[56] References Cited

U.S. PATENT DOCUMENTS

| | | | |
|---|---|---|---|
| 3,116,305 | 12/1963 | Morris | 524/291 |
| 3,330,859 | 7/1967 | Dexter et al. | 524/291 |
| 4,145,512 | 3/1979 | Uhrhan et al. | 546/244 |
| 4,178,279 | 12/1979 | Uhrhan et al. | 528/60 |
| 4,309,546 | 1/1982 | Karrer | 546/187 |
| 4,336,183 | 6/1982 | Nakahara et al. | 524/95 |
| 4,824,884 | 4/1989 | MacLeay et al. | 524/99 |
| 4,876,299 | 10/1989 | Avár | 546/224 |
| 4,916,175 | 4/1990 | Avár | 546/224 |
| 4,983,738 | 1/1991 | Kazmierczak et al. | 546/224 |
| 5,101,033 | 3/1992 | Kazmierczak et al. | 546/224 |
| 5,106,983 | 4/1992 | Reiff et al. | 546/224 |

FOREIGN PATENT DOCUMENTS

| | | |
|---|---|---|
| 1190038 | 7/1985 | Canada . |
| 0303279 | 2/1989 | European Pat. Off. . |
| 0366057 | 5/1990 | European Pat. Off. . |
| 8900604 | 8/1990 | PCT Int'l Appl. . |

OTHER PUBLICATIONS

Communication dated May 3, 1991 from EPO enc. Search Report.

*Primary Examiner*—Kriellion S. Morgan
*Attorney, Agent, or Firm*—Stanley A. Marcus; Royal E. Bright

[57] ABSTRACT

N-(2,2,6,6-tetraalkyl-4-piperidinyl)amic acid hydrazides contain a light stabilizing group, a heat stabilizing group and an amic acid hydrazide functionality in the same molecule. The amic acid hydrazide functionality in the compounds enhances the photooxidative stabilizing properties of the hindered amine groups and contributes thermal and oxidative stabilizing and metal complexing properties to the compounds. The novel compounds are excellent light stabilizers for polyolefins, have low volatility and are not readily lost from polymeric systems via volatilization, migration or extraction.

25 Claims, No Drawings

DERIVATIVES OF N-HALS-SUBSTITUTED AMIC ACID HYDRAZIDES

CROSS-REFERENCE TO RELATED APPLICATION

This application is a continuation-in-part of copending U.S. patent application Ser. No. 07/455,219, filed Feb. 22, 1989 now abandoned.

BACKGROUND OF THE INVENTION

1. Field of the Invention

This invention relates to novel derivatives of N-(2,2,6,6-tetraalkyl-4-piperidinyl)amic acid hydrazides. These compounds are very efficient in the stabilization of polymeric systems which are subject to degradation upon exposure to heat and/or light.

Particularly, this invention is related to acyl, carbamoyl, thiocarbamoyl, alkoxycarbonyl, aryloxycarbonyl, aralkoxycarbonyl, cycloalkoxycarbonyl, aliphatic, alicyclic, araliphatic, aryl, 2-hydroxyalkyl, 2-hydroxycycloalkyl and hydrazone derivatives of N-(2,2,6,6-tetraalkyl-4-piperidinyl)amic acid hydrazides.

2. Description of the Prior Art

Derivatives of hindered amine light stabilizing-substituted hydrazides (HALS-substituted hydrazides) are disclosed in U.S. Pat. Nos. 4,145,512 and 4,178,279. These patents teach reacting hindered amine light stabilizers (HALS) containing carboxylic acid hydrazide groups with isocyanate groups of polyisocyanates or isocyanate prepolymers to obtain light stabilized polyurethanes. However, the HALS-hydrazides employed were not HALS-substituted amic acid hydrazides and therefore do not have the enhanced stabilizing effect of the novel derivatives of the present invention.

U.S. Pat. No. 4,336,183 discloses various HALS spiro compounds containing a hydrazide functionality. It also discloses various acyl derivatives of these hydrazides. However, none of the hydrazides are N-HALS-substituted amic acid hydrazides and consequently the derivatives do not fall under the scope of the present invention.

U.S. Pat. No. 4,983,738, assigned to the assignee of the present invention, disclose N-(2,2,6,6-tetraalkyl-4-piperidinyl)amic acid hydrazides from which the compounds of the present invention may be prepared. These compounds are efficient light stabilizers for polymeric systems; however, the disclosed compounds have some volatility limitations and can be extracted out of the polymers to some degree by water or aqueous solutions.

U.S. Pat. No. 4,824,884, assigned to the assignee of the present invention, discloses cyclic anhydride derivatives of N-(2,2,6,6-tetraalkyl-4-piperidinyl)amic acid hydrazides. These compounds are also efficient heat and light stabilizers for polymeric systems but do not fall under the scope of this invention.

Prior to the present invention, the results obtained with the known hindered amine light stabilizers have not been satisfactory with all types of manufactured articles, due to certain deficiencies in stabilization, compatibility, volatility, exudability or economics. Therefore, further improvement in the field of hindered amine light stabilizers is still desirable. The novel compounds of this invention address these shortcomings.

DEFINITIONS

Throughout the disclosure, when referring to "2,2,6,6-tetraalkylpiperidines" or "2,2,6,6-tetraalkyl-4-piperidinyl groups", the piperidinyl groups optionally substituted in the 3 position of the piperidine group with lower alkyl groups of 1-4 carbons are also included, i.e., the structure having the formula:

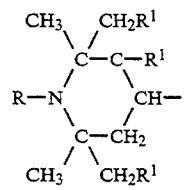

where R and $R^1$ are as defined hereinafter.

The term "acyl" refers to a radical generated from a carboxylic acid by the removal of the OH group to provide a free valence on the C(=O) group, for example, DC(=O)OH would become the DC(=O) substituent referred to generally as a D acyl group.

As used herein, the terms "polymer" or "polymeric composition(s)" include homopolymers or any type of copolymers.

Where any symbol appears more than once in a formula, its meaning in each instance is independent of one another.

SUMMARY OF THE INVENTION

This invention is directed to a derivative of N-(2,2,6,6-tetraalkyl-4-piperidinyl)amic acid hydrazide having the Formula I:

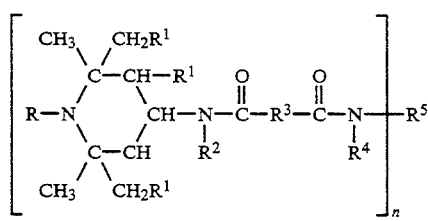

wherein

R is hydrogen, oxyl, hydroxy, substituted or unsubstituted aliphatic of 1–20 carbons, substituted or unsubstituted alicyclic of 5–12 carbons, substituted or unsubstituted araliphatic of 7–22 carbons, substituted or unsubstituted aliphatic acyl of 2–20 carbons, substituted or unsubstituted alicyclic acyl of 7–16 carbons, substituted or unsubstituted aryl acyl of 7–11 carbons, substituted or unsubstituted araliphatic acyl of 8–22 carbons, —C(=O)N($R^6$)($R^7$), —(C(=O))$_a$O—$R^8$, —(CH$_2$)$_a$C(=O)O—$R^9$ or —(CH$_2$—CH($R^1$)—O)$_b$—$R^{10}$;

n is 1 or 2;

a is 1 or 2;

b is an integer of 2–50;

$R^1$ is hydrogen or lower alkyl of 1–4 carbons;

$R^2$ is hydrogen, substituted or unsubstituted aliphatic of 1–20 carbons, substituted or unsubstituted alicyclic of 5–12 carbons, substituted or unsubstituted aryl of 6–14 carbons, substituted or unsubstituted araliphatic of 7–22 carbons, 2-cyanoethyl or a radical of the formula

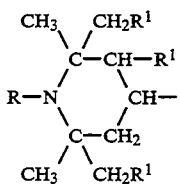

where

R and $R^1$ are as previously defined;

$R^3$ is a direct bond, a substituted or unsubstituted aliphatic diradical of 1-20 carbons, a substituted or unsubstituted aryl diradical of 6-12 carbons, a substituted or unsubstituted alicyclic diradical of 5-12 carbons or a substituted or unsubstituted araliphatic diradical of 7-22 carbons, where the diradical may contain 1-6 —O—, —S— or —NH— heteroatoms, with the proviso that multiple heteroatoms must be separated from each other and the diradical ends by at least one carbon atom;

$R^2$ and $R^3$ may be linked together to form a 5-membered lactam ring;

$R^4$ is hydrogen, substituted or unsubstituted aliphatic of 1-20 carbons, substituted or unsubstituted alicyclic of 5-12 carbons or substituted or unsubstituted araliphatic of 7-22 carbons;

when n is 1, $R^5$ is —N=C($R^{11}$)($R^{12}$), —N($R^{13}$)($R^{14}$) or —N($R^6$)—Q—$R^{15}$, when n is 2, $R^5$ is —N($R^6$)—Q—$R^{17}$—Q—N($R^6$)—;

Q is —C(=O)—, —C(=O)—O—, —C(=O)—N($R^4$)—, —C(=S)—N($R^4$)— or —S(=O)$_2$—, in which $R^4$ is as previously defined;

$R^6$ and $R^7$ are independently hydrogen, substituted or unsubstituted aliphatic of 1-20 carbons, substituted or unsubstituted alicyclic of 5-12 carbons, substituted or unsubstituted aryl of 6-14 carbons or substituted or unsubstituted araliphatic of 7-22 carbons;

$R^8$ is substituted or unsubstituted aliphatic of 1-20 carbons, substituted or unsubstituted alicyclic of 5-12 carbons, substituted or unsubstituted aryl of 6-14 carbons or substituted or unsubstituted araliphatic of 7-22 carbons;

$R^9$ is hydrogen, substituted or unsubstituted aliphatic of 1-20 carbons, substituted or unsubstituted alicyclic of 5-12 carbons, substituted or unsubstituted aryl of 6-14 carbons or substituted or unsubstituted araliphatic of 7-22 carbons;

$R^{10}$ is hydrogen or aliphatic of 1-4 carbons;

$R^{11}$ and $R^{12}$ are independently hydrogen, substituted or unsubstituted aliphatic of 1-20 carbons, substituted or unsubstituted alicyclic of 5-12 carbons, substituted or unsubstituted aryl of 6-14 carbons, substituted or unsubstituted araliphatic of 7-22 carbons;

$R^{11}$ and $R^{12}$ may be linked together to form a substituted or unsubstituted alicyclic ring of 5-12 carbons or may be linked together through an —O—, —S— or —NH— heteroatom to form a heterocyclic ring of 5-12 atoms wherein the —NH— may be substituted by lower alkyl of 1-4 carbons;

$R^{13}$ is hydrogen, substituted or unsubstitued aliphatic of 1-20 carbons, substituted or unsubstituted alicyclic of 5-12 carbons, substituted or unsubstituted araliphatic of 7-22 carbons or substituted or unsubstituted aryl of 6-14 carbons, where the $R^{13}$ substituents are chloro, bromo, cyano, hydroxy, epoxy, alkyl of 1-20 carbons, cycloalkyl of 5-12 carbons, aryl of 6-14 carbons, aralkyl of 7-22 carbons, alkoxy of 1-20 carbons, cycloalkoxy of 5-12 carbons, aryloxy of 6-14 carbons, aralkoxy of 7-15 carbons, aliphatic acyloxy of 2-20 carbons, alicyclic acyloxy of 6-13 carbons, aryl acyloxy of 7-15 carbons, alkylthio of 1-12 carbons, trialkoxysilyl of 3-12 carbons or araliphatic acyloxy of 8-16 carbons, wherein any alkyl or cycloalkyl substituent group may contain isolated double bonds;

$R^{14}$ is substituted or unsubstitued aliphatic of 1-20 carbons, substituted or unsubstituted alicyclic of 5-12 carbons, substituted or unsubstituted araliphatic of 7-22 carbons or substituted or unsubstituted aryl of 6-14 carbons, where the $R^{14}$ substituents are chloro, bromo, cyano, hydroxy, epoxy, alkyl of 1-20 carbons, cycloalkyl of 5-12 carbons, aryl of 6-14 carbons, aralkyl of 7-22 carbons, alkoxy of 1-20 carbons, cycloalkoxy of 5-12 carbons, aryloxy of 6-14 carbons, aralkoxy of 7-15 carbons, aliphatic acyloxy of 2-20 carbons, alicyclic acyloxy of 6-13 carbons, aryl acyloxy of 7-15 carbons, alkylthio of 1-12 carbons, trialkoxysilyl of 3-12 carbons or araliphatic acyloxy of 8-16 carbons, wherein any alkyl or cycloalkyl substituent group may contain isolated double bonds;

$R^{15}$ is hydrogen, substituted or unsubstituted aliphatic of 1-20 carbons, substituted or unsubstituted alicyclic of 5-12 carbons, substituted or unsubstituted aryl of 6-14 carbons or substituted or unsubstituted araliphatic of 7-22 carbons;

When Q is —C(=O)—, $R^{15}$ may also be 2-(3,5-dialkyl-4-hydroxyphenyl)ethyl of 13-21 carbons, 3,5-dialkyl-4-hydroxyphenyl of 11-19 carbons in which the alkyl groups are branched or unbranched alkyl of 1-8 carbons, 4-benzoyl-3-hydroxyphenoxymethyl, 2-alkylthioethyl of 3-20 carbons, alkylthiomethyl of 2-20 carbons, 2-(dialkylaminoalkylthio)ethyl of 5-30 carbons or $R^{16}$—NH—C(=O)—$R^3$—, in which $R^3$ is as previously defined and $R^{16}$ is as defined below;

When Q is —C(=O)—O—, $R^{15}$ may also be 2,2,6,6-tetramethyl-4-piperidinyl, in which the piperidinyl nitrogen is unsubstituted or substituted with methyl, ethyl, allyl, oxyl, hydroxyl, benzyl, benzoyl or acetyl; 2-(3-hydroxy-4-benzoylphenoxy)ethyl; 2-acryloyloxyethyl; 2-methacryloyloxyethyl; 2-(3-hydroxy-4-benzotriazol-2-ylphenoxy)ethyl; 3-(3-benzotriazol-2-yl-4-hydroxyphenyl)propyl, in which the benzotriazolyl may be substituted in the 5 position with chlorine, methoxy, ethoxy, methoxycarbonyl or ethoxycarbonyl and the phenyl group may be substituted ortho to the hydroxy group with an alkyl group of 11-12 carbons or an aralkyl group of 9-12 carbons; 2-(3,5-dialkyl-4-hydroxyphenyl)ethyl of 13-21 carbons, 3-(3,5-dialkyl-4-hydroxyphenyl)propyl of 14-22 carbons or 2-[3-(3,5-dialkyl-4-hydroxyphenyl)propionyloxy]ethyl of 16-24 carbons, in which the alkyl groups are branched or unbranched alkyl groups of 1-8 carbons; with the proviso that when Q is —C(=O)—O—, $R^{15}$ is not hydrogen;

$R^{16}$ is substituted or unsubstituted aliphatic of 1-20 carbons, substituted or unsubstituted alicyclic of 5-12 carbons, substituted or unsubstituted aryl of 6-14 carbons, substituted or unsubstituted araliphatic of 7-22 carbons, 3,5-dialkyl-4-hydroxyphenyl of 11-19 carbons in which the alkyl groups are independently branched or unbranched alkyl of 1-8 carbons or 2,2,6,6-tetramethyl-4-piperidinyl, in which the nitrogen may be substituted with methyl, ethyl, allyl, oxyl, hydroxyl, benzyl, benzoyl or acetyl; and $R^{17}$ is a substituted or unsubstituted aliphatic diradical of 1–20 carbons, substituted or unsubstituted aryl diradical of 6–12 carbons, substituted or unsubstituted alicyclic diradical of 5–12 carbons or substituted or unsubstituted araliphatic diradical of 7–22 carbons, where the diradicals may contain 1–6 —O—, —S— or —NH— heteroatoms, with the proviso that multiple heteroatoms must be separated from each other and the diradical ends by at least one carbon atom; substituents for any of R, $R^2$, $R^3$, $R^4$, $R^6$, $R^7$, $R^8$, $R^9$, $R^{11}$, $R^{12}$, $R^{15}$, $R^{16}$ or $R^{17}$ may be one or more of chloro, bromo, alkyl of 1–8 carbons, alkoxy of 1–8 carbons, phenoxy, cyano, hydroxy, epoxy, carboxy, alkoxycarbonyl of 2–6 carbons, alkanoyloxy of 1–4 carbons, alkanoyl of 1–4 carbons, acryloyl, acryloyloxy, methacryloyl, methacryloyloxy, hydroxymethyl, 2-hydroxyethyl, alkylthio of 1–4 carbons or trialkoxysilyl of 3–12 carbons, with the proviso that when Q is —C(=O)—, $R^{15}$ may not be substituted with a carboxy group; and where R is 2-hydroxy substituted aliphatic or 2-hydroxy substituted alicyclic, R may also be substituted by aliphatic of 1–20 carbons, alicyclic of 5–12 carbons, aryl of 6–14 carbons, araliphatic of 7–22 carbons, alkoxy of 1–20 carbons, cycloalkoxy of 5–12 carbons, aryloxy of 6–14 carbons, aralkoxy of 7–15 carbons, aliphatic acyloxy of 2–20 carbons, alicyclic acyloxy of 6–13 carbons, aryl acyloxy of 7–15 carbons or araliphatic acyloxy of 8–16 carbons, where any alkyl or cycloalkyl substituent group of the 2-hydroxy substituted group may contain isolated double bonds.

Preferably, R is hydrogen, substituted or unsubstituted alkyl of 1–10 carbons, substituted or unsubstituted alkenyl of 3–8 carbons, substituted or unsubstituted benzyl, 2-cyanoethyl, acetyl, substituted or unsubstituted benzoyl, 2-hydroxyalkyl of 2–10 carbons, 2-hydroxy-3-phenoxypropyl or 2-hydroxy-3-(2-ethylhexoxy)propyl.

More preferably, R is hydrogen, methyl, acetyl or benzoyl.

Preferably, $R^1$ is hydrogen or methyl and is more preferably hydrogen.

Preferably, $R^2$ is hydrogen, alkyl of 1–4 carbons or a 2,2,6,6-tetramethyl-4-piperidinyl radical, or may be linked with $R^3$ to form a 5-membered lactam ring.

More preferably, $R^2$ is hydrogen.

Preferably, $R^3$ is a direct bond, an alkylene diradical of 1–8 carbons or an o-, m- or p-phenylene diradical, or may be linked with $R^2$ to form a 5-membered lactam ring.

More preferably, $R^3$ is a direct bond or an alkylene diradical of 1–7 carbons.

Preferably, $R^4$ is hydrogen.

Preferably, Q is —C(=O)—, —C(=O)—O—, or —C(=O)—N($R^4$)—, and more preferably, Q is —C(=O)— or —C(=O)—NH—.

Preferably, $R^6$ and $R^7$ are independently hydrogen, substituted or unsubstituted aliphatic of 1–8 carbons, substituted or unsubstituted phenyl or substituted or unsubstituted benzyl.

More preferably, $R^6$ is hydrogen, methyl or ethyl and $R^7$ is substituted or unsubstituted aliphatic of 1–8 carbons or substituted or unsubstituted phenyl.

Preferably, $R^8$ is substituted or unsubstituted aliphatic of 1–8 carbons, substituted or unsubstituted phenyl or substituted or unsubstituted benzyl.

More preferably, $R^8$ is substituted or unsubstituted alkyl of 1–4 carbons.

Preferably, $R^9$ is hydrogen, substituted or unsubstituted aliphatic of 1–8 carbons, substituted or unsubstituted phenyl or substituted or unsubstituted benzyl.

Preferably, $R^{11}$ and $R^{12}$ are independently hydrogen, alkyl of 1–8 carbons, cycloalkyl of 5–8 carbons, substituted or unsubstituted aryl of 6–12 carbons where the substituents are hydroxy or lower alkyl of 1–4 carbons, or $R^{11}$ and $R^{12}$ may be linked together to form an alicyclic ring of 5–8 carbons or may be linked together through a nitrogen atom to form a 2,2,6,6-tetramethyl-4-piperidinyl ring.

More preferably, $R^{11}$ and $R^{12}$ are independently lower alkyl of 1–4 carbons or may be linked together to form a cyclopentyl, cyclohexyl or cyclooctyl ring or may be linked together through a nitrogen atom to form a 2,2,6,6-tetramethyl-4-piperidinyl ring.

Preferably, $R^{13}$ is hydrogen, alkyl of 1–10 carbons, cycloalkyl of 5–8 carbons, aralkyl of 7–9 carbons, phenyl, substituted or unsubstituted 2-hydroxyalkyl of 2–12 carbons or substituted or unsubstituted 2-hydroxycycloalkyl of 5–8 carbons where the substituents may be alkyl of 1–8 carbons, cycloalkyl of 5–8 carbons, aryl of 6–10 carbons, alkoxy of 1–8 carbons, aryloxy of 6–14 carbons, aliphatic acyloxy of 2–8 carbons, cycloaliphatic acyloxy of 6–9 carbons, aryl acyloxy of 7–10 carbons or araliphatic acyloxy of 8–10 carbons.

More preferably, $R^{13}$ is hydrogen, alkyl of 1–4 carbons, cyclohexyl, benzyl, phenyl, substituted or unsubstituted 2-hydroxyalkyl of 2–10 carbons or 2-hydroxycyclohexyl where the substituents may be alkyl of 1–8 carbons, phenoxy, acetoxy, acryloyloxy, methacryloyloxy or benzoyloxy.

Preferably, $R^{14}$ is alkyl of 1–10 carbons, cycloalkyl of 5–8 carbons, aralkyl of 7–9 carbons, phenyl, substituted or unsubstituted 2-hydroxyalkyl of 2–12 carbons or substituted or unsubstituted 2-hydroxycycloalkyl of 5–8 carbons where the substituents may be alkyl of 1–8 carbons, cycloalkyl of 5–8 carbons, aryl of 6–10 carbons, alkoxy of 1–8 carbons, aryloxy of 6–14 carbons, aliphatic acyloxy of 2–8 carbons, cycloaliphatic acyloxy of 6–9 carbons, aryl acyloxy of 7–10 carbons or araliphatic acyloxy of 8–10 carbons.

More preferably, $R^{14}$ is alkyl of 1–4 carbons, cyclohexyl, benzyl, phenyl, substituted or unsubstituted 2-hydroxyalkyl of 2–10 carbons or 2-hydroxycyclohexyl where the substituents may be alkyl of 1–8 carbons, phenoxy, acetoxy, acryloyloxy, methacryloyloxy or benzoyloxy.

Preferably, $R^{15}$ is aliphatic of 1–18 carbons, aryl of 6–12 carbons, aralkyl of 7–18 carbons or cycloalkyl of 6–8 carbons; and when Q is —C(=O)—, $R^{15}$ is preferably also 3,5-di-t-alkyl-4-hydroxyphenyl of 14–18 carbons, 2-(3,5-di-t-alkyl-4-hydroxyphenyl)ethyl of 16–20 carbons, 4-benzoyl-3-hydroxyphenoxymethyl, 2-alkylthioethyl of 8 to 20 carbons or $R^{16}$—NH—C(=O)—$R^3$—, where $R^3$ is a direct bond or a 1,2-ethylene diradical, $R^{16}$ is hydrogen, alkyl of 1–12 carbons, aryl of 6–10 carbons, 3,5-di-t-alkyl-4-hydroxyphenyl of 14–18 carbons or 2,2,6,6-tetramethyl-4-piperidinyl, in which the piperidinyl nitrogen may be substituted with methyl or acetyl; and when Q is —C(=O)—O—, $R^{15}$ is also preferably 2,2,6,6-tetramethyl-4-piperidinyl in which the piperidinyl nitrogen is unsubstituted or substituted with methyl, benzoyl or acetyl;

2-(3-hydroxy-4-benzoylphenoxy)ethyl;

2-(3,5-di-t-butyl-4-hydroxyphenyl)ethyl;

3-(3,5-di-t-butyl-4-hydroxyphenyl)propyl;
2-(3-hydroxy-4-benzotriazol-2-ylphenoxy)ethyl;
2-acryloyloxyethyl; and 2-methacryloyloxyethyl.

More preferably, $R^{15}$ is methyl, ethyl, propyl, isopropyl, butyl, pentyl, hexyl, heptyl, nonyl, undecyl, tridecyl, pentadecyl, heptadecyl, octadecyl, phenyl, 2-hydroxyphenyl, dimethyl-m-isopropenylbenzyl; and when Q is $-C(=O)-$, $R^{15}$ is also more preferably 3,5-di-t-butyl-4-hydroxyphenyl, 2-(3,5-di-t-butyl-4-hydroxyphenyl)ethyl, 4-benzoyl-3-hydroxyphenoxymethyl, undecyl, heptadecyl or $R^{16}-NH-C(=O)-R^3$, where $R^3$ is a direct bond and $R^{16}$ is 3,5-di-t-butyl-4-hydroxyphenyl or 2,2,6,6-tetramethyl-4-piperidinyl; and when Q is $-C(=O)-O-$, $R^{15}$ is also more preferably allyl, methallyl, 2,2,6,6-tetramethyl-4-piperidinyl, 1,2,2,6,6-pentamethyl-4-piperidinyl, or 2-(3-hydroxy-4-benzoylphenoxy)ethyl.

Preferably, $R^{17}$ is an aliphatic diradical of 2–12 carbons, a cycloalkylene diradical of 5–12 carbons, an alicyclic diradical of 7–12 carbons, an aryl diradical of 6–12 carbons or an aralkylene diradical of 7–12 carbons.

More preferably, $R^{17}$ is an alkylene diradical of 2–10 carbons or an o-, m-, or p-phenylene diradical which may be substituted with a methyl group, cycloalkylene of 9–10 carbons or aralkylene of 8–12 carbons.

DETAILED DESCRIPTION OF THE PREFERRED EMBODIMENTS

The novel derivatives of N-(2,2,6,6-tetraalkyl-4-piperidinyl)amic acid hydrazides of the present invention contain both a hindered amine light stabilizing group and an amic acid hydrazide derivative. The amic acid hydrazide derivative enhances the photooxidative stabilizing properties of the hindered amine groups and imparts thermooxidative stabilizing and metal complexing properties to the compounds. By careful selection of the derivative, the compatibility of the novel compounds with various host resins to be stabilized can be increased. The novel compounds of the present invention have low volatility and are not readily lost from polymeric systems via volatilization, exudation, migration or extraction.

GENERIC GROUP EXAMPLES

The present invention comprises a compound which is a N-HALS-substituted amic acid hydrazide derivative of structural Formula I set forth in the above Summary of the Invention. The Summary also sets forth preferred and more preferred embodiments of the various constituent groups of the compound. Specific, non-limiting examples of particular constituent groups are as follows:

As a substituted or unsubstituted aliphatic of 1–20 carbons R, $R^2$, $R^4$, $R^6$, $R^7$, $R^8$, $R^9$, $R^{11}$, $R^{12}$, $R^{13}$, $R^{14}$, $R^{15}$ and $R^{16}$ may be, for example, methyl, ethyl, n-propyl, isopropyl, allyl, hexyl, heptyl, octyl, nonyl, decyl, propargyl, octadecyl, dodecyl, isododecyl, tetradecyl, 2-methallyl, 2-hexenyl, 10-undecenyl, 2-dodecenyl, n-butyl, 2-hydroxyethyl, 2-butenyl, 2-hydroxypropyl, cyanomethyl, 2,3-epoxypropyl, dimethylaminoethyl, 2-hydroxy-3-phenoxypropyl, 2-hydroxy-3-(2-ethylhexoxy)propyl or 2-hydroxyoctyl.

As a substituted or unsubstituted alicyclic of 5–12 carbons, R, $R^2$, $R^4$, $R^6$, $R^7$, $R^8$, $R^9$, $R^{11}$, $R^{12}$, $R^{13}$, $R^{14}$, $R^{15}$ and $R^{16}$ may be, for example, cyclohexyl, trimethylcyclohexyl, cyclooctyl, cyclododecyl, 4-t-butylcyclohexyl, 3-cyclohexenyl, cyclododecyl, 4-octylcyclohexyl or 2-methyl-4-octylcyclohexyl.

As substituted or unsubstituted aryl of 6–14 carbons, $R^2$, $R^6$, $R^7$, $R^8$, $R^9$, $R^{11}$, $R^{12}$, $R^{13}$, $R^{14}$, $R^{15}$ and $R^{16}$ may be for example phenyl tolyl, 4-chlorophenyl, isopropylphenyl, anisyl, 3,5-di-t-butyl-4-hydroxyphenyl, naphthyl, 3-methyl-5-t-butyl-4-hydroxyphenyl, 3,4,5-trimethoxyphenyl or 4-dimethylaminophenyl.

As a substituted or unsubstituted araliphatic group of 7–22 carbons, R, $R^2$, $R^4$, $R^6$, $R^7$, $R^8$, $R^9$, $R^{11}$, $R^{12}$, $R^{13}$, $R^{14}$, $R^{15}$ and $R^{16}$ may be, for example, benzyl, 3-methylbenzyl, 4-t-butylbenzyl, cinnamyl, 3,5-di-t-butyl-4-hydroxybenzyl, 2-phenylethyl, cumyl, trimethylbenzyl, 4-octyloxybenzyl, naphthylmethyl or (4-dodecylphenyl)methyl.

As a substituted or unsubstituted aliphatic acyl of 2–20 carbons, substituted or unsubstituted alicyclic acyl of 7–16 carbons, substituted or unsubstituted aryl acyl of 7–11 carbons or substituted or unsubstituted araliphatic acyl of 7–22 carbons, R may be, for example, formyl, acetyl, chloroacetyl, acryloyl, methacryloyl, propionyl, butyryl, 2-methylpropionyl, caproyl, capryloyl, lauroyl, crotonoyl, stearoyl, cyclohexylcarbonyl, 4-t-butylcyclohexylcarbonyl, 3-cyclohexeny-1-carbonyl, cyclododecylcarbonyl, 4-octylcyclohexylcarbonyl, 2-ethoxy-2-oxoacetyl, 2-methoxy-2-oxoacetyl, 2-methyl-4-octylcyclohexylcarbonyl, benzoyl, toluoyl, 4-chlorobenzoyl, isopropylbenzoyl, anisoyl, 3,5-di-t-butyl-4-hydroxybenzoyl, naphthoyl, 3-methyl-5-t-butyl-4-hydroxybenzoyl, 3,4,5-trimethoxybenzoyl, 4-dimethylaminobenzoyl, 3-(3,5-di-t-butyl-4-hydroxyphenyl)propionyl, cinnamoyl or dihydrocinnamoyl. R is preferably alkanoyl of 2–5 carbons, cyclohexylcarbonyl, benzoyl or phenacyl.

As $-C(=O)-N(R^6)(R^7)$, R may be, for example, N-methylcarbamoyl, N-(n-butyl)carbamoyl, N-dodecylcarbamoyl, N,N-dimethylcarbamoyl, N,N-diethylcarbamoyl, N,N-di(n-hexyl)carbamoyl, piperidin-1-ylcarbonyl, 2,2,6,6-tetramethyl-4-piperidinylcarbonyl, piperazine-1-carbonyl, 4-methylpiperazine-1-carbonyl, morpholin-1-carbonyl, 2-(dibutylamino)-2-oxoacetyl, 2-(phenylamino)-2-oxoacetyl, N-phenylcarbamoyl, N-(4-butylphenyl)carbamoyl, N-(alphanaphthyl)carbamoyl, N-phenyl-N-hexylcarbamoyl, N-(trimethylphenyl)-N-amylcarbamoyl, N,N-diphenylcarbamoyl, N,N-di(4-methylphenyl)carbamoyl or N-(4-benzylaminophenyl)-N-phenylcarbamoyl.

As $-(C(=O))_a-O-R^8$, R may be, for example, methoxycarbonyl, 2-ethoxy-2-oxoacetyl, 2-methoxy-2-oxoacetyl, 2-cyclohexyloxy-2-oxoacetyl, ethoxycarbonyl, phenoxycarbonyl, (2-methylphenoxy)carbonyl, allyloxycarbonyl, cyclododecyloxycarbonyl, 2-ethylhexoxycarbonyl, ethoxycarbonyl, isopropoxycarbonyl or (4-octyloxyphenyl)carbonyl.

As $-(CH_2)_a-C(=O)-O-R^9$, R may be, for example, ethoxycarbonylmethyl, methoxycarbonylmethyl, methoxycarbonylethyl, butoxycarbonylmethyl, (benzyloxy)carbonylmethyl or (benzyloxy)carbonylethyl.

As $-(CH_2-CH(R^1)-O)_b-R^{10}$, R is, for example, nonylphenoxypoly(ethoxy)ethyl, butoxypoly(propoxy)ethyl, hydroxypoly(ethoxy)ethyl or 2-[hydroxypoly(propoxy)]-2-methylethyl.

As a lower alkyl group of 1–4 carbons, $R^1$ may be, for example, methyl, ethyl, propyl, isopropyl, n-butyl, sec-butyl or t-butyl.

As an aliphatic group of 1–4 carbons, $R^{10}$ may be, for example, methyl, ethyl, propyl, isopropyl, allyl, n-butyl, sec-butyl or isobutyl.

As a substituted or unsubstituted aliphatic diradical of 1–20 carbons, a substituted or unsubstituted aryl diradical of 6–12 carbons, a substituted or unsubstituted alicyclic diradical of 5–12 carbons or a substituted or unsubstituted araliphatic diradical of 7–22 carbons optionally containing 1–6 —O—, —S— or —NH— heteroatoms, $R^3$ and $R^{17}$ may be, for example, methylene, ethane-1,2-diyl, ethene-1,2-diyl, propane-1,3-diyl, propene-1,2-diyl, 2-thiopropene-1,3-diyl, 2-oxapropane-1,3-diyl, hexane-1,3-diyl, 2-azapropane-1,3-diyl, 2-methyl-2-azapropane-2,3-diyl, cyclohexane-1,2-diyl, 1,2-phenylene, 1,3-phenylene, 1,4-phenylene, hexane-1,6-diyl, octane-1,8-diyl, decane-1,10-diyl, dodecane-1,12-diyl, 3-hexen-1,6-diyl, 4-methyl-1,2-phenylene, 4-chloro-1,2-phenylene, 4-methylcyclohexane-1,2-diyl, cyclohexane-1,2-diyl, 4-methyl-4-cyclohexane-1,2-diyl, toluene-alpha,2-diyl, toluene-alpha,4-diyl or toluene-alpha,3-diyl.

As a substituted or unsubstituted 2-hydroxyalkyl of 2–20 carbons or substituted or unsubstituted 2-hydroxycycloalkyl of 5–12 carbons, $R^{13}$ and $R^{14}$ may be, for example, 2-hydroxyethyl, 2-hydroxypropyl, 2-hydroxybutyl, 1-methyl-2-hydroxypropyl, 2-hydroxycyclododecyl, 2-hydroxydecyl, 2-hydroxycyclohexyl, 2-hydroxycyclopentyl, 2-hydroxydodecyl, 2-hydroxy-2-phenylethyl, 2-hydroxyhexadecyl, 2-hydroxyhexyl, 2-hydroxy-5-hexenyl, 2-hydroxyoctadecyl, 2-hydroxy-3-methacryloyloxypropyl, 2-hydroxy-3-acryloyloxypropyl, 2-hydroxy-3-phenoxypropyl, 2-hydroxy-3-(4-methoxyphenoxy)propyl, 2-hydroxy-3-isopropoxypropyl, 2-hydroxy-3-methoxypropyl, 2-hydroxy-3-(2-ethylhexoxy)propyl, 2-hydroxy-3-benzyloxypropyl or 2-hydroxy-3-benzoyloxypropyl.

When $R^{11}$ and $R^{12}$ are linked together to form a substituted or unsubstituted alicyclic ring of 5–12 carbon atoms or are linked together through a heteroatom to form a heterocyclic ring of 5–12 atoms, where the heteroatom is —O—, —S— or —NH—, the —NH— being optionally substituted by lower alkyl of 1–4 carbons, $R^{11}$ and $R^{12}$ together with the carbon to which they are attached may form, for example, cyclopentyl, cyclohexyl, cyclohexenyl, cycloheptyl, 4-t-butylcyclohexyl, 2-methylcyclohexyl, cyclooctyl, cyclododecyl, 2,2,6,6-tetramethyl-4-piperidinyl, 2,6-diethyl-2,3,6-trimethyl-4-piperidinyl, 1,2,2,6,6-pentamethyl-4-piperidinyl, 1-ethyl-2,2,6,6-tetramethyl-4-piperidinyl, 4-oxacyclohexyl or 4-thiocyclohexyl rings.

When $R^2$ and $R^3$ are linked together to form a 5-membered lactam ring, $R^2$ and $R^3$ together with the nitrogen atom to which they are attached may form, for example, a 1-aza-2-oxocyclopentane-1,4-diyl diradical.

As a 2-(3,5-dialkyl-4-hydroxyphenyl)ethyl group of 13–21 carbons, $R^{15}$ may be, for example, 2-(3,5-di-t-butyl-4-hydroxyphenyl)ethyl, 2-(3,5-di-t-amyl-4-hydroxyphenyl)ethyl or 2-(3-t-butyl-5-methyl-4-hydroxyphenyl)ethyl.

As a 3,5-dialkyl-4-hydroxyphenyl group of 11–19 carbons, $R^{15}$ and $R^{16}$ may be, for example, 3,5-di-t-butyl-4-hydroxyphenyl, 3,5-di-t-amyl-4-hydroxyphenyl or 3-t-butyl-5-methyl-4-hydroxyphenyl.

As a 2-alkylthioethyl group of 3–20 carbons, $R^{15}$ may be, for example, 2-methylthioethyl, 2-hexylthioethyl, 2-octylthioethyl, 2-dodecylthioethyl or 2-octadecylthioethyl.

As a 2-alkylthiomethyl group of 2–20 carbons, $R^{15}$ may be, for example, methylthiomethyl, ethylthiomethyl, propylthiomethyl, hexylthiomethyl, dodecylthiomethyl or octadecylthiomethyl.

As a 2-(dialkylaminoalkylthio)ethyl group of 5–30 carbons, $R^{15}$ may be, for example, 2-(dimethylaminomethylthio)ethyl, 2-[2-(dimethylamino)ethylthio]ethyl, 2-[3-(dimethylamino)propylthio]ethyl, 2-[2-(diethylamino)ethylthio]ethyl or 2-[3-(diethylaminopropylthio)ethyl].

When $R^{13}$, $R^{14}$ and R are substituted 2-hydroxyaliphatic or 2-hydroxyalicyclic, optional substituents are, for example, methyl, ethyl, propyl, n-butyl, sec-butyl, t-butyl, hexyl, octyl, decyl, dodecyl, octadecyl, allyl, methallyl, cyclopentyl, cyclohexyl, cyclooctyl, cyclododecyl, 4-methylcyclohexyl, phenyl, 4-methoxyphenyl, benzyl, cumyl, phenethyl, 3,5-di-t-butyl-4-hydroxyphenyl, (3,5-di-t-butyl-4-hydroxyphenyl)ethyl, methoxy, ethoxy, propoxy, butoxy, isopropoxy, t-butoxy, hexoxy, 2-ethylhexoxy, dodecyloxy, octadecyloxy, cyclopentoxy, cyclohexoxy, 4-t-butylcyclohexoxy, phenoxy, 2,5-di-t-butyl-4-hydroxyphenoxy, benzyloxy, 3,5-di-t-butyl-4-hydroxyphenoxy, 3,5-di-t-butyl-4-hydroxybenzyloxy, acetoxy, propionoxy, butyryloxy, lauroyloxy, stearoyloxy, cyclohexanecarbonyloxy, cyclopentanecarbonyloxy, benzoyloxy, 3,5-di-t-butyl-4-hydroxybenzoyloxy, 3-phenylpropionoxy, phenylacetyloxy, 3-(3,5-di-t-butyl-4-hydroxyphenyl)propionoxy or 3-(3-t-butyl-5-methyl-4-hydroxyphenyl)propionoxy.

LIST OF ILLUSTRATIVE COMPOUNDS

Non-limiting examples of suitable derivatives of N-HALS-substituted amic acid hydrazides of Formula I include:

(1) 2,2'-[N-(2,2,6,6-tetramethyl-4 piperidinyl)oxamoyl]-terephthalic acid dihydrazide (2) 2,2'-[N-(1-acetyl-2,2,6,6-tetramethyl-4-piperidinyl)oxamoyl]dodecanoic acid dihydrazide (3) 2,2'-[N-(1-methyl-2,2,6,6-tetramethyl-4-piperidinyl)-succinamoyl]-1,4-cyclohexylene dicarboxylic acid dihydrazide (4) 1,4-phenylene bis[2-(N,N-bis(2,2,6,6-tetramethyl-4-piperidinyl)isophthalamoyl)carbazate]

(5) 1,12-dodecamethylene bis[2-(N-methyl-N-(2,2,6,6-tetramethyl-4-piperidinyl)-oxamoyl)carbazate]

(6) 2,2'-[N-(2,2,6,6-tetramethyl-4-piperidinyl)succinamoyl]isophthalic acid dihydrazide (7) 1-[N-n-butyl-N-(1-allyloxycarbonyl-2,2,6,6-tetramethyl-4piperidinyl)succinamoyl]-2-(3,5-di-t-amyl-4-hydroxybenzoyl)hydrazine (8) N-[1-butoxypoly(propoxy)ethyl-2,2,6,6-tetramethyl-4-piperidinyl)-N'-(t-butylamino)oxamide (9) N-(1-phenylcarbamoyl-2,2,6,6-tetramethyl-4-piperidinyl)-N'-(cyclohexylamino)isophthalamide

(10) 1-(N-[1-(2-ethoxy-2-oxoacetyl)-2,2,6,6-tetramethyl-4-piperidinyl]oxamoyl)-2-(n-butylcarbamoyl)hydrazine

(11) 1-(N-[1-(2-methoxy-2-oxoacetyl)-2,2,6,6-tetramethyl-4-piperidinyl]azelamoyl)-2-(cyclohexylcarbamoyl)hydrazine

(12) 1-(N-[1-(methoxycarbonylmethyl)-2,2,6,6-tetramethyl-4-piperidinyl]oxamoyl)-1-methyl-2-(benzylcarbamoyl)hydrazine

(13) 1-(N-[1-(3,5-di-t-butyl-4-hydroxybenzyl)-2,2,6,6-tetramethyl-4-piperidinyl]oxamoyl)-2-[3-(hexylthio)-propionyl]hydrazine

(14) 1-[N-(1-acetyl-2,2,6,6-tetramethyl-4-piperidinyl)oxamoyl]-2-acetylhydrazine

(15) 1-[N-(1-benzoyl-2,2,6,6-tetramethyl-4-piperidinyl)oxamoyl]-2benzoylhydrazine

(16) 1-[N-(2-cyanoethyl)-N-(1-(2-cyanoethyl)-2,2,6,6-tetramethyl-4-piperidinyl)succinamoyl]-2-(cyclohexoxycarbonyl)hydrazine

(17) 1-[N-(1-(2-hydroxyethyl)-2,2,6,6-tetramethyl-4-piperidinyl)adipamoyl]-2-(phenoxycarbonyl)hydrazine
(18) 1-[N-phenyl-N-(1-dimethylcarbamoyl-2,2,6,6-tetramethyl-4-piperidinyl)terephthalamoyl]-2-dodecanoylhydrazine
(19) 1-benzyl-1-[N-benzyl-N-(1-n-butylcarbamoyl-2,2,6,6-tetramethyl-4-piperidinyl)-oxamoyl]-2-benzylhydrazine
(20) 1-cyclohexyl-1-[N-(1-ethoxycarbonyl-2,2,6,6-tetramethyl-4-piperidinyl)oxamoyl]-2-[3-(dodecylthio)-propionyl]hydrazine
(21) 1-[N-(1-oxyl-2,2,6,6-tetramethyl-4-piperidinyl)oxamoyl]-2-(methylcarbamoyl)hydrazine
(22) 1-[N-(1-hydroxyl-2,2,6,6-tetramethyl-4-piperidinyl)oxamoyl]-2-octanoylhydrazine
(23) 1-[N-(2,6-diethyl-1,2,3,6-tetramethyl-4-piperidinyl)oxamoyl]-2-(dimethylcarbamoyl)hydrazine
(24) 1-[N-ethyl-N-(1-ethyl-2,2,6,6-tetramethyl-4-piperidinyl)succinamoyl]-2-decanoylhydrazine
(25) N-n-butyl-N-(1-allyl-2,2,6,6-tetramethyl-4-piperidinyl)-N'-(phenylamino)oxamide
(26) N-methyl-N-(1-benzyl-2,2,6,6-tetramethyl-4-piperidinyl)-N'-(diethylamino)oxamide
(27) 1-[N-cyclohexyl-N-(1-cyclohexyl-2,2,6,6-tetramethyl-4-piperidinyl)adipamoyl]-2-methyl-2-(n-propylcarbamoyl)hydrazine
(28) 1-[N-(2,2,6,6-tetramethyl-4-piperidinyl)-3,3'-thiodipropionamoyl]-2-(benzyloxycarbonyl)hydrazine
(29) 1-n-Butyl-1-[N-(2,2,6,6-tetramethyl-4-piperidinyl)-3-oxapimelamoyl]-2-formylhydrazine
(30) 1-(1-acetyl-2,2,6,6-tetramethyl-4-piperidinyl)-1-[N,N-bis(1-acetyl-2,2,6,6-tetramethyl-4-piperidinyl)-3-azapimelamoyl]-2-propionylhydrazine
(31) 1-[N-(2,2,6,6-tetramethyl-4-piperidinyl)succinamoyl]-2-methyl-2-(p-methylphenylcarbamoyl)-hydrazine
(32) 1-methyl-1-[N-(2,2,6,6-tetramethyl-4-piperidinyl)oxamoyl]-2-ethyl-2-(octadecylcarbamoyl)hydrazine
(33) 1-(N-[1-(3,5-di-t-butyl-4-hydroxybenzoyl)-2,2,6,6-tetramethyl-4-piperidinyl]oxamoyl)-2-(3,5-di-t-butyl-4-hydroxybenzoyl)hydrazine
(34) 1-(N-[1-(3-[3,5-di-t-butyl-4-hydroxyphenyl]propionyl)-2,2,6,6-tetramethyl-4-piperidinyl]succinamoyl)-2-[3-(3,5-di-t-butyl-4-hydroxyphenyl)propionyl]hydrazine
(35) 1-[N-cyclohexyl-N-(1-cyclohexylcarbonyl-2,2,6,6-tetramethyl-4-piperidinyl)malonamoyl]-2-(cyclohexylcarbonyl)hydrazine
(36) 1-[N,N-bis(2,2,6,6-tetramethyl-4-piperidinyl)oxamoyl]-2-dodecanoylhydrazine
(37) 1-[N,N-bis(1-methyl-2,2,6,6-tetramethyl-4-piperidinyl)oxamoyl]-2-(n-butylcarbamoyl)hydrazine
(38) N-(2,2,6,6-tetramethyl-4-piperidinyl)-N'-(dimethylamino)oxamide
(39) N-[1-(2-hydroxyethyl)-2,2,6,6-tetramethyl-4-piperidinyl]-N'-[di-(2-hydroxyethyl)amino]oxamide
(40) 1-[N-ethyl-N-(2,2,6,6-tetramethyl-4-piperidinyl)azelamoyl]-2-(dimethylthiocarbamoyl)hydrazine
(41) 1-methyl-1-[N-(2,2,6,6-tetramethyl-4-piperidinyl)oxamoyl]-2-propionylhydrazine
(42) 1-[N-(1,2,2,6,6-pentamethyl-4-piperidinyl)oxamoyl]-2-[3-(3,5-di-t-amyl-4-hydroxyphenyl)propionyl]hydrazine
(43) 1-(N-[1-(3-(3-t-butyl-5-methyl-4-hydroxyphenyl)-propionyl)-2,2,6,6-tetramethyl-4-piperidinyl]oxamoyl]-2- [3-(3-t-butyl-5-methyl-4-hydroxyphenyl)-propionyl]hydrazine
(44) 1-[N-(2,2,6,6-tetramethyl-4-piperidinyl)oxamoyl]-2-[3-(2-dimethylaminoethylthio)propionyl]hydrazine
(45) 1,2-bis[N-(1-methyl-2,2,6,6-tetramethyl-4-piperidinyl)oxamoyl]hydrazine
(46) 1,2-bis[N-(1-acetyl-2,2,6,6-tetramethyl-4-piperidinyl)succinamoyl]hydrazine
(47) 1-[N-(2,2,6,6-tetramethyl-4-piperidinyl)oxamoyl]-2-[N-(octadecyl)oxamoyl]hydrazine
(48) 1-[N-(2,2,6,6-tetramethyl-4-piperidinyl)succinamoyl]-2-[N-(dodecyl)oxamoyl]hydrazine
(49) 1-[N-(2,2,6,6-tetramethyl-4-piperidinyl)oxamoyl]-2-[N-(3,5-di-t-butyl-4-hydroxyphenyl)succinamoyl]hydrazine
(50) 1-[N-(2,2,6,6-tetramethyl-4-piperidinyl)oxamoyl]-2-[2-(3-hydroxy-4-benzotriazol-2-ylphenoxy)ethoxycarbonyl]hydrazine
(51) 1-[N-(2,2,6,6-tetramethyl-4-piperidinyl)oxamoyl]-2-[3-(3-benzotriazol-2-yl-4-hydroxy-5-t-butylphenyl)-propoxycarbonyl]hydrazine
(52) 1-[N-(1-acetyl-2,2,6,6-tetramethyl-4-piperidinyl)oxamoyl]-2(allyloxycarbonyl)hydrazine
(53) 1-[N-(2,2,6,6-tetramethyl-4-piperidinyl)succinamoyl]-2-[2-(acryloyloxy)ethoxycarbonyl]hydrazine
(54) 1-[N-(1,2,2,6,6-pentamethyl-4-piperidinyl)oxamoyl]-2-[2-(methacryloyloxy)ethoxycarbonyl]hydrazine
(55) 1-[N-(2,2,6,6-tetramethyl-4-piperidinyl)oxamoyl]-2-[2-(3-(3,5-di-t-butyl-4-hydroxyphenyl)propionyloxy)ethoxycarbonyl]hydrazine
(56) 1-[N-(1-acetyl-2,2,6,6-tetramethyl-4-piperidinyl)adipamoyl]-2-(1,2,2,6,6-pentamethyl-4-piperidinyloxycarbonyl)hydrazine
(57) 1-[N-(1,2,2,6,6-pentamethyl-4-piperidinyl)oxamoyl]-2-(2,2,6,6-tetramethyl-4-piperidinyloxycarbonyl]hydrazine In addition to the examples of derivatives of N-HALS-substituted amic acid hydrazides set forth above, the hydrazone derivatives resulting from the reaction of N-(2,2,6,6-tetramethyl-4-piperidinyl)-N'-aminooxamide or N-(2,2,6,6-tetramethyl-4-piperidinyl)-N'-aminosuccinamide with 2-decanone, cyclododecanone, cyclopentanone, 1,3-diphenylacetone, dihydroisophorone, acetophenone, 4-piperidone, formaldehyde, acetaldehyde, salicylaldehyde or methyl cyclohexyl ketone are further non-limiting examples of illustrative compounds of the present invention.

PREPARATIVE METHODS

The compounds of the present invention, designated generally by Formula I, may be prepared by various methods, including one or more of the methods as follows. As indicated by variations within the formulas and methods, different methods may be preferred for use with different variations of Formula I.

Preparation of Starting Materials

The preparation of the N-(2,2,6,6-tetraalkyl-4-piperidinyl)amic acid hydrazide starting materials of Formula II (where $R^2$ and $R^3$ are not linked together) are disclosed in copending U.S. Pat. No. 4,983,738, the disclosure of which is incorporated herein by reference.

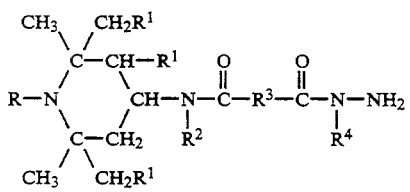

II

The cyclic lactams (i.e., the compounds of Formula II where $R^2$ and $R^3$ are linked together to form a 5-membered cyclic lactam) may be prepared by reacting 4-amino-2,2,6,6-tetraalkylpiperidines with dialkyl itaconates to form an intermediate 4-(alkoxycarbonyl)-1-(2,2,6,6-tetraalkyl-4-piperidinyl)-2-pyrrolidone according to the procedure described in U.S. Pat. No. 4,309,546, the disclosure of which is hereby incorporated herein by reference. The 4-alkoxycarbonyl group can then be converted to a hydrazide group by hydrazinoloysis with excess hydrazine hydrate in methanol, using standard reaction conditions.

I. Preparation of Hydrazones

The N-(2,2,6,6-tetraalkyl-4-piperidinyl)amic acid hydrazones of Formula I where n is 1 and $R^5$ is $-N=C(R^{11})(R^{12})$, designated as Formula III, are prepared by one or more of Methods A, B and C as follows.

Preparation Method A

The novel hydrazone derivatives of this invention may be prepared by reacting a hydrazide of Formula II with ketones, aldehydes or formaldehyde in inert solvents, preferably in hydrocarbon solvents under azeotropic conditions.

The reaction sequence of Method A is illustrated by the following equation:

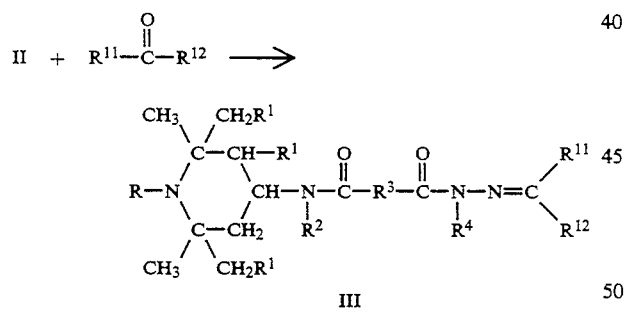

III

In the equation for Method A, R, $R^1$, $R^2$, $R^3$, $R^4$, $R^{11}$ and $R^{12}$ are as previously broadly defined.

Preparation Method B

The novel hydrazone derivatives of the present invention may also be prepared by reacting hydrazones of ketones or aldehydes with esters of N-(2,2,6,6-tetraalkyl-4-piperidinyl)amic acids of Formula IV, where $R^{18}$ is lower alkyl of 1 to 4 carbons or phenyl.

The reaction sequence of Method B is illustrated by the following equation:

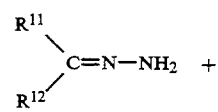

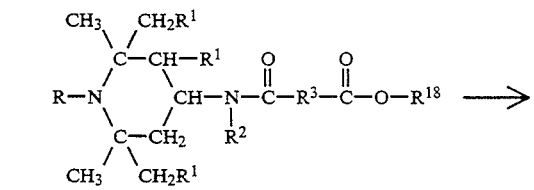

IV

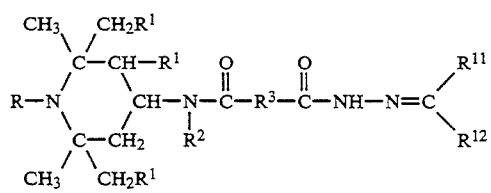

III

R, $R^1$, $R^2$, $R^3$, $R^{11}$, $R^{12}$ and $R^{18}$ are as previously broadly defined.

Preparation Method C

The hydrazone derivatives where $R^3$ is a direct bond may also be prepared by reacting hydrazones of ketones or aldehydes with oxalate diesters to form the intermediate of Formula V, which is then reacted with 4-amino-2,2,6,6-tetraalkylpiperidines.

The reaction sequence of Method C is illustrated by the following equations:

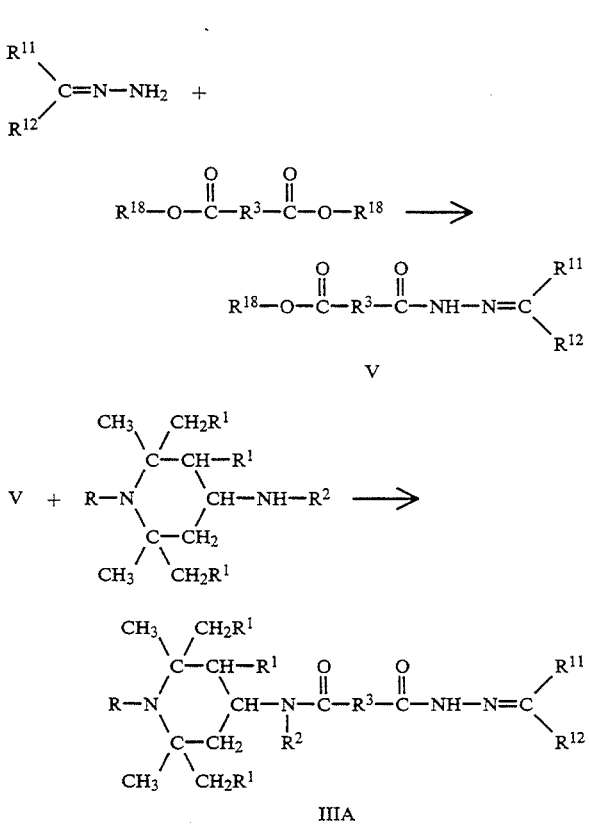

IIIA

In the equation for Method C, R, $R^1$, $R^2$, $R^{11}$, $R^{12}$ and $R^{18}$ are as previously defined and $R^3$ is a direct bond.

II. Preparation of Carbamoyl and Thiocarbamoyl Derivatives

The novel carbamoyl and thiocarbamoyl derivatives of N-(2,2,6,6-tetraalkyl-4-piperidinyl) amic acids of Formula I, designated as Formulas VI and VII, respectively, may be prepared by one or more of Methods D, E or F, as follows.

Preparation Method D

The novel carbamoyl and thiocarbamoyl derivatives, designated as Formulas VI and VII, where n is 1 and 2, respectively, and $R^5$ is —$N(R^6)$—Q—$R^{15}$ or —$N(R^6)$—Q—$R^{17}$—Q—$N(R^6)$— and Q is —C(=O)NH— or —C(=S)NH—, may be prepared by reacting a hydrazide of Formula II with isocyanates, isothiocyanates, diisocyanates or diisothiocyanates in aprotic polar solvents, such as tetrahydrofuran (THF) or dimethylformamide (DMF).

The reaction sequences of Method D are illustrated by the following equations:

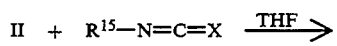

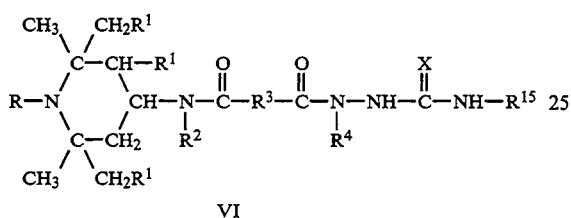

VI

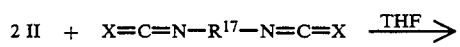

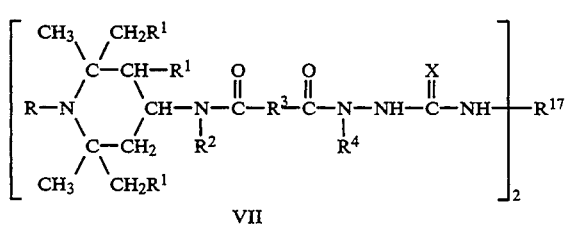

VII

X is O or S and R, $R^1$, $R^2$, $R^3$, $R^4$, $R^{15}$ and $R^{17}$ are as previously broadly defined.

Preparation Method E

The novel carbamoyl and thiocarbamoyl derivatives of Formula VI, where $R^5$ is —$N(R^6)$—Q—$R^{15}$ and Q is —C(=O)—NH— or —C(=S)—NH—, may also be prepared by reacting semicarbazides or esters of Formula IV of N-(2,2,6,6-tetraalkyl-4-piperidinyl)amic acids.

The reaction sequence of Method E is illustrated by the following equation:

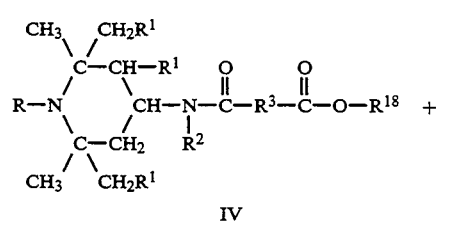

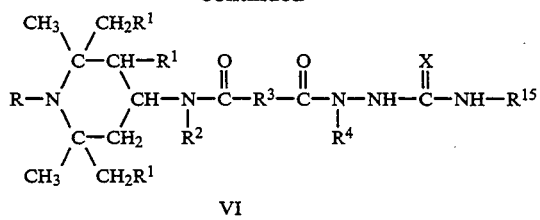

VI

X is O or S, and R, $R^1$, $R^2$, $R^3$, $R^4$, $R^{15}$ and $R^{18}$ are as previously broadly defined.

Preparation Method F

Carbamoyl or thiocarbamoyl derivatives of Formula VIA, where $R^3$ is a direct bond, $R^5$ is —$N(R^6)$—Q—$R^{15}$ and Q is —C(=O)—NH— or —C(=S)—NH—, may also be prepared by reacting semicarbazides or thiosemicarbazides with oxalate diesters to form the intermediate of Formula VIII which is then reacted with 4-amino-2,2,6,6-tetraalkylpiperidines.

The reaction sequence of Method F is illustrated by the following equations:

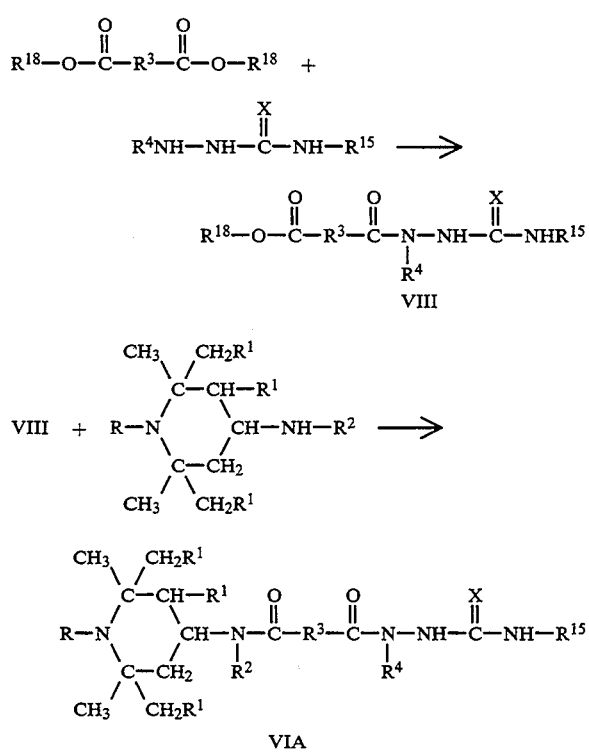

X is O or S and R, $R^1$, $R^2$, $R^4$, $R^{15}$ and $R^{18}$ are as previously defined and $R^3$ is a direct bond.

The reactions of hydrazides with ketones, aldehydes, isocyanates, diisocyanates, isothiocyanates and diisothiocyanates are well known in the art and can occur under a wide range of conditions, including varying temperatures, times, solvents and concentrations. Generally, a mole ratio of about 0.9 to about 1.0 to about 1.1 to about 1.0 of the hydrazide to the monofunctional co-reactant is employed. If the co-reactant is difunctional, then a mole ratio of about 1.8 to about 2.0 to about 1.1 to about 1.0 of the hydrazide to the difunctional co-reactant is employed. If the co-reactant is a compound that can easily be removed from the product by volatalization, for example, acetone or methyl ethyl ketone, lower mole ratios may be desirable. In fact, it may be desirable to use the co-reactant as the solvent.

III. Miscellaneous Reactions

The starting hydrazides of Formula II also react with unsubstituted or N-substituted amic acid esters in lower alcohol solutions to form 1,2-amoyl hydrazines, Formula IX, as indicated by the following reaction equation:

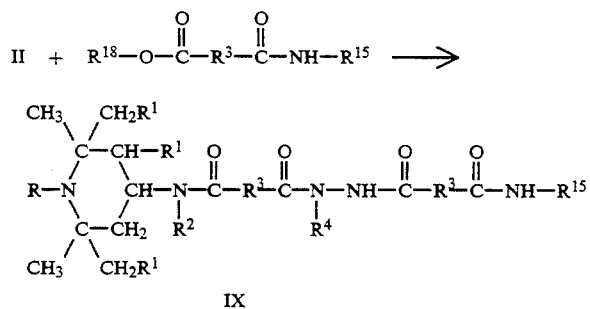

IX

The reactions are normally carried out in refluxing methanol but may be carried out in higher boiling aprotic solvents or without a solvent by heating a mixture of the two components above their melting points. The methyl and ethyl esters of N-substituted oxamates and succinamates are the preferred co-reactants and R, $R^1$, $R^2$, $R^3$, $R^4$, $R^{15}$ and $R^{18}$ are as previously broadly defined.

The novel acyl derivatives of Formula II, designated as Formula X, may be prepared by reacting the esters of Formula IV with acid hydrazides neat or in refluxing alcohols, such as methanol, ethanol or isopropanol, as indicated in the following reaction equation:

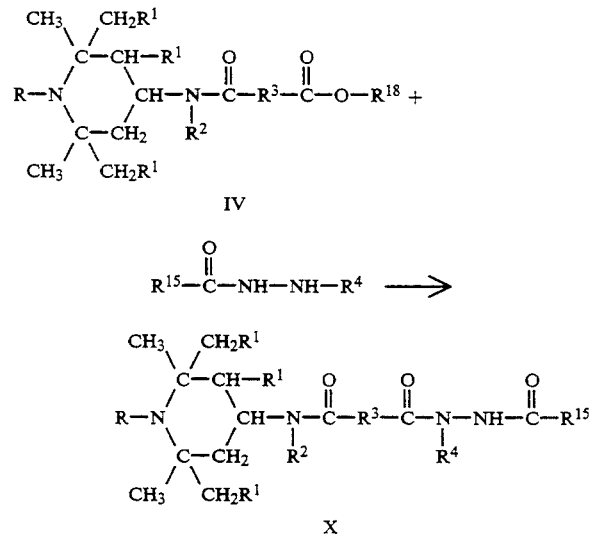

X

R, $R^1$, $R^2$, $R^3$, $R^4$, $R^{15}$ and $R^{18}$ are as previously broadly defined.

The novel acyl derivatives of Formula X may also be prepared by reacting the hydrazides of Formula II with non-cyclic carboxylic acid anhydrides, as indicated per the following equation:

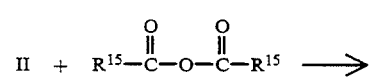

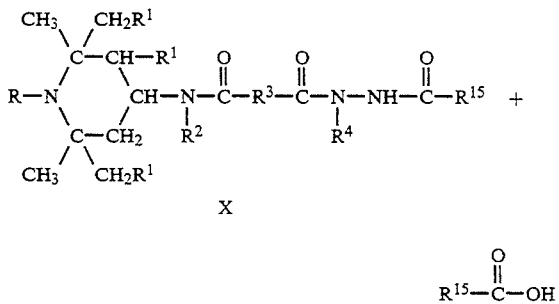

X

The reactions are typically conducted in aprotic solvents, such as THF, diethyl ether or t-butyl methyl ether. However, the reaction may also be carried out by adding the anhydride to a methanolic solution of the hydrazide. R, $R^1$, $R^2$, $R^3$, $R^4$, $R^{15}$ and $R^{18}$ are as previously broadly defined. Preferably, $R^{15}$ is alkyl of 1–10 carbons or phenyl. In addition, when R is hydrogen, alkyl, cycloalkyl, aralkyl or aryl, the carboxylic acid generated in the reaction may form a salt, designated as Formula XA, with the hindered amine of Formula X, as per the following equation:

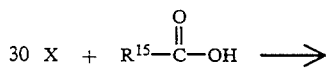

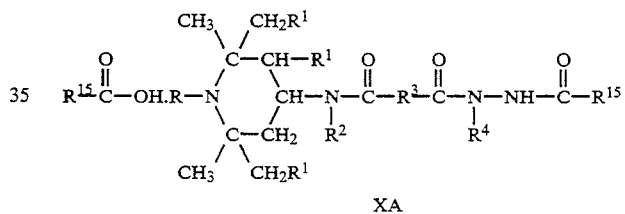

XA

The free base acyl derivatives of Formula X may be regenerated from the carboxylic acid salt of Formula XA by neutralizing the salt with a stronger base than the hindered amine, for example, dilute sodium hydroxide, dilute potassium hydroxide, hydrazine or more basic amines, such as diethylamine and triethylamine. This neutralization procedure is illustrated by the following equation:

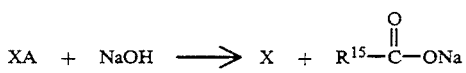

Acyl derivatives, designated as Formula XB where $R^3$ is a direct bond may also be prepared by reacting acid hydrazides with oxalate diesters to form the intermediate of Formula XI which is then reacted with 4-amino-2,2,6,6-tetraalkylpiperidines, as indicated in the following reaction equations:

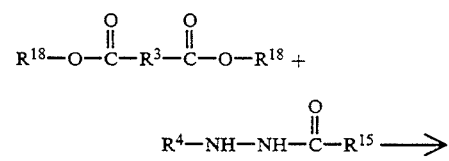

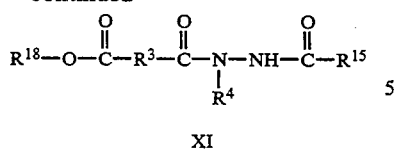

XI

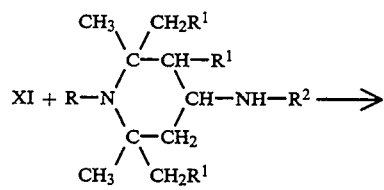

XB

R, $R^1$, $R^2$, $R^4$, $R^{15}$ and $R^{18}$ are as previously defined and $R^3$ is a direct bond.

The corresponding diacyl derivatives of starting Formula II, designated as Formula XII, can be prepared by reacting the amic acid esters of Formula IV with diacid dihydrazides in a 2:1 mole ratio neat or in refluxing alcohols, such as methanol, ethanol or isopropanol, as indicated in the following reaction equation:

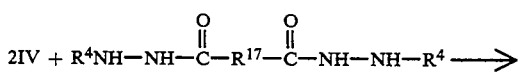

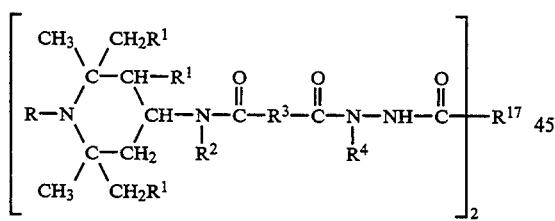

XII

For the preparation of the novel diacyl derivatives of Formula XII, R, $R^1$, $R^2$, $R^3$, $R^4$, $R^{15}$, $R^{17}$ and $R^{18}$ are as previously defined.

The novel alkoxycarbonyl, cycloalkoxycarbonyl, aryloxycarbonyl and aralkoxycarbonyl derivatives of starting materials of Formula II, designated as Formula XIII, may be prepared by reacting the N-(2,2,6,6-tetraalkyl-4-piperidinyl)amic acid esters of Formula IV with the corresponding alkyl, cycloalkyl, aryl or aralkyl carbazates in refluxing methanol, per the following equation:

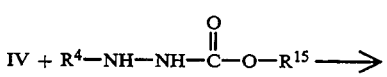

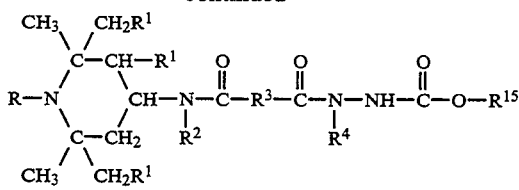

R, $R^1$, $R^2$, $R^3$, $R^4$ and $R^{15}$ are as previously broadly defined.

Alkoxycarbonyl, cycloalkoxycarbonyl, aryloxycarbonyl and aralkoxycarbonyl derivatives of Formula XIIIA where $R^3$ is a direct bond may also be prepared by reacting alkyl, cycloalkyl, aryl or aralkyl carbazates with oxalate diesters to form the intermediate of Formula XIV which is then reacted with 4-amino-2,2,6,6-tetraalkylpiperidines, per the following equations:

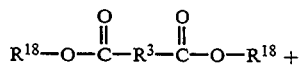

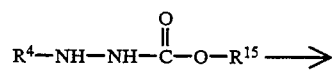

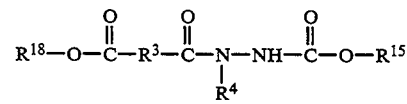

XIV

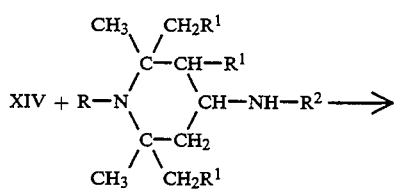

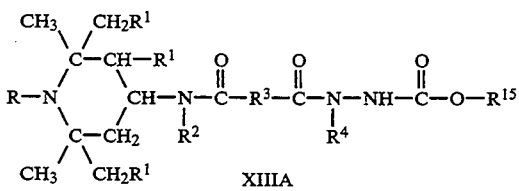

XIIIA

For the preparation of Formula XIIIA, R, $R^1$, $R^2$, $R^4$, $R^{15}$ and $R^{18}$ are as previously defined and $R^3$ is a direct bond.

The novel aryloxycarbonyl derivatives of II, designated as Formula XV, may also be prepared by reacting the hydrazides II with diaryl carbonates, per the following equation:

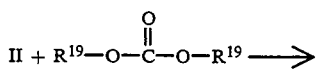

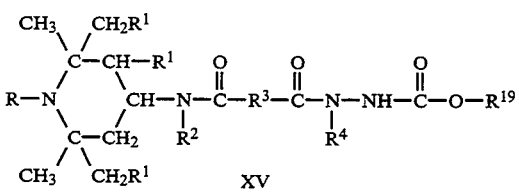

XV

R, $R^1$, $R^2$, $R^3$ and $R^4$ are as previously broadly defined and $R^{19}$ is substituted or unsubstituted aryl of 6–12 carbons.

The novel dialkoxycarbonyl, dicycloalkoxycarbonyl, diaryloxycarbonyl and diaralkoxycarbonyl derivatives of Formula II, designated as Formula XVI, may be prepared by reacting the amic acid esters of Formula IV with the corresponding bis-carbazates, per the following equation:

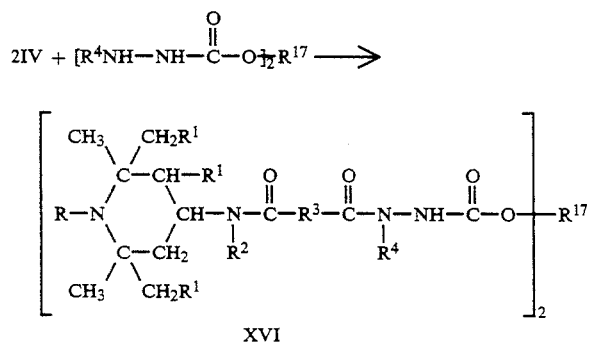

R, $R^1$, $R^2$, $R^3$, $R^4$, $R^{15}$, $R^{17}$ and $R^{18}$ are as previously defined, unless otherwise specified.

Sulfonyl derivatives of II, designated as Formulas XVII and XVIII, may be prepared by reacting the amic acid esters of Formula IV with the corresponding sulfonyl hydrazides or bis sulfonyl dihydrazides, respectively, per the following equations:

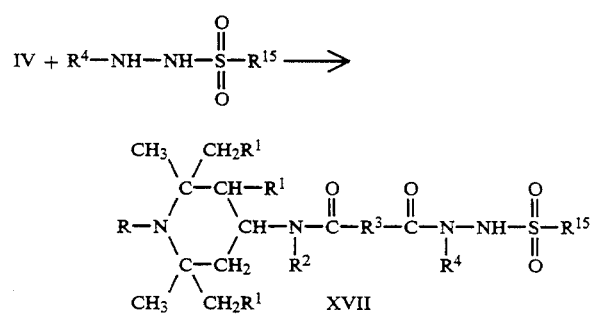

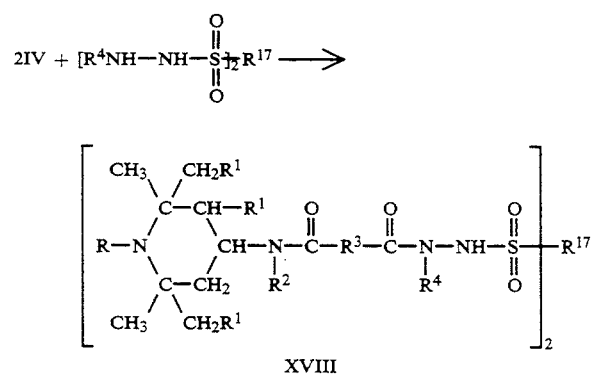

For the preparation of the novel sulfonyl derivatives of Formulas XVII and XVIII, R, $R^1$, $R^2$, $R^3$, $R^4$, $R^{15}$, $R^{17}$ and $R^{18}$ are as previously broadly defined, unless otherwise specified.

The novel sulfonyl derivatives of Formula XVIIA where $R^3$ is a direct bond also may be prepared by reacting sulfonyl hydrazides with oxalate diesters to form the intermediate of Formula XIX which is then reacted with 4-amino-2,2,6,6-tetralkylpiperidines, per the following equations:

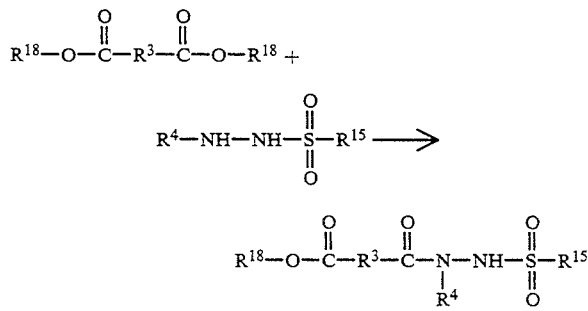

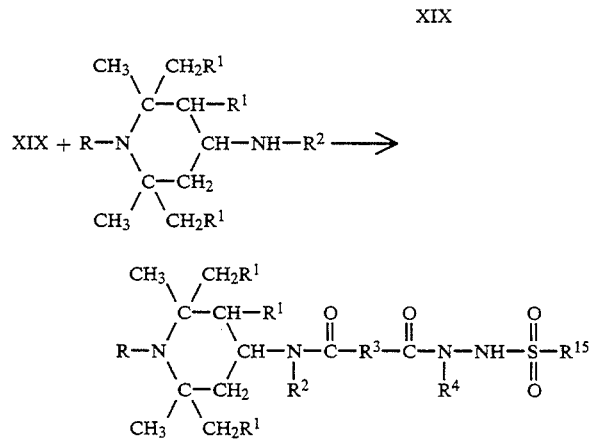

R, $R^1$, $R^2$, $R^4$, $R^{15}$ and $R^{18}$ are as previously defined and $R^3$ is a direct bond.

The novel 2-hydroxyalkyl derivatives of Formula II, designated as Formulas XX and XXI, may be prepared by reacting the hydrazides of Formula II with epoxides. The reactions are generally carried out neat or in a minimum amount of a high boiling solvent, such as dimethylformamide (DMF), dimethylacetamide (DMAC), xylene or mesitylene, for example. Reaction generally occurs quite readily at 140°–150° C. Illustrative reaction equations are as follows:

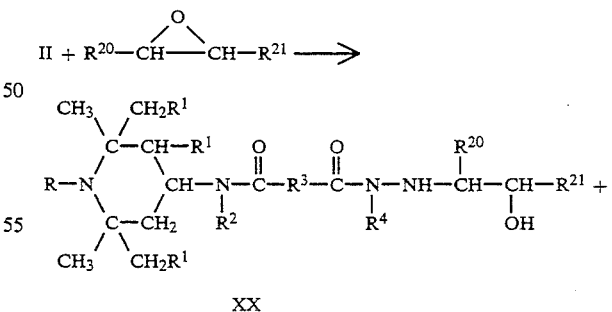

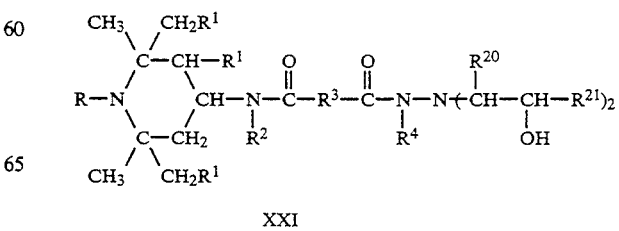

R, $R^1$, $R^2$, $R^3$ and $R^4$ are as previously broadly defined and $R^{20}$ and $R^{21}$ are independently hydrogen, alkyl of 1–20 carbons, cycloalkyl of 5–12 carbons, aryl of 6–12 carbons, aralkyl of 7–20 carbons, alkoxy of 1–20 carbons, cycloalkoxy of 5–12 carbons, aryloxy of 6–14 carbons, aralkoxy of 7–15 carbons, aliphatic acyloxy of 2–20 carbons, cycloaliphatic acyloxy of 6–13 carbons, aryl acyloxy of 7–15 carbons, araliphatic acyloxy of 8–16 carbons and in addition, $R^{20}$ and $R^{21}$ may be linked together to form an alicyclic ring of 5–12 carbons and any alkyl or cycloalkyl group may contain isolated double bonds.

If R is H, a third reaction product, XXII, is obtained:

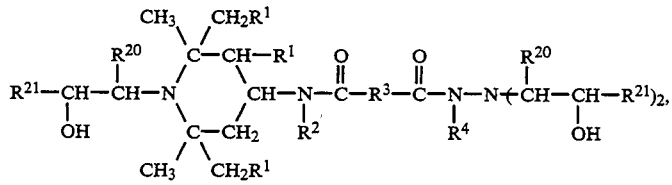

XXII

R is H and $R^1$, $R^2$, $R^3$, $R^4$, $R^{20}$ and $R^{21}$ are as previously broadly defined.

As indicated, the hydrazide group reacts with two equivalents of epoxide and if the piperidinyl amino group is not substituted, the hindered amino group will also react with the epoxide to give a trialkylated product. The ratio of the unsubstituted hydrazide of Formula II to the mono-, di- and trialkylated products is dependent upon the mole ratio of epoxide to hydrazide of Formula II, the temperature and the concentration if the reaction is run in a solvent.

The novel aliphatic, alicyclic, araliphatic and aryl derivatives of Formula II, designated as Formula XXIII, may be prepared by reacting esters of N-(2,2,6,6-tetraalkyl-4-piperdinyl)amic acids of Formula IV with monosubstituted hydrazines ($R^{13}NHNH_2$), 1,1-disubstituted hydrazines ($R^{13}R^{14}NNH_2$), 1,1,2-trisubstituted hydrazines ($R^{13}R^{14}NNR^4H$) and 1,2-disubstituted hydrazines ($R^4NHNHR^{14}$) per the following equation:

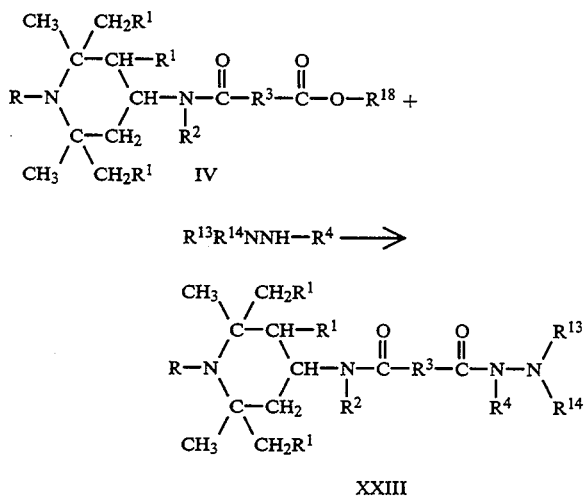

XXIII

R, $R^1$, $R^2$, $R^3$, $R^4$, $R^{13}$, $R^{14}$ and $R^{18}$ are as previously broadly defined.

The novel aliphatic, alicyclic, araliphatic and aryl derivatives XXIIIA where $R^3$ is a direct bond may be prepared by reacting oxalate diesters with the above-indicated hydrazines to form the intermediate XXIV which is then reacted with 4-amino-2,2,6,6-tetraalkylpiperidines, per the following equations:

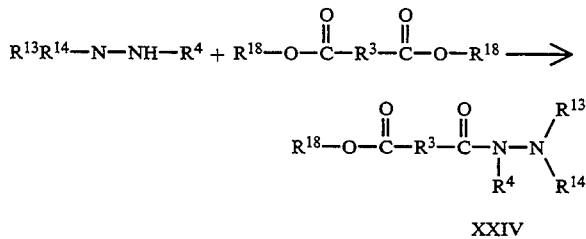

XXIV

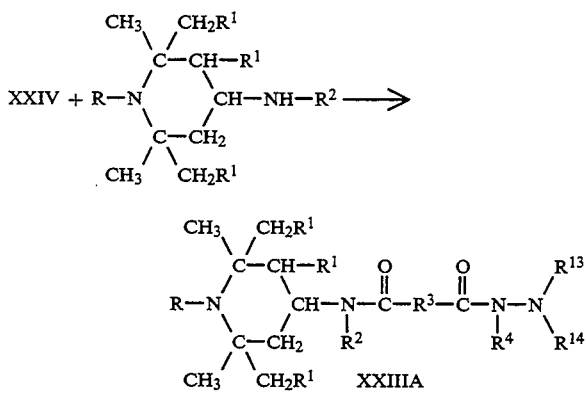

XXIIIA

R, $R^1$, $R^2$, $R^4$, $R^{13}$, $R^{14}$ and $R^{18}$ are as previously defined and $R^3$ is a direct bond.

The reactions to prepare the novel aliphatic, alicyclic, araliphatic and aryl derivatives, Formulas XXIII and XXIIIA, are run in polar solvents using equivalent amounts or a slight excess of the desired hydrazine. Depending upon $R^3$, the reaction may proceed at room temperature or may require refluxing. Preferably, the hydrazinolysis reaction is carried out in methanol or ethanol at about 10° C. to about 30° C. if $R^3$ is a direct bond and at reflux if $R^3$ is not a direct bond.

The following lists of compounds are to provide specific, but non-limiting, examples of the various types of starting or intermediate compounds which can be used in the foregoing illustrative preparative methods.

Non-limiting examples of suitable ketones include acetone, methyl ethyl ketone, 2-pentanone, 2-hexanone, 3-hexanone, 2-decanone, 3-methyl-2-pentanone, 4-methyl-2-pentanone, 4-methoxy-4-methyl-2-pentanone, cyclopentanone, cyclohexanone, cyclooctanone, 2,6-dimethyl-4-heptanone, 3,5-dimethyl-4-heptanone, 2,4-dimethyl-3-pentanone, 1,3-diphenylacetone, 2-octanone, 3-octanone, dihydroisophorone, 4-t-butylcyclohexanone, methylcyclohexyl ketone, acetophenone, 4-piperidone, 2,2,6,6-tetramethyl-4-piperidone and 2,6-diethyl-2,3,6-trimethyl-4-piperidone.

Non-limiting examples of suitable aldehydes include formaldehyde, acetaldehyde, butyraldehyde, dodecyl aldehyde, 2-ethylbutyraldehyde, heptaldehye, isobutyraldehyde, isovaleraldehyde, octyl aldehyde, propionaldehyde, valeraldehyde, benzaldehyde, 3,5-di-t-butyl-4-hydroxybenzaldehyde, 2,3-dimethyl-p-anisaldehyde, 3-hydroxybenzaldehyde, 1-naphthaldehyde, salicylaldehyde, p-tolualdehyde and 2,3,4-trimethoxybenzaldehyde.

Non-limiting examples of suitable isocyanates include allyl, benzyl, n-butyl, sec-butyl, isobutyl, t-butyl, cyclohexyl, ethyl, isopropyl, 4-methoxyphenyl, methyl, octadecyl, 1-naphthyl, phenyl, o-, m- and p-tolyl and dimethyl-m-isopropenylbenzyl isocyanates and 2-isocyanatoethyl methacrylate.

Non-limiting examples of suitable isothiocyanates include allyl, benzyl, 4-bromophenyl, n-butyl, sec-butyl, isobutyl, t-butyl, 3-chlorophenyl, cyclohexyl, ethyl, methyl, propyl, isopropyl, 2-naphthyl, t-octyl, phenethyl, phenyl, propyl, o- and p-tolyl isothiocyanates.

Non-limiting examples of suitable diisocyanates include ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3 and 1,4-diisocyanate and mixtures thereof, 1-isocyanato-3,3,5-trimethyl-5-isocyanatomethylcyclohexane(isophorone diisocyanate), 2,4- and 2,6-hexahydrotolylene diisocyanate and mixtures thereof, hexahydro-1,3 and/or 1,4-phenylene diisocyanate, perhydro-2,4' and/or 4,4'-diphenylmethane diisocyanate, 1,3- and 1,4-phenylene diisocyanate, 2,4- and 2,6-tolylene diisocyanate and mixtures thereof, diphenylmethane-2,4'- and/or 4,4'-diisocyanate, naphthylene 1,5-diisocyanate, m- and p-tetramethylxylene diisocyanate, 2,2,4-trimethylhexamethylene diisocyanate and 2,4,4-trimethylhexamethylene diisocyanate.

Non-limiting examples of suitable diisothiocyanates include ethylene diisothiocyanate, 1,4-tetramethylene diisothiocyanate, 1,6-hexamethylene diisothiocyanate, 1,4-diisothiocyanatobenzene, 1,1'-methylenebis[4-isothiocyanatocyclohexane] and 1,1'-oxybis[4-isothiocyanatobenzene].

Non-limiting examples of suitable amic acid esters include methyl, ethyl, propyl, isopropyl, n-butyl and phenyl oxamates and succinamates, ethyl and methyl N-(2,2,6,6-tetramethyl-4-piperidinyl)oxamate, ethyl and methyl N-(2,2,6,6-tetramethyl-4-piperidinyl)succinamate, ethyl and methyl N-(3,5-di-t-butyl-4-hydroxyphenyl)oxamate and ethyl and methyl N-(3,5-di-t-butyl-4-hydroxyphenyl)succinamate.

Non-limiting examples of suitable acid hydrazides include acetyl, propionic, butyric, isobutyric, valeric, isovaleric, caproic, heptanoic, caprylic, decanoic, lauric, myristic, palmitic and stearic hydrazides, benzhydrazide, 3,5-di-t-butyl-4-hydroxybenzhydrazide, 3-(3,5-di-t-butyl-4-hydroxyphenyl)propionic acid hydrazide, 3-n-hexylthiopropionic acid hydrazide, (4-benzoyl-3-hydroxyphenoxy)acetyl hydrazide and 3-(dimethylaminoethylthio)propionic acid hydrazide.

Non-limiting examples of suitable diacid dihydrazides include succinic acid dihydrazide, adipic acid dihydrazide, sebacic acid dihydrazide, azelaic acid dihydrazide, dodecanedioic acid dihydrazide and 1,3- and 1,4-benzenedicarboxylic acid dihydrazide.

Non-limiting examples of suitable carbazates include ethyl, methyl, propyl, isopropyl, butyl, allyl, methallyl, cyclohexyl, cyclopentyl, cyclododecyl, phenyl, benzyl, 4-t-butylcyclohexyl, 2-ethylhexyl, 4-methylphenyl, 3-methoxyphenyl, 2-acryloyloxyethyl,2-methacryloyloxyethyl, 2-(3-hydroxy-4-benzotriazol-2-ylphenoxy)ethyl, 2-(3-hydroxy-4-benzoylphenoxy)ethyl, 3-(3,5-di-t-butyl-4-hydroxyphenyl)propyl, 2-(3,5-di-t-butyl-4-hydroxyphenyl)ethyl, 2-[3-(3,5-di-t-butyl-4-hydroxyphenyl)propionyloxy]ethyl, 1-acetyl-2,2,6,6-tetramethyl-4-piperidinyl, 2,2,6,6-tetramethyl-4-piperidinyl and 1,2,2,6,6-pentamethyl-4-piperidinyl carbazates.

Non-limiting examples of suitable biscarbazates include ethylene biscarbazate, diethylene glycol biscarbazate, butane-1,4-diyl biscarbazate, butane-1,3-diyl biscarbazate, cycloheptane-1,2-diyl biscarbazate, cyclohexane-1,2-diyl biscarbazate, cyclohexane-1,4-diyl biscarbazate, decane-1,10-diyl biscarbazate, 2,2-diethylpropane-1,3-diyl biscarbazate, 2,2-dimethyl-1,3-diyl biscarbazate, hexane-1,6-diyl biscarbazate and propane-1,3-diyl biscarbazate.

Non-limiting examples of suitable diaryl carbonates include diphenyl, di-4-methylphenyl, di-2-methylphenyl, di-3-methylphenyl, di-3-methoxyphenyl, di-2,6-dimethylphenyl and di-2,5-di-t-butylphenyl carbonates.

Non-limiting examples of suitable sulfonyl hydrazides include benzenesulfonyl hydrazide, 4-bromobenzenesulfonyl hydrazide, 1-butanesulfonyl hydrazide, 4-t-butylbenzenesulfonyl hydrazide, p-toluenesulfonyl hydrazide, ethanesulfonyl hydrazide, methanesulfonyl hydrazide, 4-fluorobenzenesulfonyl hydrazide, 1-hexadecanesulfonyl hydrazide, isopropanesulfonyl hydrazide and 1-naphthalenesulfonyl hydrazide.

Non-limiting examples of suitable bis(sulfonyl hydrazides) include 1,3- and 1,4-benzene bis(sulfonyl hydrazide), 1,2-ethane bis(sulfonyl hydrazide), 1,4-butane bis(sulfonyl hydrazide), 1,1'-oxy bis(4-benzenesulfonyl hydrazide), 1,1'-methylene bis(4-benzenesulfonyl hydrazide) and 1,4-cyclohexane bis(sulfonyl hydrazide).

Non-limiting examples of suitable epoxides include 1,2-epoxybutane, 2,3-epoxybutane, 1,2-epoxycyclododecane, 1,2-epoxycyclohexane, 1,2-epoxyoctane, 1,2-epoxydecane, 1,2-epoxydodecane, 1,2-epoxyoctadecane, 1,2-epoxy-3-phenoxypropane, 2,3-epoxypropyl acrylate, 2,3-epoxypropyl methacrylate, 2,3-epoxypropyl-4-methoxyphenyl ether, glycidyl isopropyl ether, glycidyl n-hexyl ether, glycidyl dodecyl ether and glycidyl octadecyl ether.

Non-limiting examples of suitable substituted hydrazines include methyl, ethyl, propyl, isopropyl, butyl, sec-butyl, t-butyl, amyl, t-amyl, hexyl, heptyl, octyl, 2-ethylhexyl, cyclopentyl, cyclohexyl, cycloheptyl, cyclooctyl, cyclododecyl, 4-t-butylcyclohexyl, 2-methylcyclohexyl, benzyl, alpha-methylbenzyl, alpha,alpha-dimethylbenzyl, phenethyl, phenyl, 2-bromophenyl, 2-chlorophenyl, 1,1-dimethyl, 1,2-dimethyl, 1,1-diethyl, 1,2-diethyl, 1,1-diphenyl, 3-hydroxybenzyl, 2-hydroxyethyl, 2-methoxyphenyl, 4-methoxyphenyl, 1-methyl-1-phenyl, o-, m-, and p-tolyl hydrazines.

UTILITY

The novel stabilizers of the present invention are very effective additives for stabilizing polymeric compositions which are normally subject to thermal, oxidative or actinic light degradation. At times it may be beneficial to add extraneous additives which will act as synergists with the hindered amine light stabilizing groups of the present invention.

The novel stabilizers of this invention can be blended with various polymeric compositions in high concentrations to form masterbatches which can then be blended with additional polypher either of the same or different type.

The amount of stabilizer used to stabilize the polymeric composition will depend on the particular polymer system to be stabilized, the degree of stabilization desired and the presence of other stabilizers in the composition. Normally it is advisable to have about 0.01% to about 5% by weight of the 2,2,6,6-tetraalkylpiperidine moiety of the compounds of this invention present in the polymeric composition. An advantageous range is from about 0.05% to about 2% by weight of the 2,2,6,6-tetraalkylpiperidine portion of the molecule in the final composition. In most cases, 0.1% to about 1% by weight is sufficient.

Non-limiting examples of polymeric compositions which may be stabilized by these novel hindered amine light stabilizers include:

(1) Polyolefins such as high, low and linear low density polyethylenes, which may be optionally cross-linked, polypropylene, polyisobutylene, poly(methylbutene-1), polyacetylene and, in general, polyolefins derived from monomers having from 2 to about 10 carbon atoms, and mixtures thereof.

(2) Polyolefins derived from diolefins, such as polybutadiene and polyisoprene.

(3) Copolymers of monoolefins or diolefins, such as ethylene-propylene, propylene-butene-1, propylene-isobutylene and ethylene-butene-1 copolymer.

(4) Terpolymers of ethylene and propylene with dienes (EPDM), such as butadiene, hexadiene, dicyclopentadiene and ethylidene norbornene.

(5) Copolymers of alpha-olefins with acrylic acid or methacrylic acids or their derivatives, such as ethylene-acrylic acid, ethylene-methacrylic acid and ethylene-ethyl acrylate copolymers.

(6) Styrenic polymers, such as polystyrene (PS) and poly(p-methylstyrene).

(7) Styrenic copolymers and terpolymers, such as styrene butadiene (SBR), styrene-allyl alcohol and styrene acrylonitrile (SAN), styrene-acrylonitrile-methacrylate terpolymer, styrene-butadiene-styrene block copolymers (SBS), rubber modified styrenics such as styrene-acrylonitrile copolymers modified with acrylic ester polymer (ASA), graft copolymers of styrene on rubbers, such as polybutadiene (HIPS), polyisoprene or styrene-butadiene-styrene block copolymers (Stereon TM products available from Firestone Synthetic Rubber and Latex Co.), graft copolymers of styrene-acrylonitrile on rubbers such as butadiene (ABS), polyisoprene or styrene-butadiene-styrene block copolymers, graft copolymers of styrene-methyl methacrylate on rubbers, such as polybutadiene (MBS), butadiene-styrene radial block copelymers (e.g., KRO 3 TM of Phillips Petroleum Co.), selectively hydrogenated butadiene-styrene block copolymers (e.g., Kraton G TM from Shell Chemical Co.) and mixtures thereof.

(8) Polymers and copolymers derived from halogen-containing vinyl monomers, such as poly (vinyl chloride), poly (vinyl fluoride), poly (vinylidene chloride), poly (vinylidene fluoride), poly(tetrafluoroethylene) (PTFE), vinyl chloride-vinyl acetate copolymers, vinylidene chloride vinyl acetate copolymers and ethylene tetrafluoroethylene copolymers.

(9) Halogenated rubbers, such as chlorinated and/or brominated butyl rubbers or polyolefins and fluoroelastomers.

(10) Polyphers and copolymers derived from alpha-, beta-unsaturated acids, anhydrides, esters, amides and nitriles or combinations thereof, such as polymers or copolymers of acrylic and methacrylic acids, alkyl and-/or glycidyl acrylates and methacrylates, acrylamide and methacrylamide, acrylonitrile, maleic anhydride, maleimide, the various anhydride containing polymers and copolymers described in this paragraph, copolymers of the polymers set forth in this paragraph and various blends and mixtures thereof, as well as rubber modified versions of the polymers and copolymers set forth in this paragraph.

(11) Polymers and copolymers derived from unsaturated alcohols or their acylated derivatives such as poly(vinyl alcohol), poly(vinyl acetate), poly(vinyl stearate), poly(vinyl benzoate), poly(vinyl maleate), poly(vinyl butyral), poly(allyl phthalate), poly(allyldiethylene glycol carbonate) (ADC), ethylene-vinyl acetate copolymer and ethylenevinyl alcohol copolymers.

(12) Polymers and copolymers derived from unsaturated amines such as poly(allyl melamine).

(13) Polymers and copolymers derived from epoxides, such as polyethylene oxide, polypropylene oxide and copolymers thereof as well as polymers derived from bis-glycidyl ethers.

(14) Poly(phenylene oxides), poly(phenylene ethers) and modifications thereof containing grafted polystyrene or rubbers, as well as their various blends with polystyrene, rubber modified polystyrenes or nylon.

(15) Polycarbonates and especially the aromatic polycarbonates, such as those derived from phosgene and bisphenols such as bisphenol-A, tetrabromobisphenol-A and tetramethylbisphenol-A.

(16) Polyesters derived from dicarboxylic acids and diols and/or hydroxycarboxylic acids or their corresponding lactones, such as polyalkylene phthalates (e.g., polyethylene terephthalate (PET), polybutylene terephthalate (PBT), and poly (1,4-dimethylcyclohexane terephthalate), or copolymers thereof and polylactones such as polycaprolactone.

(17) Polyarylates derived from bisphenols (e.g., bisphenol-A) and various aromatic acids, such as isophthalic and terephthalic acids or mixtures thereof.

(18) Aromatic copolyester carbonates having carbonate, as well as ester linkages present in the backbone of the polymers, such as those derived from bisphenols, iso- and terephthaloyl chlorides and phosgene.

(19) Polyurethanes and polyureas.

(20) Polyacetals, such as polyoxymethylenes and polyoxymethylenes which contain ethylene oxide as a comonomer.

(21) Polysulfones, polyethersulfones and polyimide-sulfones.

(22) Polyamides and copolyamides which are derived from diamines and dicarboxylic acids and/or from aminocarboxylic acids or the corresponding lactones, such as the following nylons: 6, 6/6, 6/10, 11 and 12.

(23) Polyimides, polyetherimides, polyamideimides and copolyetheresters.

(24) Cross-linked polymers which are derived from aldehydes on the one hand and from phenols, ureas and melamine on the other hand, such as phenol-formaldehyde, urea-formaldehyde and melamine-formaldehyde resins.

(25) Alkyl resins, such as glycerolphthalic acid resins and mixtures thereof with melamine-formaldehyde resins.

(26) Blends of vinyl monomers and unsaturated polyester resins which are derived from copolyesters of saturated and unsaturated dicarboxylic acids with polyhydric alcohols, as well as from vinyl compounds (crosslinking agents) and also halogen-containing, flame resistant modifications thereof.

(27) Natural polymers, such as cellulose and natural rubber, as well as the chemically modified homologous derivatives thereof, such as cellulose acetates, cellulose propionate, cellulose butyrate and the cellulose ethers such as methyl and ethyl cellulose.

In addition, the novel stabilizers of this invention may be used to stabilize various combinations or blends of the above polymers or copolymers. They are particularly useful in the stabilization of polyolefins, acrylic coatings, styrenics, rubber modified styrenics, poly(phenylene oxides) and their various blends with styrenics, rubber modified styrenics or nylon.

The novel hindered amine light stabilizers of this invention can be used together with other additives to further enhance the properties of the finished polymer. Examples of other additives that can be used in conjunction with the stabilizers of this invention include antioxidants, such as alkylated monophenols, alkylated hydroquinones, hydroxylated thiodiphenyl ethers, alkylidene-bisphenols, hindered phenolic benzyl compounds, acylaminophenols, esters of 3-(3,5-di-t-butyl-4-hydroxyphenyl)propionic acid, esters of 3-(5-t-butyl-4-hydroxy-3-methylphenyl)propionic acid, 3-(3,5-di-t-butyl-4-hydroxyphenyl)propionic acid amides; UV absorbers and light stabilizers such as 2-(2'-hydroxyphenyl)-2H-benzotriazoles, 2-hydroxy benzophenones, benzylidene malonate esters, esters of substituted or unsubstituted benzoic acids, diphenyl acrylates, nickel chelates, oxalic acid diamides, other hindered amine light stabilizers, other additives such as metal deactivators, phosphites and phosphonites, peroxide decomposers, fillers and reinforcing agents, plasticizers, lubricants, corrosion and rust inhibitors, emulsifiers, mold release agents, carbon black, pigments, fluorescent brighteners, both organic and inorganic flame retardants and non-dripping agents, melt flow improvers and antistatic agents. Numerous examples of suitable additives of the above type are given in Canadian Patent 1,190,038.

A presently preferred additive is 2,4-di-t-butylphenyl 3,5-di-t-butyl-4-hydroxybenzoate preferably added in an amount of about 0.01% to about 1.0% by weight of the composition to which it is added.

The following examples are presented to provide a more detailed explanation of the present invention and are intended as illustrations and not limitations of the invention.

EXAMPLES

Starting Materials

Ethyl N-(2,2,6,6-tetramethyl-4-piperidinyl)oxamate was prepared by reacting 4-amino-2,2,6,6-tetramethylpiperidine with an excess of diethyl oxalate and subsequently stripping off the excess diethyl oxalate.

Methyl N-(2,2,6,6-tetramethyl-4-piperidinyl)oxamate was formed by ester exchange wherein the above ethyl ester was dissolved in methanol and allowed to stand at room temperature for a minimum of 24 hours.

HALS-O

N-(2,2,6,6-tetramethyl-4-piperidinyl)-N'-aminooxamide was prepared by the hydrazinolysis of methyl or ethyl N-(2,2,6,6-tetramethyl-4-piperidinyl)oxamate with 85% hydrazine hydrate in methanol.

HALS-2

N-(2,2,6,6-tetramethyl-4-piperidinyl)-N'-aminosuccinamide was prepared by the reaction of 4-amino-2,2,6,6-tetramethylpiperidine with ethyl succinyl chloride followed by hydrazinolysis of the resulting ester with 85% hydrazine hydrate in methanol.

HALS-4

N-(2,2,6,6-tetramethyl-4-piperidinyl)-N'-aminoadipamide was prepared by reacting 4-amino-2,2,6,6-tetramethylpiperidine with ethyl adipoyl chloride, followed by hydrazinolysis of the resulting ester with 85% hydrazine hydrate in methanol.

HALS-5

4-Hydrazinocarbonyl-1-(2,2,6,6-tetramethyl-4-piperidinyl)-2-pyrrolidone was prepared by the hydrazinolysis of 4-(methoxycarbonyl)-1-(2,2,6,6-tetramethyl-4-piperidinyl)-2-pyrrolidone with excess hydrazine hydrate in methanol. The above intermediate half ester was prepared by the addition of 4-amino-2,2,6,6-tetramethylpiperidine to dimethyl itaconate according to the procedure described in U.S. Pat. No. 4,309,546.

3-(3,5-Di-t-butyl-4-hydroxyphenyl)propionhydrazide was prepared by the hydrazinolysis of ethyl 3-(3,5-di-t-butyl-4-hydroxyphenyl)propionate in methanol.

3,5-Di-t-butyl-4-hydroxybenzhydrazide was prepared by the hydrazinolysis of 2,4-di-t-butylphenyl-3,5-di-t-butyl-4-hydroxybenzoate (UV Chek AM 340—a product of Ferro Corp.) in methanol.

N-(3,5-di-t-butyl-4-hydroxyphenyl)-N'-aminooxamide was prepared by reacting 3,5-di-t-butyl-4-hydroxyaniline with ethyl oxalyl chloride followed by hydrazinolysis of the resulting ester with 85% hydrazine hydrate in methanol.

(4-Benzoyl-3-hydroxyphenoxy)acetylhydrazide was prepared by reacting 2,4-dihydroxybenzophenone with ethyl chloroacetate in the presence of potassium carbonate. The resulting ester was converted to the hydrazide by hydrazinolysis with 85% hydrazine hydrate in methanol.

m-Tetramethylxylene diisocyanate (TMXDI) and m-isopropenyl-alpha,alpha-dimethylbenzyl isocyanate (TMI) were obtained from American Cyanamid Company.

Isophorone diisocyanate was obtained from Nuodex, a division of Huls America, Inc.

Irganox TM 1076 [octadecyl 3-(3,5-di-t-butyl-4-hydroxyphenyl)propionate], Tinuvin TM 770 (di-2,2,6,6-tetramethyl-4-piperidinyl sebacate) and Chimasorb TM 944 [(N,N'-bis(2,2,6,6-tetramethyl-4-piperidinyl)-1,6-hexane-diamine, polymer with 2,4,6-trichloro-1,3,5-triazine and 2,4,4-trimethyl-1,2-pentanamine] were obtained from Ciba Geigy Corporation.

UV-Chek TM AM-340 (2,4-di-t-butylphenyl 3,5-di-t-butyl-4-hydroxybenzoate) was obtained from the Chemical Division of Ferro Corporation.

Benzenesulfonyl hydrazide was obtained from Canada Colors and Chemicals Limited.

Butyric, isobutyric, valeric, caproic, heptanoic, caprylic, decanoic, lauric, myristic and stearic hydrazides were prepared by the hydrazinolysis of the corresponding methyl esters with hydrazine hydrate. The methyl esters were purchased from Aldrich Chemical Co.

n-Butyl isocyanate, 1,6-hexamethylene diisocyanate, octadecyl isocyanate, phenyl isocyanate, tolylene 2,4- diisocyanate, n-butyl isothiocyanate, cyclohexanone, ethyl carbazate, 2-ethylhexyl glycidyl ether, 1,2-epoxy-3-phenoxypropane, methylhydrazine, 3,5-di-t-butyl-4-hydroxybenzaldehyde, acetic hydrazide, adipic dihydrazide, benzoic hydrazide, salicylic hydrazide, propionic, butyric, valeric, hexanoic and heptanoic anhydrides and 2,2,6,6-tetramethyl-4-piperidone hydrochloride were purchased from Aldrich Chemical Company, Inc.

EXAMPLE I

Preparation of the n-Butyl Isothiocyanate Adduct of N-(2,2,6,6-tetramethyl-4-piperidinyl)-N'-aminooxamide

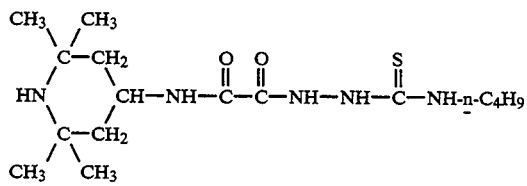

To a slurry of N-(2,2,6,6-tetramethyl-4-piperidinyl)-N'-aminooxamide (12.2 g, 0.05 mole) (HALS-O) in 200 mls of tetrahydrofuran (THF) was added dropwise n-butyl isothiocyanate (5.8 g, 0.05 mole) over several minutes. There was no observable exotherm. The reaction was stirred ½ hour at room temperature and then heated to reflux for 45 minutes. A homogeneous solution was obtained when the reaction temperature reached 50° C. After cooling to room temperature, the reaction mixture was filtered. The filter cake was air dried overnight and weighed 16.6 grams. The product melted from 170°–181° C. A liquid chromatography scan showed the presence of only one component. An infrared (IR) scan (nujol mull) contained strong sharp carbonyl bands at 1668 and 1604 cm$^{-1}$. The IR scan was consistent with the structure of the desired product.

EXAMPLES II–XIV

Preparation of Isocyanate and Diisocyanate Adducts of N-(2,2,6,6-tetramethyl-4-piperidinyl)amic Acid Hydrazides

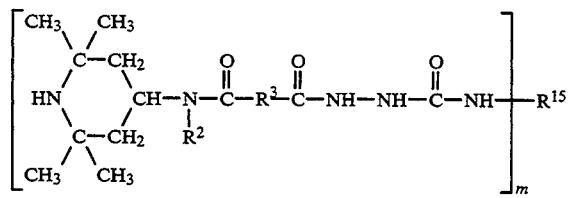

The isocyanate and diisocyanate adducts were prepared by adding equal equivalents of the isocyanate or diisocyanate indicated in Table I to a stirring slurry of the N-(2,2,6,6-tetramethyl-4-piperidinyl)amic acid hydrazide in THF. The addition was typically started at room temperature and the temperature was allowed to rise throughout the addition (5–10 minutes). The reaction was stirred an additional hour, after which the reaction was usually complete. To assure complete reaction of the isocyanate, the reaction mixtures were heated to reflux and refluxed 1 to 2½ hours in some examples. If the product was insoluble in THF, it was isolated by filtration and air dried. If the product was soluble in THF, it was isolated by evaporating the solvent on a rotating evaporator under reduced pressure. The residue was pulverized with a mortar and pestle and air dried overnight.

The products were characterized by their melting ranges and infrared spectra. The infrared spectra were run in solution or as nujol mulls.

Example IX was prepared using methyl ethyl ketone as the solvent instead of THF.

Information including reactants, reaction parameters, structures of products and results are summarized in Table I.

TABLE I

ISOCYANATE AND DIISOCYANATE ADDUCTS OF HALS AMIC ACID HYDRAZIDES

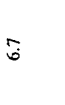

| EXAMPLE # | m | R15 | R2 | R3 | HALS HYDRAZIDE | GRAMS | ISOCYANATES OR DIISOCYANATES | GRAMS | REACTION TEMP, °C. | REFLUX TIME | ISOLATION METHOD | YIELD (GRAMS) | MELTING RANGE °C. | INFRARED CARBONYL BANDS cm−1 |
|---|---|---|---|---|---|---|---|---|---|---|---|---|---|---|
| II | 1 | C6H5 | H | DIRECT BOND | HALS-0 | 24.8 | PHENYL ISOCYANATE | 11.9 | 20-37 | — | FILT. | 39.7 | 213-218 | 1670,1590,1550(NUJOL) |
| III | 1 | n-C4H9 | H | DIRECT BOND | HALS-0 | 24.8 | n-BUTYL ISOCYANATE | 9.9 | 19-28 | 2½ hrs | FILT. | 34.2 | 159-161 | 1655,1620,1500(NUJOL) |
| IV | 1 | C18H37 | H | DIRECT BOND | HALS-0 | 12.4 | OCTADECYL ISOCYANATE | 14.8 | 22-35 | — | EVAP. | 24.6 | 92-94 | 1660,1590,1500(CHCl3) |
| V | 1 | n-C4H9 | H | —(CH2)2— | HALS-2 | 6.75 | n-BUTYL ISOCYANATE | 2.5 | 22-25 | 2½ hrs | EVAP. | 8.2 | | 1655,1540 (CHCl3) |
| VI | 1 | n-C4H9 | H | —(CH2)4— | HALS-4 | 6.7 | n-BUTYL ISOCYANATE | 2.2 | 22-25 | 1½ hrs | EVAP. | 8.4 | | 1635,1540 (CHCl3) |
| VII | 1 | n-C4H9 | H | —CH2—CH—CH2— | HALS-5 | 7.1 | n-BUTYL ISOCYANATE | 2.5 | 22-27 | 1 hr | FILT. | 7.1 | 179-182 | 1655,1545 (NUJOL) |
| VIII | 1 | C18H37 | " | | HALS-5 | 7.1 | OCTADECYL ISOCYANATE | 7.4 | 22-27 | 1 hr | EVAP. | 12.8 | 68-70 | 1655,1550 (NUJOL) |
| IX | 2 | 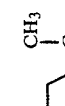 | H | DIRECT BOND | HALS-0 | 14.8 | TOLYLENE 2,4-DIISOCYANATE | 5.2 | 22-25 | — | FILT. | 20.0 | 183-185 | 1650,1590,1510(NUJOL) |
| X | 2 | | H | DIRECT BOND | HALS-0 | 24.8 | ISOPHORONE DIISOCYANATE | 11.1 | 23-37 | 1 hr | FILT. | 35.7 | 185-195 | 1645,1580,1500(NUJOL) |
| XI | 2 | | H | DIRECT BOND | HALS-0 | 18.2 | TMXD | 9.15 | 45-49 | — | FILT. | 27.3 | 202-205 | 1665,1600,1570(NUJOL) |
| XII | 2 | —(CH2)6— | H | DIRECT BOND | HALS-0 | 24.8 | 1,6-HEXAMETHYLENE DIISOCYANATE | 8.6 | 23-28 | 2 hrs | FILT. | 31.8 | 163-167 | 1655,1590,1500(NUJOL) |

TABLE I-continued

ISOCYANATE AND DIISOCYANATE ADDUCTS OF HALS AMIC ACID HYDRAZIDES $$\left[ \begin{array}{c} CH_3 \quad CH_3 \\ HN \underset{CH_3 \quad CH_3}{\diagdown} N-C-R^2-C-NH-NH-C-NH-R^{15} \\ \phantom{HN} \quad \underset{O}{\parallel} \quad \underset{O}{\parallel} \quad \underset{O}{\parallel} \end{array} \right]_m$$

| EXAMPLE # | m | R$^{15}$ | R$^2$ | R$^3$ | HALS HYDRAZIDE | GRAMS | ISOCYANATES OR DIISOCYANATES | GRAMS | REACTION TEMP. °C. | REFLUX TIME | ISOLATION METHOD | YIELD (GRAMS) | MELTING RANGE °C. | INFRARED CARBONYL BANDS cm$^{-1}$ |
|---|---|---|---|---|---|---|---|---|---|---|---|---|---|---|
| XIII | 2 | (trimethylcyclohexyl-CH$_2$–) | | –CH$_2$–CH– –CH$_2$ | HALS-5 | 8.5 | ISOPHORONE DIISOCYANATE | 3.35 | 22–29 | 1 hr | EVAP. | 11.3 | 210–215 | 1670,1545 (NUJOL) |
| XIV | 2 | –(CH$_2$)$_6$– | H | –CH$_2$–CH– –CH$_2$ | HALS-5 | 14.1 | 1,6-HEXAMETHYLENE DIISOCYANATE | 4.2 | 23–31 | 1 hr | EVAP. | 18.7 | 146–160 | 1660,1550,1490(CHCl$_3$) |

EXAMPLES XV–XX

Hydrazone Derivatives of N-(2,2,6,6-tetramethyl-4-piperidinyl)amic Acid Hydrazides

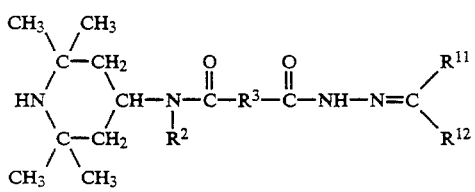

The hydrazone derivatives indicated in Table II were prepared by reacting equal equivalents (or a slight excess of ketone) of the HALS hydrazide with the ketone in toluene or xylene and azeotropically distilling off the water formed in the reaction. The reactions were refluxed using a reflux condenser connected to a Dean Stark trap, until water no longer formed in the trap. Insoluble products were isolated by filtration and soluble products were isolated by solvent evaporation on a rotating evaporator under reduced pressure. Product residues were generally pulverized, rinsed with a non-solvent or poor solvent to remove any residual starting material and air dried overnight.

The products were characterized by their melting ranges and infrared spectra. The infrared spectra were run in solution or as nujol mulls.

In Example XVIII, the free base of the 2,2,6,6-tetramethyl-4-piperidone hydrochloride salt (obtained from the Aldrich Chemical Co.) was liberated with aqueous caustic prior to running the reaction. The water from the caustic and the water generated by the reaction were removed by azeotropic distillation.

Information including reactants, reaction parameters, structures of products and the results are summarized in Table II.

TABLE II

HYDRAZONE DERIVATIVES OF HALS AMIC ACID HYDRAZIDES $$\text{structure: 2,2,6,6-tetramethylpiperidine-4-yl}-N(R^2)-C(O)-R^3-C(O)-NH-N=C(R^{11})(R^{12})$$

| EXAMPLE # | $R^2$ | $R^3$ | $=C(R^{11})(R^{12})$ | HALS HYDRAZIDE | GRAMS | ALDEHYDE OR KETONE | GRAMS | SOLVENT | AZEOTROPE PERIOD | ISOLATION METHOD | WASH SOLVENT | YIELD (GRAMS) | MELTING RANGE °C. | INFRARED CARBONYL BANDS cm$^{-1}$ |
|---|---|---|---|---|---|---|---|---|---|---|---|---|---|---|
| XV | H | DIRECT BOND | $=C(CH_3)_2$ | HALS-0 | 24.2 | ACETONE | 8.2 | TOLUENE | 16 hrs. | EVAP. | HEXANE | 26.3 | 122–124 | 1645,1495 (XYLENE) |
| XVI | H | DIRECT BOND | $=C(CH_3)(C_2H_5)$ | HALS-0 | 24.2 | METHYL ETHYL KETONE | 8.0 | XYLENE | 10 hrs. | EVAP. | — | 27.1 | | 1645,1495 (XYLENE) |
| XVII | H | DIRECT BOND | cyclohexylidene | HALS-0 | 24.2 | CYCLOHEXANONE | 9.8 | XYLENE | 2½ hrs. | EVAP. | METHYL t-BUTYL ETHER | 22.0 | 130–133 | 1655,1530 (NEAT) 1655,1545, 1500(NUJOL) |
| XVIII | H | DIRECT BOND | 2,2,6,6-tetramethylpiperidin-4-ylidene | HALS-0 | 12.7 | 2,2,6,6-TETRAMETHYL-4-PIPERIDONE | 7.8 | TOLUENE | 12 hrs. | FILT. | — | 9.6 | 203–205 | 1670,1490 (CHCl$_3$) |
| XIX | H | DIRECT BOND | 3,5-di-t-butyl-4-hydroxybenzylidene | HALS-0 | 12.7 | 2,5-Di-t-BUTYL-4-HYDROXY-BENZALDEHYDE | 11.8 | XYLENE | 2 hrs | FILT. | HEXANE | 19.9 | 142–150 | 1645,1590 1520(NUJOL) |
| XX | $-CH_2-CH-\atop \phantom{x}-CH_2-$ | | $=C(CH_3)(C_2H_5)$ | HALS-5 | 14.1 | METHYL ETHYL KETONE | 7.2 | XYLENE | 6½ hrs. | EVAP. | TETRAHYDROFURAN | 11.8 | 126–130 | 1675,1490 (NUJOL) |

EXAMPLE XXI

Preparation of
1-[N-(2,2,6,6-tetramethyl-4-piperidinyl)oxamoyl]-2-dodecanoylhydrazine

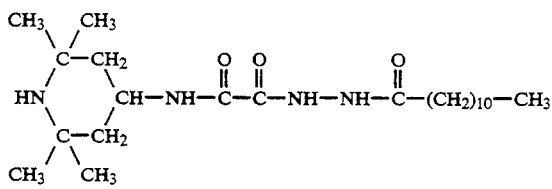

Into a 3-necked 300 ml flask was introduced a 60.9% solution of ethyl N-(2,2,6,6-tetramethyl-4-piperidinyl)oxamate in methanol (21.0 g, 0.05 mole), lauric acid hydrazide (13.5 g) and 150 ml of anhydrous methanol. The flask was equipped with a thermometer, a magnetic stirrer and a Dean Stark trap with a reflux condenser. The reaction mixture was heated to reflux and the methanol was slowly distilled off through the Dean Stark trap. The disappearance of the starting materials and the formation of the products were monitored by liquid chromatography. After 6 hours at reflux and the removal of 110 ml of methanol, the liquid chromatograph scans indicated the reaction was essentially complete.

The reaction mixture was filtered hot and the filtrate was stripped to dryness on a rotating evaporator under reduced pressure. The residue was a white powder weighing 16.6 g and had a melting range of 80°–84° C. An infrared scan (nujol mull) of the product contained strong carbonyl bands at 1655, 1580 and 1490 cm$^{-1}$.

A second crop of 2.35 g of product (melting range 88°–92° C.) was obtained by dissolving the filter cake in methanol, filtering off a small amount of insoluble material and stripping the filtrate to dryness.

EXAMPLE XXII

Preparation of
1-[N-(2,2,6,6-tetramethyl-4-piperidinyl)oxamoyl]-2-ethoxycarbonylhydrazine

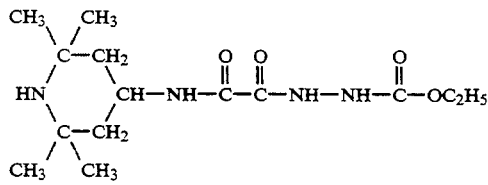

Into a 3-necked 250 ml flask was introduced a 60.9% solution of ethyl N-(2,2,6,6-tetramethyl-4-piperidinyl)oxamate in methanol (21.0 g, 0.05 mole), ethyl carbazate (5.2 g, 0.05 mole) and 100 ml of anhydrous methanol. The flask was equipped with a thermometer, a magnetic stirrer and a Dean Stark trap with a reflux condenser. The reaction mixture was heated to reflux and the methanol was slowly distilled off through the Dean Stark trap. After 5 hours at reflux and the removal of 75 ml of methanol, the reaction mixture partially solidified. The reaction mixture was diluted with 15 ml of methanol and filtered hot. The filtrate was stripped to dryness on a rotating evaporator under reduced pressure. The residue was a white powder weighing 8.4 g and had a melting range of 106°–109° C. A liquid chromatographic scan indicated the presence of one component. An infrared scan (nujol mull) of the product contained strong carbonyl bands at 1685 cm$^{-1}$ and 1590 cm$^{-1}$ and weak carbonyl bands at 1530 cm$^{-1}$ and 1485 cm$^{-1}$.

A second crop of 3.45 g of product (melting range 97°–100° C.) was obtained by dissolving the filter cake in methanol, filtering off a small amount of insoluble material and stripping the filtrate to dryness.

1-[N-(2,2,6,6-tetramethyl-4-piperidinyl)oxamoyl]-2-ethoxycarbonylhydrazine was also prepared in 75% yield by reacting equivalent amounts of 4-amino-2,2,6,6-tetramethylpiperidine and 1-ethoxalyl-2-ethoxycarbonylhydrazine (prepared from ethyl carbazate and ethyl oxalyl chloride) in methanol.

EXAMPLE XXIII

Preparation of
1,2-Di-[N-(2,2,6,6-tetramethyl-4-piperidinyl)oxamoyl]-hydrazine

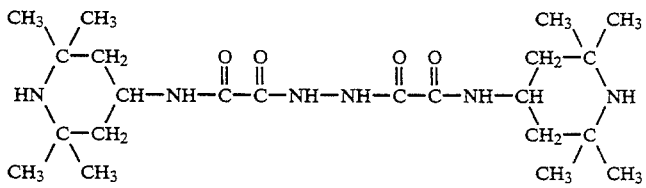

Into a 3 liter 3-necked flask was introduced N-(2,2,6,6-tetramethyl-4-piperidinyl)-N'-aminooxamide (HALS-O) (165 g, 0.68 mole) and 1600 ml methanol. The flask was equipped with a magnetic stirrer, a thermometer and a Dean Stark trap with a reflux condenser. The mixture was heated in an oil bath and upon warming to 50° C., the HALS-O was completely dissolved. To the warm solution was added a 60.9% solution of ethyl N-(2,2,6,6-tetramethyl-4-piperidinyl)oxamate (271 g, 0.644 mole). The solution was added dropwise over 15 minutes from a dropping funnel inserted in the center neck of the flask. The reaction mixture was still a clear solution at the end of the addition but upon heating to reflux, solid material began to form. The reaction mixture was refluxed for 4 hours while slowly removing about 750 ml of methanol by periodically draining the Dean Stark trap. At the end of the relux period, the 750 ml of methanol was added back to the reaction flask and the mixture was cooled to 50° C. and filtered. The filter cake was filtered semi-dry, washed with fresh methanol, pulled semi-dry and air dried on drying paper overnight. The product weighed 195 g and had a melting range of 298°–303° C.

A second crop of 31.5 g of product was obtained by cooling the methanol filtrate and refiltering it.

The infrared scan of the product contained strong, sharp carbonyl bands at 1655, 1580 and 1495 cm$^{-1}$.

EXAMPLE XXIV

Preparation of
1-[N-(2,2,6,6-tetramethyl-4-piperidinyl)oxamoyl]-2-[3-(3,5-di-t-butyl-4-hydroxyphenyl)propionyl]hydrazine

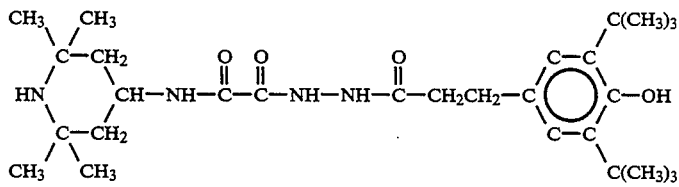

Into a 3-necked 100 ml flask was introduced methyl N-(2,2,6,6-tetramethyl-4-piperidinyl)oxamate (4.85 g, 0.02 mole) and 50 ml of methanol. The flask was equipped with a magnetic stirrer, a thermometer and a reflux condenser. The mixture was stirred until all of the solid material dissolved, following which 3-(3,5-di-t-butyl-4-hydroxyphenyl)propionhydrazide (5.85 g, 0.02 mole) was added and the mixture was refluxed for 2 hours. The solid material was filtered off and air dried. The product weighed 2.7 g and had a melting range of 255°-257° C. The infrared scan of the product contained strong carbonyl bands at 1655, 1620, 1590 and 1490 cm$^{-1}$.

A second crop of 2.5 g of product was obtained by concentrating the filtrate at the reflux temperature until solid material formed. The mixture was cooled, re-filtered and the isolated solid was air dried.

EXAMPLE XXV

Preparation of
1-[N-(2,2,6,6-tetramethyl-4-piperidinyl)oxamoyl]-2-[(3,5-di-t-butyl-4-hydroxy)benzoyl]hydrazine

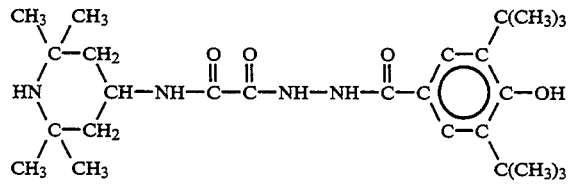

Into a 3-necked flask was introduced a 58% solution of methyl N-(2,2,6,6-tetramethyl-4-piperidinyl)oxamate in methanol (20.8 g, 0.05 mole) and 200 ml of additional anhydrous methanol. The flask was equipped with a magnetic stirrer, a thermometer and a Dean Stark trap with a relux condenser. The mixture was stirred and 3,5-di-t-butyl-4-hydroxybenzhydrazide (13.3 g, 0.05 mole) was added over about 5 minutes. A homogeneous solution was obtained. The reaction was heated to reflux in an oil bath and refluxed for 2½ hours. The methanol was then slowly distilled off by periodically draining the Dean Stark trap until solid material began to form. Approximately 50 ml of methanol was removed over 2½ hours. The reaction was cooled to room temperature and the solid material was filtered off and air dried. The product weighed 10.7 g and had a melting range of 178°-182° C.

An additional 10.3 g of product was obtained by concentrating the filtrate and refiltering. Both crops were combined, slurried in 125 ml of acetone, filtered and air dried. The product was a white powder which turned a light yellow color upon exposure to air. The combined product weighed 20.4 g and had a melting range of 184°-189° C. The infrared scan (nujol mull) of the product contained carbonyl peaks at 1635, 1590 and 1555 cm$^{-1}$.

EXAMPLE XXVI

Preparation of
1-[N-(2,2,6,6-tetramethyl-4-piperidinyl)oxamoyl]-2-stearoylhydrazine

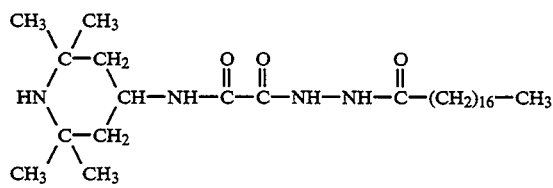

Into a 3-necked 500 ml flask was added a 55% solution of ethyl N-(2,2,6,6-tetramethyl-4-piperidinyl)oxamate (20.4 g, 0.044 mole) in anhydrous methanol and 300 ml of additional methanol. The flask was equipped with a magnetic stirrer, a thermometer and a Dean Stark trap with a reflux condenser. The mixture was stirred and stearic acid hydrazide (14.95 g, 0.05 mole) was added. The reaction was heated in an oil bath to reflux. The reaction was refluxed for 6 hours and 180 ml of methanol was distilled off by periodically draining the Dean Stark trap during the last hour. The hot reaction mixture was filtered to remove a small amount of unknown insoluble material. The solution was cooled to room temperature and was re-filtered to remove 1.1 g of stearic acid hydrazide. The filtrate was stripped to dryness on a rotating evaporator under reduced pressure. The residue was scraped out of the flask and pulverized into a white powder with a mortar and pestle. The product weighed 20.2 g and had a melting range of 78°-82° C. The infrared scan (nujol mull) of the product contained broad carbonyl bands at 1655, 1585 and 1495 cm$^{-1}$.

1-[N-(2,2,6,6-tetramethyl-4-piperidinyl)oxamoyl]-2-stearoylhydrazine was also prepared in 64% yield by reacting equivalent amounts of 4-amino-2,2,6,6-tetramethylpiperidine and 1-ethoxalyl-2-stearoylhydrazine (prepared from reacting stearic acid hydrazide with ethyl oxalyl chloride) in methanol.

EXAMPLE XXVII

Alkylation of
N-(2,2,6,6-tetramethyl-4-piperidinyl)-N'-aminooxamide with 2-Ethylhexyl Glycidyl Ether

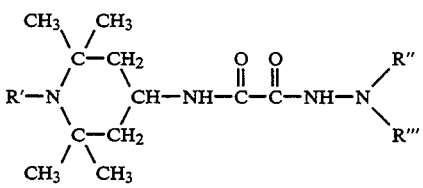

where
R' is hydrogen, a or b;
R'' is hydrogen, a or b;
R''' is hydrogen, a or b;

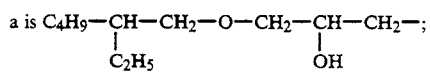

and

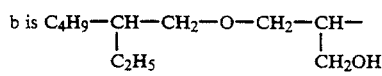

Into a 50 ml 3-necked flask was introduced N-(2,2,6,6-tetramethyl-4-piperidinyl)-N'-aminooxamide (HALS-O) (6.1 g, 0.025 mole) and 2-ethylhexyl glycidyl ether (4.65 g, 0.025 mole). The flask was equipped with a magnetic stirrer, a thermometer and a reflux condenser. The flask was placed in an oil bath and heated to 150°–160° C. for 1 hour with stirring. The reaction mixture was cooled to 130° C. and poured into a small beaker. The viscous liquid was cooled to a brittle solid over dry ice and pulverized with a mortar and pestle. Upon warming to room temperature it became a viscous liquid again. The liquid chromatographic scan of the product showed a large peak for the starting HALS-O and two major peaks for the monoalkylated (i.e., where R' and R'' are hydrogen and R''' is a or b) and dialkylated (i.e., where R' is hydrogen and R'' and R''' are a or b) products. There was no residual 2-ethylhexyl glycidyl ether. The reaction with HALS-O (3.05 g, 0.0125 mole) and 2-ethylhexyl glycidyl ether (4.65 g, 0.025 mole) was repeated. The reaction mixture was heated for 1 hour at 145°–160° C., followed by cooling to room temperature.

The product was a viscous liquid containing five components by liquid chromatography: three major components and small amounts of residual HALS-O and 2-ethylhexyl glycidyl ether. Of the three major components, the retention time of the smaller component corresponded to the monoalkylated product. The largest peak corresponded to the retention time of the dialkylated product and a new peak having the shortest retention time corresponded to a trialkylated product (i.e., where R', R'' and R''' are a or b).

The reaction with HALS-O (3.05 g, 0.0125 mole) and 2-ethylhexyl glycidyl ether (7.0 g, 0.0375 mole) was again repeated. The reaction mixture was heated for 4 hours at 140°–150° C. and was monitored by liquid chromatography. After heating for 1 hour, the reaction mixture contained large amounts of 2-ethylhexyl glycidyl ether and monoalkylated product, a moderate amount of dialkylated product, a small amount of HALS-O and a trace amount of the trialkylated product. After heating for 2 hours, there were still large, roughly equal amounts of the dialkylated and trialkylated products, moderate amounts of residual epoxide and monoalkylated product and a trace amount of residual HALS-O. After 4 hours heating, the major product was the trialkylated product with only small traces of the mono and dialkylated products. The reaction was cooled to room temperature, leaving a viscouus liquid as the product.

EXAMPLE XXVIII

Alkylation of N-(2,2,6,6-tetramethyl-4-piperidinyl)-N'-aminooxamide with 1,2-epoxy-3-phenoxypropane

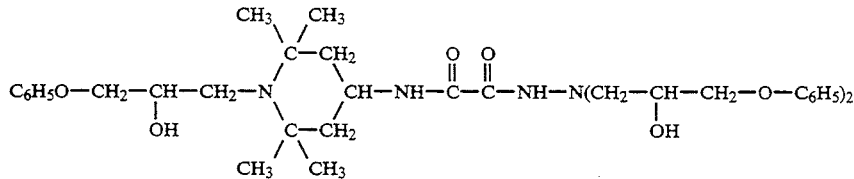

Into a 50 ml 3-necked flask was introduced N-(2,2,6,6-tetramethyl-4-piperidinyl)-N'-aminooxamide (HALS-O) (6.1 g, 0.025 mole) and 1,2-epoxy-3-phenoxypropane (11.3 g, 0.075 mole). The flask was equipped with a magnetic stirrer, a thermometer and a reflux condenser. The flask was then placed in an oil bath and heated to 150° C. for 3 hours. Liquid chromatography of the reaction mixture indicated that primarily the trialkylated product was present, with small amounts of the mono and dialkylated HALS-O and epoxide remaining. The product was cooled to room temperature and was a very viscous liquid.

EXAMPLE XXIX

Preparation of 1-[N-(2,2,6,6-tetramethyl-4-piperidinyl)oxamoyl]-2-[N-(2,2,6,6-tetramethyl-4-piperidinyl)succinamoyl]hydrazine

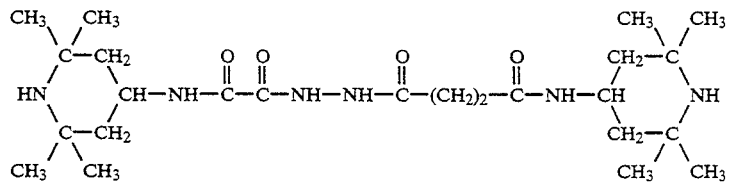

Into a 3-necked 50 ml flask was introduced a 60.9% solution of ethyl N-(2,2,6,6-tetramethyl-4-piperidinyl)oxamate in methanol (4.27 g, 0.01 mole), N-(2,2,6,6-tetramethyl-4-piperidinyl)-N'-aminosuccinamide (2.7 g, 0.01 mole) and 25 ml of anhydrous methanol. The flask was equipped with a thermometer, a magnetic stirrer and a Dean Stark trap with a reflux condenser. The reaction mixture was heated to reflux for ½ hour. Liquid chromatography of the reaction mixture indicated that the starting materials had essentially disappeared and there was one new peak corresponding to the product. The reaction mixture was filtered hot to remove some insoluble material. The filtrate was stripped to dryness on a rotatary evaporator under reduced pressure. The residue was scraped out of the flask and pulverized into a white powder with a mortar and pestle. The white powder was air dried on a watch glass overnight. The product weighed 1.0 grams and had a melting range of 130°–135° C. An infrared scan (nujol mull) of the product contained a strong carbonyl band at 1655 cm$^{-1}$ and two moderate carbonyl bands at 1575 and 1495 cm$^{-1}$.

EXAMPLE XXX

Preparation of 1-[N-(2,2,6,6-tetramethyl-4-piperidinyl)oxamoyl]-2-[N-(3,5-di-t-butyl-4-hydroxyphenyl)oxamoyl]hydrazine

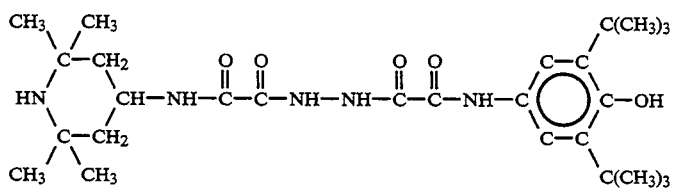

Into a 3-necked 300 ml flask was introduced a 58% solution of methyl N-(2,2,6,6-tetramethyl-4-piperidinyl)oxamate in methanol (8.3 g, 0.02 mole), N-(3,5-di-t-butyl-4-hydroxyphenyl)-N'-aminooxamide (6.1 g, 0.02 mole) and 100 ml of anhydrous methanol. The flask was equipped with a magnetic stirrer, a thermometer and a Dean Stark trap containing a reflux condenser. The reaction mixture was heated in an oil bath to reflux for 3½ hours. At this point, the Dean Stark trap was periodically drained until 40 ml of methanol was collected and solid material formed in the reaction mixture. An additional 10 ml of methanol was distilled from the reaction mixture. The reaction mixture was cooled to 15° C. and the resulting thick slurry was filtered. The filter cake was rinsed with 20 ml of cold methanol and air dried. The product was a white solid weighing 6.2 grams and had a melting range of 196°–202° C. The infrared scan (nujol mull) contained sharp carbonyl bands at 1665, 1585 and 1510 cm$^{-1}$.

EXAMPLE XXXI

Preparation of 1-[N-(2,2,6,6-tetramethyl-4-piperidinyl)oxanoyl]-2-[(4-benzoyl-3-hydroxyphenoxy)acetyl]hydrazine

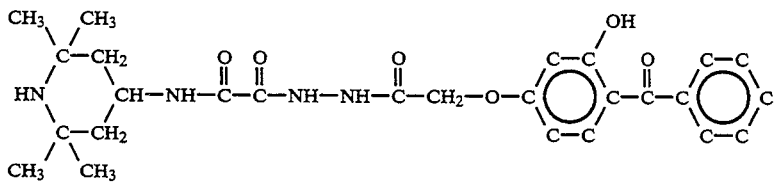

Into a 3-necked 500 ml flask was introduced a 58% solution of methyl N-(2,2,6,6-tetramethyl-4-piperidinyl)oxamate in methanol (21.0 g, 0.05 mole), (4-benzoyl-3-hydroxyphenoxy)acetyl hydrazide (14.25 g, 0.05 mole) and 200 ml of anhydrous methanol. The flask was equipped with a magnetic stirrer, a thermometer and a Dean Stark trap containing a reflux condenser. The reaction mixture was heated in an oil bath to reflux for 3 hours. At this point, the Dean Stark trap was periodically drained to remove a total of 100 ml of methanol. The reaction mixture was cooled to 30° C. and filtered. The filter cake weighed 10.4 grams, had a melting range of 191°–195° C. and was identified as the starting (4-benzoyl-3-hydroxyphenoxy)acetyl hydrazide. The yellow filtrate was stripped on a rotatary evaporator yielding 7.3 g of a cream-colored solid which did not melt below 280° C. The infrared scan (nujol mull) of the high melting solid contained strong sharp carbonyl bands at 1665, 1625, and 1505 cm$^{-1}$ and a weak shoulder at 1595 cm$^{-1}$.

EXAMPLE XXXII

Preparation of 1-[N-(2,2,6,6-tetramethyl-4-piperidinyl)oxamoyl]-2-benzenesulfonylhydrazine

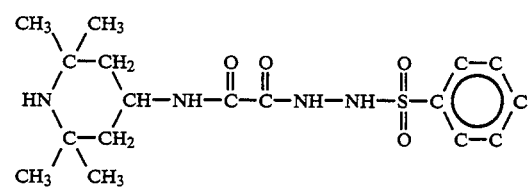

Into a 3-necked 250 ml flask was introduced a 60.9% solution of ethyl N-(2,2,6,6-tetramethyl-4-piperidinyl)oxamate in methanol (21.0 g, 0.05 mole), benzenesulfonyl hydrazide (8.6 g, 0.05 mole) and 125 ml of anhydrous methanol. The flask was equipped with a thermometer, a magnetic stirrer and a Dean Stark trap with a reflux condenser. The mixture was stirred to dissolve the benzenesulfonyl hydrazide and was then heated to reflux for 1½ hours. Methanol was slowly distilled off (approximately 100 ml total) until solid material began to form.

The reaction mixture was filtered to remove the insoluble material. A liquid chromatographic scan of the filtrate indicated that the starting materials were essentially consumed and a new product had formed. The filtrate was stripped to dryness leaving a white residue weighing 9.7 g. The product had a melting range of 88°–92° C. An infrared scan of the product (in CHCl$_3$) contained strong, broad carbonyl bands at 1670 cm$^{-1}$ and 1500 cm$^{-1}$ and a weak carbonyl band at 1610 cm$^{-1}$.

EXAMPLE XXXIII

Preparation of N-(2,2,6,6-tetramethyl-4-piperidinyl)-N-'-methylaminooxamide

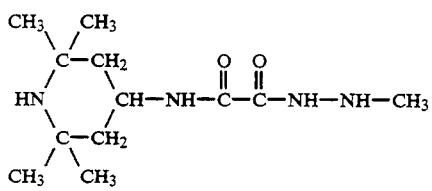

Method A

Into a 3-necked 250 ml flask was introduced methyl N-(2,2,6,6-tetramethyl-4-piperidinyl)oxamate (12.1 g, 0.05 mole), dissolved in 100 ml of methanol. The flask was equipped with a thermometer, a magnetic stirrer, a reflux condenser and a dropping funnel containing methylhydrazine (2.8 g, 0.06 mole). The methylhydrazine was added dropwise to the stirring oxamate solution at room temperature. The reaction was stirred for 5 hours at room temperature and was then allowed to stand overnight. The solvent was stripped off the next morning on a rotatary evaporator under reduced pressure. The residue was a white solid weighing 12.5 g with a melting range of 164°–168° C.

The infrared spectrum of the product contained a strong carbonyl at 1640 cm$^{-1}$ and a moderate carbonyl band at 1520 cm$^{-1}$. The ester band at 1730 cm$^{-1}$ corresponding to the starting material was not present.

Method B

Monoethyl oxalyl-2-methylhydrazide was prepared by adding an equivalent amount of methylhydrazine to a methanol solution of diethyl oxalate at 15°–20° C. The insoluble material that formed was filtered off and the product was isolated by removing the methanol from the filtrate on a rotatary evaporator under reduced pressure.

To a solution of the monoethyl oxalyl-2-methylhydrazide (3.7 g, 0.025 mole) in 20 ml of methanol in a 50 ml flask was added 4-amino-2,2,6,6-tetramethylpiperidine (4.2 g). The reaction was stirred at room temperature for 1 hour and then refluxed for 1 hour.

Upon cooling, the product crystallized out of solution. The product was isolated by filtration and air dried. The yield of isolated product was 2.85 grams (44.5% yield). The infrared scan of the product was the same as that of the product prepared from N-(2,2,6,6-tetramethyl-4-piperidinyl)oxamate and methylhydrazine.

EXAMPLE XXXIV

Preparation of 1-[N-(2,2,6,6-tetramethyl-4-piperidinyl)oxamoyl]-2-acetylhydrazine

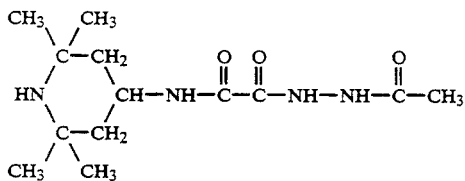

Method A

Into a 3-necked 100 ml flask was introduced acetic hydrazide (3.75 g, 0.05 mole) and a 60% solution of methyl N-(2,2,6,6-tetramethyl-4-piperidinyl)oxamate in anhydrous methanol (20.7 g, 0.05 mole). The flask was equipped with a magnetic stirrer, a thermometer and a Dean Stark trap equipped with a reflux condenser. The flask was placed in an oil bath and the reaction mixture was heated to reflux. Upon reaching reflux temperature (about 70° C.), a white solid quickly formed and a thick slurry resulted within 5 minutes. The slurry was refluxed for ½ hour at 70°–73° C. and was then diluted with 50 ml of methanol. The slurry was filtered hot (60° C.) and the filter cake was rinsed with 25 ml of fresh methanol. After air drying overnight on a watch glass, the white powder weighed 8.6 g (60.5% yield). The product had a melting point of 267°–269° C. An infrared scan (nujol mull) of the product contained carbonyl bands at 1660, 1620, 1565 and 1510 cm$^{-1}$.

Additional product (5.4 g, 38% yield) was recovered by distilling off most of the methanol from the filtrate and refluxing the residue (72° C.) for 10 minutes and repeating the recovery procedure with 25 ml of methanol.

Method B

Into a 3-necked flask was introduced 98% N-(2,2,6,6-tetramethyl-4-piperidinyl)-N'-aminooxamide (HALS-O) (12.4 g, 0.05 mole) and 125 ml of THF. The flask was equipped with a magnetic stirrer, a thermometer, a reflux condenser and a dropping funnel containing acetic anhydride (5.1 g, 0.05 mole) diluted to 25 ml with THF. The stirrer was activated and the anhydride solution was added dropwise to the stirring slurry of HALS-O over 2–3 minutes. The reaction temperature rose from 22° C. to 32° C. and the slurry changed in physical appearance. After the addition was complete, the reaction was stirred 1 hour while the temperature dropped back to 26° C. The slurry was filtered and the filter cake was slurried in 100 ml of 3% sodium bicarbonate solution and refiltered. The filter cake was air dried overnight on a watch glass. After drying, the product weighed 12.6 g (88.7% yield). The product had a melting point of 265°–268° C. and the infrared scan (nujol mull) of the product was the same as that of the product from Method A.

EXAMPLE XXXV

Preparation of 1-[N-(2,2,6,6-tetramethyl-4-piperidinyl)oxamoyl]-2-propionylhydrazine

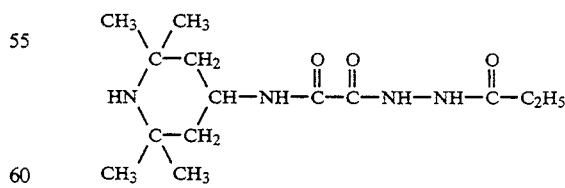

Into a 3-necked 250 ml flask was introduced HALS-O (12.2 g, 0.05 mole) and 150 ml THF. The flask was equipped with a magnetic stirrer, a thermometer, a reflux condenser and a dropping funnel containing propionic anhydride (6.5 g, 0.05 mole) diluted to 15 ml with THF. The stirrer was activated and the propionic anhydride solution was added dropwise over 5 minutes. The reaction temperature slowly rose from 19° C. to 27° C. where the reaction mixture gelled. The reaction mixture was heated to reflux in an oil bath for 1 hour. The gelled material went into solution upon heating followed by a solid material precipitating out of solution to form a thin slurry. The reaction was cooled to 50° C. and filtered. The filter cake was washed with fresh THF and then air dried overnight. The product was a white powder weighing 13.9 g (93% yield). The product had a melting range of 221°–225° C. and the infrared scan (nujol mull) of the product contained carbonyl bands at 1660, 1620, 1565 and 1500 cm$^{-1}$.

EXAMPLE XXXVI

Preparation of 1-[N-(2,2,6,6-tetramethyl-4-piperidinyl)oxamoyl]-2-butyroylhydrazine

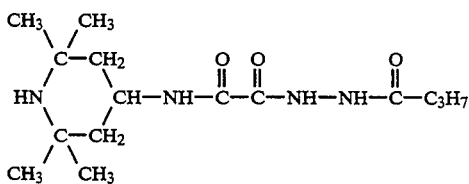

Method A

Into a 3-necked 250 ml flask was introduced butyric hydrazide (5.1 g, 0.05 mole) and a 55% solution of methyl N-(2,2,6,6-tetramethyl-4-piperidinyl)oxamate in anhydrous methanol (22.0 g, 0.05 mole). The flask was equipped with a magnetic stirrer, a thermometer and a Dean Stark trap equipped with a reflux condenser. The flask was placed in an oil bath and the reaction mixture was heated to reflux. The butyric hydrazide went into solution at about 30° C. After refluxing 10–15 minutes, a solid material began to form. The methanol was slowly distilled off by gradually draining the Dean Stark trap. After the methanol distillation stopped (75°–80° C.), the reaction mixture was a thick, viscous, taffy-like material. The reaction mixture was diluted with 50 ml of methanol and refluxed until the reaction mass dissolved (15 minutes). The solution was then cooled to 20° C. in a cold water bath. Crystals began to form at about 40° C. The cold slurry was filtered and the filter cake was rinsed with a little cold, fresh methanol. The filter cake was air dried overnight. The dry product weighed 12.7 g (81.4% yield), had a melting range of 186°–190° C. and its infrared scan (nujol mull) contained carbonyl bands at 1660, 1620, 1570 and 1500 cm$^{-1}$.

The methanol filtrate was concentrated on a rotating evaporator leaving 4.5 g of a viscous liquid. Liquid chromatography indicated that this viscous liquid was a mixture of the product and the two starting materials, suitable for recycling.

Method B

Into a 3-necked 250 ml flask was introduced HALS-O (12.2 g, 0.05 mole) and 150 ml THF. The flask was equipped with a magnetic stirrer, a thermometer, a reflux condenser and a dropping funnel containing butyric anhydride (7.9 g, 0.05 mole) diluted to 15 ml with THF. The stirrer was activated and the butyric anhydride solution was added dropwise over 7 minutes. The reaction temperature slowly rose from 18° C. to 22° C. The reaction mixture was then heated to reflux in an oil bath for 1 hour. The reaction mixture was cooled to 60° C. and the insoluble material was filtered off and air dried. The dry product weighed 9.2 g and had a melting range of 185–192° C. The product was slurried in refluxing isopropanol for 10 minutes, refiltered and dried. The dry product weighed 6.5 g (40% yield), had a melting range of 185°–191° C. and its infrared scan was essentially the same as the product prepared in Method A.

The THF and isopropanol filtrates were stripped to dryness on a rotating evaporator. Infrared and liquid chromatography scans indicated the residues were primarily the butyric acid salt of the desired product plus a small amount of the desired product.

EXAMPLE XXXVII

Preparation of 2,2'-Di-[N-(2,2,6,6-tetramethyl-4-piperidinyl)oxamoyl]adipic dihydrazide

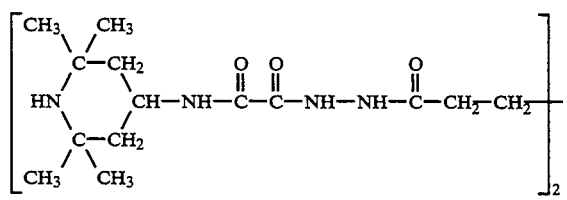

Into a 3-necked 100 ml flask was introduced adipic dihydrazide (4.35 g, 0.025 mole) and a 55% solution of methyl N-(2,2,6,6-tetramethyl-4-piperidinyl)oxamate in anhydrous methanol (22.0 g, 0.05 mole). The flask was equipped with a magnetic stirrer, a thermometer and a Dean Stark trap equipped with a reflux condenser. The flask was placed in an oil bath and the reaction mixture was heated to reflux. The reaction mixture was refluxed ½ hour after which the methanol was slowly distilled off by gradually draining the Dean Stark trap. The reaction was refluxed for approximately 4 hours before the distillation was stopped. The reaction mixture was diluted with 50 ml of methanol, refluxed 5 minutes and cooled to 60° C. The white solid that had formed was filtered off, rinsed with fresh methanol and air dried. The dry product weighed 12.6 g (84.6% yield) and had a melting range of 165°–175° C. The infrared scan of the product contained carbonyl bands at 1670, 1625 (weak), 1585 and 1500 cm$^{-1}$.

EXAMPLES XXXVIII–XLVII

Preparation of 1-[N-(2,2,6,6-tetramethyl-4-piperidinyl)oxamoyl]-2-acylhydrazines

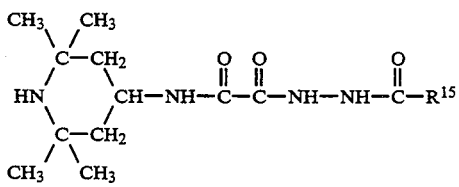

EXAMPLES XXXVIII–XLVII were prepared using Method A of Example XXXVI. Into a 3-necked 250 ml flask was introduced 0.05 mole of the appropriate hydrazide and a 55% solution of methyl N-(2,2,6,6-tetramethyl-4-piperidinyl)oxamate in anhydrous methanol (22.0 g, 0.05 mole). The flask was equipped with a magnetic stirrer, a thermometer and a Dean Stark trap equipped with a reflux condenser. The flask was placed in an oil bath and the reaction mixture was heated to reflux. The methanol was slowly distilled off by gradually draining the Dean Stark trap. After the methanol distillation stopped, the reaction mixture was heated an additional 30–60 minutes at 90°–110° C. The reaction mixture was then carefully diluted with 50–100 ml of methanol and was allowed to reflux 15–30 minutes. If the product did not dissolve in the hot methanol, it was isolated by filtration. If the product was soluble in hot methanol, attempts were made to crystallize it out of methanol by cooling the methanol solution in a freezer (−5° C.). If the product would not crystallize out of methanol, the methanol was stripped off under vacuum on a rotating evaporator. A vacuum pump and a heat gun were employed to drive off the last traces of methanol, thereby converting the residue from a sticky viscous liquid to a hard crystalline solid. The solid was then scraped out of the evaporating flask and pulverized with a mortar and pestle. The results are summarized in Table III.

reflux condenser and a dropping funnel containing valetic anhydride (18.6 g, 0.1 mole). The stirrer was activated and the anhydride was added over 15 minutes. The temperature gradually rose from 18° C. to 25° C. The reaction mixture was heated to reflux in an oil bath for 1 hour. The hot reaction mixture (60° C.) was filtered to remove some insoluble material.

The filter cake weighed 1.6 g after drying and its infrared scan was the same as the product prepared in Example XXXIX indicating it was the uncomplexed 1-[N-(2,2,6,6-tetramethyl-4-piperidinyl)oxamoyl]-2-valeroylhydrazine.

The THF filtrate was concentrated to dryness on a rotating evaporator under reduced pressure. The residue was slurried in 100 ml of isopropanol, filtered and the filter cake was dried. The dry product weighed 36.6 g and had a melting range of 155°–170° C. A second crop of 2.4 g was obtained by stripping off the isopropanol, slurrying the residue in hexane and filtering off the solid product. The infrared scans of the two crops showed a very strong carbonyl band at 1645 cm$^{-1}$ with

TABLE III

1-[N-(2,2,6,6-tetramethyl-4-piperidinyl)oxamoyl]-2-acylhydrazines

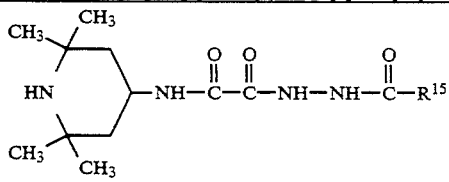

| Example # | R$^{15}$ | Starting Hydrazide | Yield grams | % Yield | m.p. °C. | Method of Isolation | IR Carbonyl Bands cm$^{-1}$ |
|---|---|---|---|---|---|---|---|
| XXXVIII | (CH$_3$)$_2$CH | Isobutyric | 13.8 | 88.5 | 216–220 | filt. | 1665, 1630, 1580, 1510 |
| XXXIV | C$_4$H$_9$ | Valeric | 12.4 | 76.1 | 162–167 | crystn. | 1665, 1630, 1580, 1510 |
| XL | C$_5$H$_{11}$ | Caproic | 10.3 | 60.5 | 142–145 | crystn. | 1665, 1625, 1585, 1500 |
| XLI | C$_6$H$_{13}$ | Heptanoic | 17.7 | 100 | 99–110 | crystn. | 1665, 1580, 1500 |
| XLII | C$_7$H$_{15}$ | Caprylic | 15.0 | 81.5 | 98–102 | crystn. | 1665, 1580, 1495 |
| XLIII | C$_9$H$_{19}$ | Decanoic | 19.8 | 100 | 83–87 | evapn. | 1660, 1585, 1500 |
| XLIV | C$_{13}$H$_{27}$ | Myristic | 21.5 | 95.1 | 81–88 | evapn. | 1660, 1585, 1500 |
| XLV | C$_{15}$H$_{31}$ | Palmitic | 20.5 | 85.4 | 77–87 | evapn. | 1665, 1585, 1500 |
| XLVI | C$_6$H$_5$ | Benzoic | 12.5 | 72.2 | 221–223 | filt. | 1665, 1580, 1565, 1510 |
| XLVII | ![salicyl] | Salicylic | 17.55 | 97.0 | >300 | filt. | 1660, 1610, 1590, 1550 |

EXAMPLE XLVIII

Preparation of the Valetic Acid Salt of 1-[N-(2,2,6,6-tetramethyl-4-piperidinyl)oxamoyl]-2-valeroylhydrazine

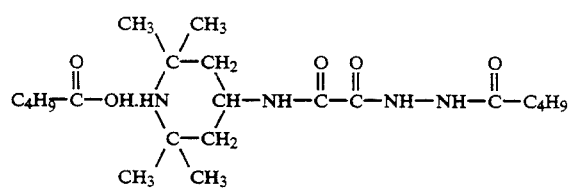

Into a 3-necked 500 ml flask was introduced HALS-O (24.2 g, 0.1 mole) and 300 ml of THF. The flask was equipped with a magnetic stirrer, a thermometer, a a weak shoulder at 1660 cm$^{-1}$, a broad carbonyl at 1550 cm$^{-1}$ and sharp weaker bands at 1520 and 1490 cm$^{-1}$. The combined yield was 39.0 g or a 91.3% yield for the acid salt. A TGA scan of the product indicated it lost 27% (theoretrical is 24%) of its weight upon heating from 150° C. to 260° C. The TGA scan indicated that the salt dissociated upon heating and slowly evolved valetic acid.

EXAMPLE XLIX

Preparation of the Hexanoic Acid Salt of 1-[N-(2,2,6,6-tetramethyl-4-piperidinyl)oxamoyl]-2-hexanoylhydrazine

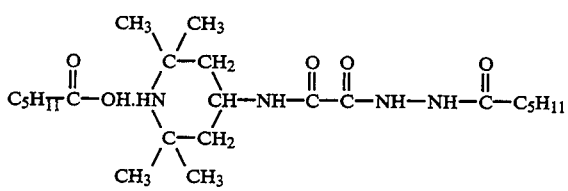

The hexanoic acid salt was prepared in the same manner as the valeric acid salt of Example XLVIII with the exception that 0.1 mole of hexanoic anhydride was substituted for the valeric anhydride. No insoluble material formed in the hot THF reaction mixture. The product was isolated by stripping off the THF, slurrying the residue in isopropanol, filtering off the insoluble material and drying the filter cake. The yield was 42.7 g (93.5% yield). The product had a melting range of 155°–162° C. and its infrared scan (nujol mull) contained a very strong, sharp carbonyl band at 1650 cm$^{-1}$ and weaker carbonyl bands at 1620, 1540 and 1490 cm$^{-1}$. A TGA scan of the product indicated it lost 28% (theoretical is 25.5%) of its weight upon heating from 150° to 260° C. The TGA scan indicated that the salt dissociated upon heating and slowly evolved hexanoic acid.

EXAMPLE L

Preparation of the Heptanoic Acid Salt of 1-[N-(2,2,6,6-tetramethyl-4-piperidinyl)oxamoyl]-2-heptanoylhydrazine

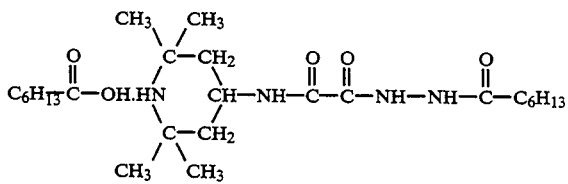

The heptanoic acid salt was prepared in the same manner as the valetic acid salt of Example XLVIII with the exception that 0.1 mole of heptanoic anhydride was substituted for the valetic anhydride and the reaction mixture was not heated. After stirring for two hours at room temperature, the reaction mixture solidified. The reaction mixture was allowed to stand overnight and the solid product was filtered off the next morning. After drying, the product weighed 32.2 g and had a melting range of 140°–150° C.

An additional 7.3 g of product was isolated by concentrating the THF filtrate, slurrying the residue in isopropanol, filtering off and drying the insoluble material. The total yield was 39.5 g (81.5% yield).

The infrared scan of the product contained a very strong, sharp carbonyl band at 1660 cm$^{-1}$ with weaker carbonyl bands at 1615, 1545 and 1490 cm$^{-1}$. A TGA scan of the product indicated it lost 30% (theoretical is 27%) of its weight upon heating from 150° C. to 260° C. The TGA scan indicated that the salt dissociated upon heating and slowly evolved heptanoic acid.

EXAMPLES LI–XCVII

Preparation, Weathering and Evaluation of Tensile Bars Containing Derivatives of HALS Substituted Amic Acid Hydrazides Dry blends of Himont TM 6501 polypropylene, various HALS amic acid hydrazide derivatives and optionally a small amount of a hindered phenol antioxidant (Irganox TM 1076) were prepared in a polyethylene container (for composition, see Table IV). The blends were shaken well to insure a good dispersion of the additives in the polypropylene. The blends were then extruded on a Brabender Prep Center Extruder Model No. 1340 having a 1¼ inch screw diameter with a length to diameter ratio of 25:1. The extruder was operated at a screw speed of 30 RPM and all of the heating zones were controlled at 200° C. The first 100 g of extrudate were used to purge out the extruder between runs and was discarded. The remaining extrudate was air cooled and pelletized. The concentration of the 2,2,6,6-tetramethyl-4-piperidinyl group in the polypropylene was approximately 0.3%. The concentration of the Irganox TM 1076 (when used) was approximately 0.25%. UV-Chek TM AM-340 was included in some blends as a synergist at a concentration of 0.22%.

The pellets were injection molded in a Newbury 25 ton injection molding machine at 400° F. into 7⅜"×⅜"×⅛" tensile bars.

A control sample containing only Irganox TM 1076 was included for comparison. Control samples containing Irganox TM 1076 and Ciba-Geigy's Chimasorb TM 944 and Tinuvin TM 770 were also included for comparison.

The tensile bars were placed in a QUV Accelerated Weather Tester (Q Panel Company) for various exposure times. The QUV operated with an 8 hour light cycle using UV-B bulbs at 60° C. and a 4 hour condensation cycle at 50° C. Samples were placed in the QUV and withdrawn periodically at the same time of day. The tensile bars were pulled on an instrumented Instron (Model 4204) according to ASTM Procedure 638. The minimum QUV exposure time interval required to obtain a brittle break in the Instron test was determined. A result was considered a brittle break when the tensile bar snapped before 15% elongation was obtained.

The QUV time interval required to generate spotting and clouding of the surface of the tensile bars was also noted. The results are summarized in Table IV.

Tensile bars were also exposed to UV-A bulbs in a QUV under the same conditions for 60 days. A few were also tested after longer intervals. The tensile bars were then pulled on the Instron. A brittle break was considered a failure and greater than 15% elongation was considered passing. These results are also summarized in Table IV.

TABLE IV
STABILIZATION OF POLYPROPYLENE WITH HALS AMIC ACID DERIVATIVES

| EX-AMPLE # | HALS COMPOUND EXAMPLE # | GRAMS | POLY-PROPYLENE (GRAMS) | IRGANOX 1076 (GRAMS) | UV CHEK AM-340 (GRAMS) | DAYS TO SPOTTING IN QUV-B | DAYS TO BRITTLE BREAK IN QUV-B | PASS-FAIL IN QUV-A | | | |
|---|---|---|---|---|---|---|---|---|---|---|---|
| | | | | | | | | 60 DAYS | 80 DAYS | 100 DAYS | 120 DAYS |
| LI | II | 3.45 | 445 | — | — | 19–21 | >30<35 | NT | | | |
| LII | II | 3.45 | 445 | 1.1 | — | 26–28 | >30<35 | NT | | | |
| LIII | III | 3.25 | 445 | — | — | >50<70 | >50<70 | PASS | | | |
| LIV | III | 3.25 | 445 | 1.1 | — | >50<70 | >50<70 | PASS | PASS | | |
| LV | III | 3.25 | 445 | — | 1.0 | >70 | >70 | PASS | PASS | PASS | PASS |
| LVI | IV | 5.1 | 445 | — | — | >50<60 | >50<60 | PASS | | | |
| LVII | IV | 5.1 | 445 | 1.1 | — | >50<60 | >50<60 | NT | | | |
| LVIII | V | 3.5 | 445 | — | — | >45<50 | >35<40 | PASS | | | |
| LIX | V | 3.5 | 445 | 1.1 | — | >50 | >35<40 | NT | | | |
| LX | VI | 3.8 | 445 | — | — | >35<40 | >20<30 | NT | | | |
| LXI | VI | 3.8 | 445 | 1.1 | — | >35<40 | >30<35 | NT | | | |
| LXII | IX | 3.0 | 445 | — | — | <12 | >25<30 | NT | | | |
| LXIII | IX | 3.0 | 445 | 1.1 | — | 19 | >25<30 | NT | | | |
| LXIV | X | 3.4 | 445 | — | — | >40<50 | >40<50 | PASS | | | |
| LXV | X | 3.4 | 445 | 1.1 | — | >40<50 | >50<70 | NT | | | |
| LXVI | XI | 3.5 | 445 | — | — | >30<40 | >30<35 | FAIL | | | |
| LXVII | XI | 3.5 | 445 | 1.1 | — | >35<40 | >40<50 | PASS | | | |
| LXVIII | XII | 4.2 | 445 | — | — | >50 | >50<70 | PASS | PASS | | |
| LXIX | XII | 4.2 | 445 | 1.1 | — | >50 | >50<70 | PASS | PASS | | |
| LXX | XV | 2.7 | 445 | — | — | 35 | >40<50 | PASS | | | |
| LXXI | XV | 2.7 | 445 | 1.1 | — | >50 | >50<70 | NT | | | |
| LXXII | XVI | 2.8 | 445 | — | — | >50<70 | >50<70 | PASS | PASS | | |
| LXXIII | XVI | 2.8 | 445 | 1.1 | — | >50<70 | >50<70 | NT | | | |
| LXXIV | XVI | 2.8 | 445 | — | 1.0 | >70 | >70 | PASS | PASS | PASS | PASS |
| LXXV | XVII | 3.1 | 445 | — | — | >50 | >40<50 | NT | | | |
| LXXVI | XVII | 3.1 | 445 | 1.1 | — | >50 | >40<50 | NT | | | |
| LXXVII | XVIII | 1.0 | 250 | — | — | >30 | >30 | NT | | | |
| LXXVIII | XXI | 4.6 | 445 | — | — | >60<70 | >70 | PASS | PASS | PASS | PASS |
| LXXIX | XXI | 4.6 | 445 | — | 1.0 | >70 | >70 | PASS | PASS | PASS | PASS |
| LXXX | XXII | 3.0 | 445 | — | — | >40<50 | >40<50 | PASS | PASS | PASS | PASS |
| LXXXI | XXII | 3.0 | 445 | 1.1 | — | >40<50 | >50<60 | PASS | PASS | PASS | PASS |
| LXXXII | XXV | 4.5 | 445 | — | — | >35<40 | >35<40 | NT | | | |
| LXXXIII | XXV | 4.5 | 445 | 1.1 | — | 40 | >35<40 | NT | | | |
| LXXXIV | XXVI | 4.9 | 445 | — | — | >60<70 | >70 | PASS | PASS | PASS | |
| LXXXV | XXVI | 4.9 | 445 | 1.1 | — | >60<70 | >60<70 | PASS | PASS | PASS | |
| LXXXVI | XXX | 4.9 | 445 | — | — | <20 | >20<25 | NT | | | |
| LXXXVII | XXXIII | 2.4 | 445 | — | — | >30<35 | >35<40 | PASS | | | |
| LXXXVIII | XXXIII | 2.4 | 445 | 1.1 | — | 40 | >40<50 | NT | | | |
| LXXXIX | VII | 3.6 | 445 | — | — | >35<40 | >35<40 | FAIL | | | |
| XC | VIII | 5.5 | 445 | — | — | >35<40 | >30 35 | PASS | | | |
| XCI | VIII | 5.5 | 445 | 1.1 | — | >40 | >30<35 | PASS | | | |
| XCII | XIII | 3.7 | 445 | — | — | <30 | 15 15 | PASS | | | |
| XCIII | XIII | 3.7 | 445 | 1.1 | — | >30<35 | >30<35 | PASS | | | |
| XCIV | XIV | 3.5 | 445 | — | — | >25<30 | >25<30 | PASS | | | |
| XCV | XIV | 3.5 | 445 | 1.1 | — | >30<35 | >30<35 | PASS | | | |
| XCVI | XX | 3.2 | 445 | — | — | >30<40 | 12 15 | FAIL | | | |
| XCVII | XX | 3.2 | 445 | 1.1 | — | >40 | >15<20 | PASS | | | |
| C-1 | — | — | 445 | 1.1 | — | >5<7 | >4<5 | FAIL | | | |
| C-2 | TINUVIN 770 | 2.3 | 445 | 1.1 | — | >35 | >20<25 | FAIL | | | |
| C-3 | CHIMASORB 944 | 2.85 | 445 | 1.1 | — | >33<35 | >20<25 | FAIL | | | |

NT = NOT TESTED

The results obtained indicate that the compounds evaluated are very good light stabilizers and are more efficient than Tinuvin ™ 770 and Chimasorb 944 upon exposure to both UV-A and UV-B light.

EXAMPLE XCVIII

Preparation of 1-[N-(2,2,6,6-tetramethyl-4-piperidinyl)oxamoyl]-2-(1,2,2,6,6-pentamethyl-4-piperidinyloxycarbonyl)hydrazine

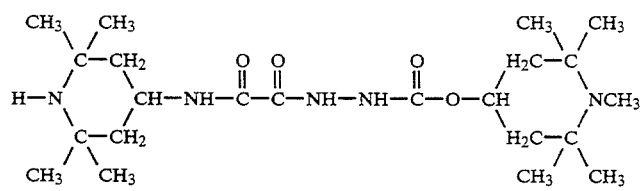

Method A—Preparation of Phenyl 1,2,2,6,6-Pentamethyl-4-piperidinyl Carbonate Into a 500 ml 3-neck flask was added 17.1 grams (0.1 mole) 1,2,2,6,6-pentamethyl-4-piperidinol and 300 mls of methyl t-butyl ether (MtBE). The flask was equipped with a magnetic stirrer, thermometer, reflux condenser and dropping funnel containing 15.6 grams (0.1 mole) phenyl chloroformate. The phenyl chloroformate was slowly added to the 1,2,2,6,6-pentamethyl-4-piperidinol solution without any appreciable exotherm. Then 11.2 grams (0.1 mole) of 1,4-diazabicyclo(2.2.2)octane (DABCO) was added at room temperature. The temperature rose to 50° C. and a precipitate formed. The reaction was stirred for 2 hours, an additional 2 grams of DABCO and 1.25 grams of phenyl chloroformate was added, the reaction heated to reflux and refluxed 2 hours. The reaction mixture was cooled, transferred to a separatory funnel and washed with water to remove DABCO, DABCO hydrochloride and a small amount of 1,2,2,6,6-pentamethyl-4-piperidinol. The product was then extracted out of the MtBE layer with 100 mls of 5% HCl diluted with water to 400 mls. The MtBE layer which contained diphenyl carbonate was discarded. The acid layer was made basic with 100 ml of 10% NaOH. The product was extracted out of the aqueous layer with 200 ml MtBE. The MtBE extract was washed with 100 ml 5% NaHCO$_3$, dried over anhydrous MgSO$_4$, filtered and the MtBE stripped off on a rotating evaporator under reduced pressure. The residue was a white solid weighing 20.4 grams (70.1% crude yield) which had a melting point of 63°-67° C. Liquid chromatography indicated the product was essentially one component. The infrared spectrum contained a strong carbonyl peak at 1755 cm$^{-1}$.

Method B—Preparation of 1,2,2,6,6-Pentamethyl-4-piperidinyl Carbazate

Into a 250 ml 3-neck flask was added 20.0 grams (0.069 mole) of phenyl 1,2,2,6,6-pentamethyl-4-piperidinyl carbonate and 100 mls of methanol. The flask was equipped with a magnetic stirrer, thermometer, reflux condenser and dropping funnel containing 3.8 grams (0.076 mole) of 64% aqueous hydrazine. The hydrazine was added slowly to the stirring methanol solution at room temperature. There was a slight exotherm. The reaction mixture was stirred for 5 hours at room temperature at which point liquid chromatography indicated the reaction was complete. The methanol was stripped off on a rotating evaporator under reduced pressure and the residue was dissolved in 150 ml MtBE. The MtBE solution was washed 3 times with 25 ml portions of 5% NaOH saturated with sodium chloride to remove the phenol that was generated. The MtBE layer was dried over anhydrous MgSO$_4$, filtered and the MtBE stripped off on a rotating evaporator under reduced pressure. The residue was a white solid (m.p. 90°-94° C.) weighing 14.3 grams (90.5% crude yield). Liquid chromatography indicated the product was one component. The infrared spectrum contained a strong carbonyl peak at 1710 cm$^{-1}$ and a moderate peak at 1625 cm$^{-1}$.

Method C—Preparation of 1-[N-(2,2,6,6-tetramethyl-4-piperidinyl)oxamoyl]-2-(1,2,2,6,6-pentamethyl-4-piperidinyloxycarbonyl)hydrazine Into a 100 ml 3-neck flask was added 7.3 grams (0.0318 mole) of 1,2,2,6,6-pentamethyl-4-piperidinyl carbazate, 12.9 grams (0.032 mole) of a 60% solution of ethyl N-(2,2,6,6-tetramethyl-4-piperidinyl)oxamate in methanol and 15 ml of methanol. The flask was equipped with a magnetic stirrer, thermometer and a Dean Stark trap with reflux condenser. The flask was placed in a hot oil bath and heated to reflux. The methanol was distilled off through the Dean Stark trap and the residue was heated for 4 hours at 75°-80° C. Liquid chromatography of the residue indicated that the reaction had proceeded to 85-90% of completion. The reaction was cooled to 50° C. and 50 ml of methanol was added to dissolve the product. The methanol solution was cooled in the freezer (−10° C.) overnight and the next day the crystals that formed were filtered off and air dried. The dry crystals weighed 3.1 grams and melted at 165°-170° C. A liquid chromatography scan indicated the presence of only one component. The infrared spectrum of the product contained a weak carbonyl peak at 1740 cm$^{-1}$ and strong, sharp carbonyl peaks at 1600 and 1685 cm$^{-1}$. A second crop of 4.5 grams was obtained by concentrating the filtrate to about 25 ml, cooling and filtering off the solids that formed. The filtrate was stripped to dryness, leaving 7.0 grams of product which was contaminated with small amounts of the starting materials.

EXAMPLE XCIX

1-[N-(2,2,6,6-tetramethyl-4-piperidinyl)oxamoyl]-2-(2,2,6,6-tetramethyl-4-piperidinyloxycarbonyl)hydrazine

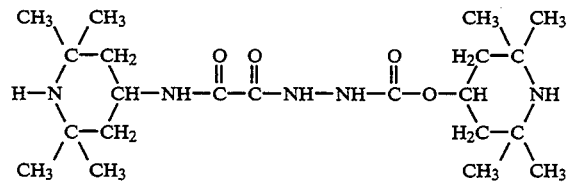

Method A—Preparation of Phenyl 2,2,6,6-Tetramethyl-4-piperidinyl Carbonate

Into a 500 ml 3-neck flask was added 23.2 grams (0.14 mole) of 95% 2,2,6,6-tetramethyl-4-piperidinol and 400 ml of methylene chloride. The flask was equipped with a magnetic stirrer, thermometer, reflux condenser and dropping funnel containing 11.2 grams (0.07 mole) of phenyl chloroformate. The phenyl chloroformate was slowly added to the 2,2,6,6-tetramethyl-4-piperidinol solution without any appreciable exotherm. Then 0.5 grams of 1,4-diazabicyclo(2.2.2)octane (DABCO) was added at room temperature. The temperature rose to 35° C. and a precipitate formed. Another 0.5 gram of DABCO was added but no further exotherm occurred. After stirring for 1½ hours, the solids were filtered off and the methylene chloride solution was washed with water, 10% NaOH and water again, dried over anhydrous MgSO$_4$, filtered and the solvent stripped off on a rotating evaporator under reduced pressure. The residue was a white solid weighing 17.4 grams (90% crude yield) which had a melting point of 62°-65° C. Liquid chromatography indicated the product was essentially one component. The infrared spectrum contained a strong carbonyl peak at 1760 cm$^{-1}$ and a moderate carbonyl peak at 1710 cm$^{-1}$.

Method B—Preparation of 2,2,6,6-tetramethyl-4-piperidinyl Carbazate

Into a 300 ml 3-neck flask were added 16.9 grams (0.061 mole) of phenyl 2,2,6,6-tetramethyl-4-piperidinyl carbonate and 100 ml of methanol. The flask was equipped with a magnetic stirrer, thermometer, reflux condenser and dropping funnel containing 3.4 grams (0.067 mole) of 64% aqueous hydrazine. The hydrazine

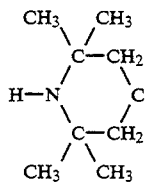 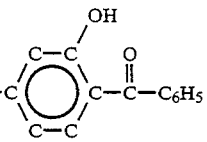

was added slowly to the stirring methanol solution at room temperature. There was a slight exotherm. The reaction mixture was stirred for 3 hours and then allowed to stand overnight (i.e. for 20 hours) at room temperature. The next day, the methanol was stripped off on a rotating evaporator and the liquid residue dissolved in 150 ml of MtBE and washed with 50 ml of 10% NaOH which was saturated with salt. The MtBE solution was dried over anhydrous MgSO$_4$, filtered and the MtBE stripped off on a rotating evaporator under reduced pressure. The residue, a very viscous liquid, was slurried in 20 ml of hexane until a solid formed. The solid was filtered off and air dried. The product weighed 6.4 grams (49% crude yield), had a melting point of 93°–94° C. and gas chromatography indicated it was about 95% pure. The infrared scan contained a strong carbonyl peak at 1710 cm$^{-1}$ and a moderate carbonyl peak at 1625 cm$^{-1}$. An additional 5.26 grams of crude product was recovered by extracting the aqueous wash with methylene chloride and stripping off the solvent.

Method C—Preparation of 1-[N-(2,2,6,6-tetramethyl-4-piperidinyl)oxamoyl]-2-(2,2,6,6-tetramethyl-4-piperidinyloxycarbonyl)hydrazine Into a 100 ml 3-neck flask was added 7.3 grams (0.0318 mole) of 1,2,2,6,6-pentamethyl-4-piperidinyl carbazate, 12.9 grams (0.032 mole) of a 60% solution of ethyl N-(2,2,6,6-tetramethyl-4-piperidinyl)oxamate in methanol and 15 ml of methanol. The flask was equipped with a magnetic stirrer, thermometer and a Dean Stark trap with reflux condenser. The flask was placed in a hot oil bath and heated to reflux. The methanol was distilled off through the Dean Stark trap and the residue was cooked for 4 hours at 75°–80° C. Liquid chromatography of the residue indicated the reaction had gone to 85–90% of completion. The reaction was cooled to 50° C. and 50 ml of methanol was added to dissolve the product. The methanol solution was cooled in the freezer (at −10° C.) overnight and the next day, the crystals that formed were filtered off and air dried. The dry crystals weighed 3.1 grams and melted at 165°–170° C. A liquid chromatography scan indicated the presence of only one peak. The infrared spectrum of the product contained a weak carbonyl peak at 1740 cm$^{-1}$ and strong, sharp carbonyl peaks at 1600 and 1685 cm$^{-1}$. A second crop of 4.5 grams was obtained by concentrating the filtrate to about 25 ml, cooling and filtering off the solids that formed. The filtrate was stripped to dryness, leaving 7.0 grams of product which was contaminated with small amounts of the starting materials.

EXAMPLE C

Preparation of 1-[N-(2,2,6,6-tetramethyl-4-piperidinyl)oxamoyl]-2-[2-(3-hydroxy-4-benzoylphenoxy)ethoxycarbonyl]hydrazine Method A—Preparation of 2-(3-Hydroxy-4-benzoylphenoxy)ethyl Carbazate Into a 250 ml 3-neck flask was added 5.4 grams (0.11 mole) of 64% aqueous hydrazine and 50 mls of THF. The flask was equipped with a magnetic stirrer, thermometer, reflux condenser and a dropping funnel containing 9.6 grams (0.03 mole) of 2-(3-hydroxy-4-benzoylphenoxy)ethyl chloroformate dissolved in 50 ml of THF. The chloroformate solution was added dropwise to the stirring hydrazine solution over ½ hour. The temperature quickly exothermed to 36° C. and slowly subsided after the addition was over. The reaction was stirred an additional ½ hour and concentrated to 31 grams. The THF solution was added to 300 ml of water. A sticky solid formed. The solid was filtered off, taken up in methylene chloride, dried over Na$_2$SO$_4$, filtered and the methylene chloride stripped off. The residue was a viscous orange-brown liquid. The crude product was slurried in 150 ml of warm MtBE. Most of the crude product went into solution, leaving a dark brown liquid residue. The yellow MtBE layer was decanted off and the MtBE stripped off on a rotating evaporator, leaving 9.0 grams of a yellow viscous liquid. Liquid chromatography indicated it was about 92% pure. The residue was slurried in warm methanol and upon cooling, a solid formed. The solid was filtered off and after air drying, weighed 6.4 grams (67% yield) and had a melting point of 58°–61° C.

Method B—Preparation of 1-[N-(2,2,6,6-tetramethyl-4-piperidinyl)oxamoyl]-2-[2-(3-hydroxy-4-benzoylphenoxy)ethoxycarbonyl]hydrazine Into a 100 ml 3-neck flask was added 6.4 grams (0.027 mole) of 2-(3-hydroxy-4-benzoylphenoxy)ethyl carbazate from (A), 8.1 grams (0.027 mole) of a 60% solution of ethyl N-(2,2,6,6-tetramethyl-4-piperidinyl)oxamate and 25 ml of methanol. The flask was equipped with a magnetic stirrer, thermometer and a Dean Stark trap with a reflux condenser. The reaction was heated in an oil bath and the methanol was slowly distilled off through the Dean Stark trap. After the methanol stopped coming over, the reaction was heated one hour, a vacuum was applied to the system to remove any residual methanol and the reaction was heated for another 1½ hours at 70° C. The reaction was dissolved in 50 ml of hot methanol. The solution was filtered to remove a small amount of insoluble material. The methanol was stripped from the filtrate on a rotating evaporator, leaving 9.4 grams of a yellow crystalline solid. Liquid chromatography indicated the product was about 85-90% pure.

EXAMPLE CI

Preparation of 1-[N-(2,2,6,6-tetramethyl-4-piperidinyl)-oxamoyl]-2-(allyloxycarbonyl)hydrazine ml. Upon addition of 25 ml of methyl t-butyl ether, a white solid formed. The solid was filtered off and dried in a vacuum oven over night. The dry powder weighed 22.1 grams (85.7% yield) and assayed 100% by liquid chromatography. The infrared scan of the product contained a weak carbonyl at 1750 cm$^{-1}$ and a strong carbonyl at 1680 cm$^{-1}$.

COMPARATIVE EXAMPLE

It is well known that many hindered amine light stabilizers, especially in the presence of hindered phenol antioxidants, discolor polyolefins they are stabilizing

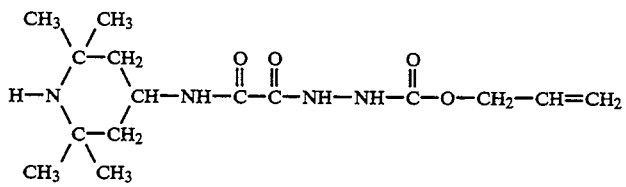

Method A—Preparation of Allyl Carbazate

Allyl phenyl carbonate was prepared in 97% yield by reacting 17.6 grams (0.3 mole) of allyl alcohol with 48.4 grams (0.3 mole) of phenyl chloroformate in the presence of 26.4 grams (0.33 mole) of pyridine and 300 ml of methylene chloride. The allyl phenyl carbonate soluation was washed with 5% HCl, water, dried over anhydrous sodium sulfate, filtered and the methylene chloride evaporated on a rotating evaporator under reduced pressure. The residual allyl phenyl carbonate (52.7 grams—0.29 mole) was dissolved in 200 ml of methanol and treated with 16.0 grams (0.32 mole) of 64% aqueous hydrazine at room temperature. After two hours, gase chromatography indicated that the carbonate had been completely converted to allyl carbazate and phenol. The reaction mixture was stripped of volatiles on the rotating evaporator. The residue was taken up in 200 ml of methylene chloride and washed with 50 grams of 25% sodium hydroxide to remove the phenol. The methylene chloride layer was washed with saturated salt solution, dried over sodium sulfate, filtered and the methylene chloride stripped off on the rotating evaporator. The residue weighed 9.2 grams and assayed 98.0% by gas chromatography. An additional 3.9 grams was recovered by reextracting the aqueous wash.

Method B—Preparation of 1-[N-(2,2,6,6-tetramethyl-4-piperidinyl)oxamoyl]-2-(allyloxycarbonyl)hydrazine Into a 250 ml 3-neck flask was added 9.2 grams (0.079 mole) of allyl carbazate from (A), 34.2 grams (0.08 mole) of a 60% solution of ethyl N-(2,2,6,6-tetramethyl-4-piperidinyl)oxamate and 50 ml of methanol. The flask was equipped with a magnetic stirrer, thermometer and a Dean Stark trap with a reflux The reaction was heated in an oil bath and the methanol was distilled off through the Dean Stark trap. After the methanol distillation ceased, a vacuum was applied to the system to remove any residual methanol and the reaction was cooked for 80 minutes at 90° C. The reaction was cooled to 50° C. and 50 ml of methanol was added and the reaction heated back up to reflux to dissolve the residue. The methanol solution was cooled and concentrated to 25 upon exposure to high temperatures. The following example compares the discoloration of polypropylene tensile bars containing the compounds of U.S. Pat. No. 4,824,884 (assigned to the present assignee) and tensile bars containing equivalent amounts of the compounds of the present invention upon heat aging at various temperatures and time periods. The compounds were compared on the basis of their ability at low concentrations to stabilize polypropylene with reduced discoloration when polypropylene tensile bars containing the indicated stabilizers were exposed to high temperatures.

All of the tensile bars were prepared in accordance with the method described above for Examples LI-XC-VII. The tensile bars were heat aged in a Blue M TM forced air oven at the indicated temperatures and time intervals. The Yellowness Index values were determined on a Colorgard System/05 TM colorimeter manufactured by Pacific Scientific. The tensile bars were prepared and tested both with and without the presence of a secondary antioxidant as indicated in the following tables.

Tables A and B qualitatively demonstrate the discoloration of tensile bars containing the compounds of U.S. Pat. No. 4,824,884 upon heat aging at 140° C. in both the presence and absence of antioxidants.

In order to contrast the compounds of the present invention from those of U.S. Pat. No. 4,824,884, Table C qualitatively demonstrates the comparatively slow buildup of color in tensile bars containing compounds falling within the scope of the present invention upon heat aging at 135° C. for up to 25 days. Similarly, Table D demonstrates the slow increase in color buildup in the tensile bars containing the compounds of the present invention over 50 and 100 day periods at 135° C. The results set forth in Tables C and D indicate that no significant difference in color buildup results whether the sample contains an antioxidant or not.

Tables E and F quantitatively illustrate the difference between the present compounds and those of U.S. Pat. No. 4,824,884 with respect to the change in Yellowness Index ($\Delta$YID) upon heat aging at 120° C. for 1 and 3 days and 140° C. for 3 and 6 days both with and without the concomitant use of secondary antioxidants.

TABLE A

Heat Aging Results at 140° C.
Compounds of U.S. Pat. No. 4,824,884

| Tensile Bar No. | Patent Example No. | Antioxidant | Initial Color | 1 Day | 5 Days | 20 Days |
|---|---|---|---|---|---|---|
| 126 | XII | — | colorless | yellow | brown | dk. brown |
| 127 | XII | 1076[1] | colorless | yllow-brn | dk. brown | dk. brown |
| 128 | XII | 168[2] | colorless | lt. straw | orng-yellow | dk. brown |
| 130 | XI | — | colorless | yellow | brown | dk. brown |
| 131 | XI | 168 | colorless | strw-yllw | brown | dk. brown |
| 132 | XI | 1076/DBHA[3] | colorless | brown | brown | dk. brown |
| 133 | XII | Naugard XL-1[4] | colorless | brown | dk. brown | dk. brown |
| 134 | XII | 1076/DBHA | colorless | brown | dk. brown | dk. brown |
| 138 | VIIA | — | colorless | lt. brown | dk. brown | dk. brown |
| 139 | VIIA | 1076 | colorless | dk. brown | dk. brown | dk. brown |

[1] Irganox ™ 1076 [octadecyl 3-(3,5-di-t-butyl-4-hydroxyphenyl)propionate] is a phenolic antioxidant and was obtained from Ciba-Geigy Corp.
[2] Irgafos ™ 168 [tris(2,4-di-t-butylphenyl)phosphite] is a non-phenolic antioxidant and was obtained from Ciba-Geigy Corp.
[3] N,N-Dibenzylhydroxylamine (DBHA) was purchased from Aldrich Chemical Co.
[4] Naugard ™ XL-1,2,2'-oxamido bis-[ethyl 3-(3,5-di-t-butyl-4-hydroxyphenyl)propionate] is a phenolic antioxidant and was obtained from Uniroyal Chemical Co.

TABLE B

140° C. Heat Aging Tests
Compounds of U.S. Pat. No. 4,824,884
Effect of Antioxidant on Color Upon Heat Aging

| Tensile Bar No. | Patent Example No. of HALS | Antioxidant | Color After 5 Days at 140° C. |
|---|---|---|---|
| 186 | XI | none | dark brown |
| 80 | XI | Irganox 1076 | dark brown |
| 131 | XI | Irgafos 168 | dark brown |
| 132 | XI | Irganox 1076 + DBHA | brown |
| 188 | XI | 0.1% UV-Chek AM-340[5] | dark brown |
| 187 | XI | 0.2% UV-Chek AM 340 | dark brown |
| 189 | XI | 0.2% Cyasorb 2908[6] | dark brown |
| 182 | XII | none | dark brown |
| 127 | XII | Irganox 1076 | dark brown |
| 128 | XII | Irgafos 168 | brown |
| 133 | XII | Naugard XL-1 | brown |
| 134 | XII | Irganox 1076 + DBHA | brown |
| 184 | XII | 0.1% UV-Chek AM-340 | dark brown |
| 183 | XII | 0.2% UV-Chek AM-340 | dark brown |
| 185 | XII | 0.2% Cyasorb 3908 | dark brown |
| 138 | VII-A | none | dark brown |
| 139 | VII-A | Irganox 1076 | dark rown |
| 140 | VII-A | Irganox 1076 + Tridecyl phosphite | dark brown |

[5] UV-Chek ™ AM-340 (2,4-di-t-butylphenyl 3,5-di-t-butyl-4-hydroxybenzoate) was obtained from Ferro Corp.
[6] Cyasorb ™ 2908 (n-hexadecyl 3,5-di-t-butyl-4-hydroxybenzoate) is a phenolic antioxidant and was obtained from the Polymer Additives Department of American Cyanamid Company.

TABLE C

Heat Aging Results at 135° C.
Compounds of Present Invention

| Tensile Bar No. | Application Example No. | Antioxidant | Initial Color | 5 Days | 10 Days | 25 Days |
|---|---|---|---|---|---|---|
| 424 | XLIII | — | colorless | lt. straw | dk. straw | lt. brown |
| 425 | XLIII | 1076 | colorless | yllow-brn | yllow-brn | lt. brown |
| 426 | XLIII | 168 | colorless | lt. straw | staw | lt. tan |
| 432 | XLIV | — | colorless | lt. straw | lt. brown | lt. brown |
| 433 | XLIV | 1076 | v.lt.straw | yllow-brn | lt. brown | lt. brown |
| 434 | XLIV | 168 | colorless | lt. straw | straw | tan |
| 452 | XLV | — | colorless | lt. straw | dk. straw | lt. brown |
| 453 | XLV | 1076 | v.lt.straw | yllow-brn | dk. brown | lt. brown |
| 454 | XLV | 168 | colorless | lt. straw | straw | lt. brown |
| 422 | XXVI | — | colorless | lt. straw | lt. brown | lt. brown |
| 423 | XXVI | 168 | colorless | lt. straw | straw | lt. brown |
| 427 | XXXVII | — | colorless | colorless | lt. straw | off-white |
| 428 | XXXVII | 168 | colorless | colorless | v.lt.straw | off-white |
| 420 | XXXV | — | colorless | colorless | colorless | lt. straw |
| 421 | XXXV | 1076 | colorless | colorless | lt. straw | lt. straw |
| 443 | XXXVI | — | colorless | colorless | colorless | colorless |
| 444 | XXXVI | 1076 | colorless | colorless | v.lt.straw | lt. straw |
| 445 | XXXVI | 168 | colorless | colorless | colorless | colorless |
| 447 | XXXVII | — | colorless | colorless | colorless | colorless |
| 440 | XXXIX | — | colorless | lt. straw | lt. straw | off-white |
| 441 | XXXIX | 1076 | colorless | yllow-brn | yllow-brn | yllow-brn |
| 442 | XXXIX | 168 | colorless | colorless | v.lt.straw | off-white |
| 438 | XL | — | colorless | lt. straw | straw | off-white |
| 439 | XL | 1076 | colorless | yllow-brn | yllow-brn | yllow-brn |
| 435 | XLI | — | colorless | lt. straw | straw | off-white |
| 436 | XLI | 1076 | colorless | yllow-brn | yllow-brn | yllow-brn |
| 437 | XLI | 168 | colorless | v.lt.straw | lt. straw | off-white |
| 429 | XLII | — | colorless | lt. straw | dk. straw | dk. straw |
| 430 | XLII | 1076 | colorless | yllow-brn | yllow-brn | lt. brown |

TABLE C-continued

Heat Aging Results at 135° C.
Compounds of Present Invention

| Tensile Bar No. | Application Example No. | Antioxidant | Initial Color | 5 Days | 10 Days | 25 Days |
|---|---|---|---|---|---|---|
| 431 | XLII | 168 | colorless | lt. straw | straw | off-white |

TABLE D

Heat Aging Results at 135° C.
Compounds of Present Invention

| Tensile Bar No. | Application Example No. | Antioxidant | Initial Color | 50 days | 100 Days |
|---|---|---|---|---|---|
| 420 | XXXV | — | colorless | lt. straw | lt. straw |
| 421 | XXXV | 1076 | colorless | lt. straw | lt. straw |
| 443 | XXXVI | — | colorless | colorless | colorless |
| 444 | XXXVI | 1076 | colorless | lt. straw | lt. straw |
| 445 | XXXVI | 168 | colorless | colorless | colorless |
| 447 | XXXVII | — | colorless | off-white | colorless |
| 440 | XXXIX | — | colorless | lt. straw | — |
| 441 | XXXIX | 1076 | colorless | lt. straw | lt. straw |
| 442 | XXXIX | 168 | colorless | colorless | — |
| 438 | XL | — | colorless | colorless | — |
| 439 | XL | 1076 | colorless | yellow | straw |
| 435 | XLI | — | colorless | lt. straw | — |
| 436 | XLI | 1076 | colorless | yellow | straw |
| 437 | XLI | 168 | colorless | lt. straw | — |
| 429 | XLII | — | colorless | dk. straw | straw |
| 430 | XLII | 1076 | colorless | lt. brown | lt. brown |
| 431 | XLII | 168 | colorless | colorless | — |
| 424 | XLIII | — | colorless | lt. brown | lt. brown |
| 425 | XLIII | 1076 | colorless | lt. brown | lt. brown |
| 426 | XLIII | 168 | colorless | lt. straw | lt. straw |
| 432 | XLIV | — | colorless | lt. brown | dk. brown |
| 433 | XLIV | 1076 | v.lt.straw | lt. brown | lt. brown |
| 434 | XLIV | 168 | colorless | v.lt.brown | dk. straw |
| 452 | XLV | — | colorless | tan | dk. straw |
| 453 | XLV | 1076 | v.lt.straw | lt. brown | dk. straw |
| 454 | XLV | 168 | colorless | lt. brown | dk. straw |
| 422 | XXVI | — | colorless | lt. brown | lt. brown |
| 423 | XXVI | 168 | colorless | lt. brown | lt. straw |
| 427 | XXXVII | — | colorless | lt. straw | lt. straw |
| 428 | XXXVII | 168 | colorless | lt. straw | straw |

TABLE E

Comparative Heat Aging Data at 120° C.

| | Contain no Irganox 1076 | | | Contain Irganox 1076 | | |
|---|---|---|---|---|---|---|
| Example No. | Initial YID | 1 Day ΔYID | 3 Day ΔYID | Initial YID | 1 Day ΔYID | 3 Day ΔYID |
| U.S. Pat. No. 4,824,884 | | | | | | |
| VIIA | 21.6 | 58.7 | 119.3 | 19.6 | 88.0 | 53.4 |
| VIIB | 14.8 | 46.7 | 97.9 | 16.5 | 98.7 | 85.5 |
| XII | 18.1 | 40.7 | 70.4 | 17.9 | 67.5 | 111.8 |
| IB | 15.5 | 16.8 | 45.2 | | | |
| IIIB | 21.2 | 23.3 | 37.2 | | | |
| XI (recrystd) | 15.1 | 28.7 | 65.8 | 28.9 | 34.1 | 87.6 |
| Present Invention | | | | | | |
| XXII | 25.5 | 5.8 | 9.0 | 18.5 | 1.3 | 11.1 |
| XXXIX | 16.4 | 3.1 | 11.8 | 17.6 | 4.2 | 24.2 |
| XL | 15.0 | 0.8 | 14.2 | 16.1 | 7.6 | 32.4 |
| XXXVI | 16.9 | −8.8 | 0.6 | 18.3 | −6.6 | −4.4 |
| XLI | 16.2 | 2.1 | 13.6 | 17.8 | 4.3 | 30.7 |
| XXXVIII | 16.4 | −21.6 | −21.01 | | | |

TABLE F

Comparative Heat Aging Data at 140° C.

| Tensile Bar No. | Compound of | Antioxidant | Initial YID | 3 Day ΔYID | 5 Day ΔYID |
|---|---|---|---|---|---|
| Compounds of U.S. Pat. No. 4,824,884 | | | | | |
| Patent Example | | | | | |
| 182 | XII | none | 18.7 | 44.5 | 79.5 |
| 183 | XII | 0.2% UV Chek | 19.6 | 49.6 | 75.0 |
| 184 | XII | 0.1% UV Chek | 20.3 | 51.8 | 58.7 |
| 185 | XII | 0.2% Cyasorb 2908 | 18.5 | 41.0 | 80.9 |
| 186 | XI | none | 16.3 | 45.7 | 71.1 |
| 187 | XI | 0.2% UV Chek | 17.0 | 51.5 | 47.6 |
| 188 | XI | 0.1% UV Chek | 17.2 | 53.1 | 43.6 |
| 189 | XI | 0.2% Cyasorb 2908 | 17.8 | 49.7 | 59.6 |
| Compounds of the Present Invention | | | | | |
| Application Example | | | | | |

TABLE F-continued

| | Comparative Heat Aging Data at 140° C. | | | | |
|---|---|---|---|---|---|
| Tensile Bar No. | Compound of | Antioxidant | Initial YID | 3 Day ΔYID | 5 Day ΔYID |
| 190 | III | none | 24.8 | 3.2 | 9.7 |
| 191 | III | Irganox 1076 | 27.6 | 2.9 | 17.1 |
| 192 | III | 0.2% UV Chek | 27.2 | −1.2 | 6.4 |
| 198 | XVI | none | 42.0 | −22.1 | −19.1 |
| 199 | XVI | Irganox 1076 | 41.9 | −18.6 | −14.1 |
| 200 | XVI | 0.2% UV Chek | 39.9 | −20.0 | −19.1 |

As can be seen from the results set forth in Tables A–F, the tensile bars containing compounds of the present invention demonstrated significantly less discoloration than those containing the compounds of U.S. Pat. No. 4,824,884. For example, a comparison of the results demonstrated in Tables A–B versus that set forth in Tables C–D, clearly shows that the polypropylene tensile bars containing the present compounds were less discolored after heat aging for periods of up to 100 days. It is noted that the heat aging tests conducted on the tensile bars containing the present compounds (Tables C and D) were conducted at a temperature 5° C. lower than those conducted on the tensile bars containing the comparative compounds (Tables A and B). However, the resulting differences in discoloration were so great that the temperature variation is not significant.

A comparison of the results set forth in Tables E and F clearly shows that the Yellowing Index increased much faster and to a much greater degree in the tensile bars containing the compound of the U.S. Pat. No. 4,824,884 patent than those containing the present compounds, whether antioxidants are present or not.

The present invention may be embodied in other specific forms without departing from the spirit or essential attributes thereof and, accordingly, reference should be made to the appended claims, rather than to the foregoing specification as indicating the scope of the invention.

We claim:

1. A compound having the formula

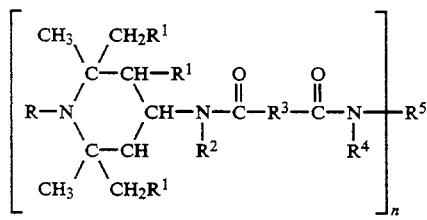

wherein
R is hydrogen, oxyl, hydroxy, substituted or unsubstituted aliphatic of 1–20 carbons, substituted or unsubstituted alicyclic of 5–12 carbons, substituted or unsubstituted araliphatic of 7–22 carbons, substituted or unsubstituted aliphatic acyl of 2–20 carbons, substituted or unsubstituted alicyclic acyl of 7–16 carbons, substituted or unsubstituted aryl acyl of 7–11 carbons, substituted or unsubstituted araliphatic acyl of 8–22 carbons, —C(=O)N(R⁶)(R⁷), —C(=O))ₐO—R⁸, —(CH₂)ₐC(=O)O—R⁹ or —(CH₂—CH(R¹)—O)ᵦ—R¹⁰;
n is 1 or 2;
a is 1 or 2;
b is an integer of 2–50;
R¹ is hydrogen or lower alkyl of 1–4 carbons;

R² is hydrogen, substituted or unsubstituted aliphatic of 1–20 carbons, substituted or unsubstituted alicyclic of 5–12 carbons, substituted or unsubstituted aryl of 6–14 carbons, substituted or unsubstituted araliphatic of 7–22 carbons, 2-cyanoethyl or a radical of the formula

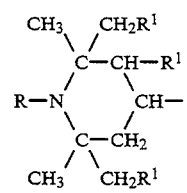

where R and R¹ are as previously defined;
R³ is a direct bond, a substituted or unsubstituted aliphatic diradical of 1–20 carbons, a substituted or unsubstituted aryl diradical of 6–12 carbons, a substituted or unsubstituted alicyclic diradical of 5–12 carbons or a substituted or unsubstituted araliphatic diradical of 7–22 carbons, where the diradical may contain 1–6 —O—, —S— or —NH— heteroatoms with the proviso that multiple heteroatoms must be separated from each other and the diradical ends by at least one carbon atom;
R² and R³ may be linked together to form a 5-membered lactam ring;
R⁴ is hydrogen, substituted or unsubstituted aliphatic of 1–20 carbons, substituted or unsubstituted alicyclic of 5–12 carbons or substituted or unsubstituted araliphatic of 7–22 carbons;
when n is 1, R⁵ is —N=C(R¹¹) (R¹²), —N(R¹³)(R¹⁴) or —N(R⁶)—Q—R¹⁵,
when n is 2, R⁵ is —N(R⁶)—Q—R¹⁷—Q—N(R⁶)—;
Q is —C(=O)—, —C(=O)—O—, —C(=O)—N(R⁴)—, —C(=S)—N(R⁴)— or —S(=O)₂—, in which R⁴ is as previously defined;
R⁶ and R⁷ are independently hydrogen, substituted or unsubstituted aliphatic of 1–20 carbons, substituted or unsubstituted alicyclic of 5–12 carbons, substituted or unsubstituted aryl of 6–14 carbons or substituted or unsubstituted araliphatic of 7–22 carbons;
R⁸ is substituted or unsubstituted aliphatic of 1–20 carbons, substituted or unsubstituted alicyclic of 5–12 carbons, substituted or unsubstituted aryl of 6–14 carbons or substituted or unsubstituted araliphatic of 7–22 carbons;
R⁹ is hydrogen, substituted or unsubstituted aliphatic of 1–20 carbons, substituted or unsubstituted alicyclic of 5–12 carbons, substituted or unsubstituted aryl of 6–14 carbons or substituted or unsubstituted araliphatic of 7–22 carbons;
R¹⁰ is hydrogen or aliphatic of 1–4 carbons;

$R^{11}$ and $R^{12}$ are independently hydrogen, substituted or unsubstituted aliphatic of 1–20 carbons, substituted or unsubstituted alicyclic of 5–12 carbons, substituted or unsubstituted aryl of 6–14 carbons, substituted or unsubstituted araliphatic of 7–22 carbons;

$R^{11}$ and $R^{12}$ may be linked together to form a substituted or unsubstituted alicyclic ring of 5–12 carbons or may be linked together through an —O—, —S— or —NH— heteroatom to form a heterocyclic ring of 5–12 atoms wherein the —NH— may be substituted by lower alkyl of 1–4 carbons;

$R^{13}$ is hydrogen, substituted or unsubstitued aliphatic of 1–20 carbons, substituted or unsubstituted alicyclic of 5–12 carbons, substituted or unsubstituted araliphatic of 7–22 carbons or substituted or unsubstituted aryl of 6–14 carbons, where the $R^{13}$ substituents are chloro, bromo, cyano, hydroxy, epoxy, alkyl of 1–20 carbons, cycloalkyl of 5–12 carbons, aryl of 6–14 carbons, aralkyl of 7–22 carbons, alkoxy of 1–20 carbons, cycloalkoxy of 5–12 carbons, aryloxy of 6–14 carbons, aralkoxy of 7–15 carbons, aliphatic acyloxy of 2–20 carbons, alicyclic acyloxy of 6–13 carbons, aryl acyloxy of 7–15 carbons, alkylthio of 1–12 carbons, trialkoxysilyl of 3–12 carbons or araliphatic acyloxy of 8–16 carbons, wherein any alkyl or cycloalkyl substituent group may contain isolated double bonds;

$R^{14}$ is substituted or unsubstitued aliphatic of 1–20 carbons, substituted or unsubstituted allcyclic of 5–12 carbons, substituted or unsubstituted araliphatic of 7–22 carbons or substituted or unsubstituted aryl of 6–14 carbons, where the $R^{14}$ substituents are chloro, bromo, cyano, hydroxy, epoxy, alkyl of 1–20 carbons, cycloalkyl of 5–12 carbons, aryl of 6–14 carbons, aralkyl of 7–22 carbons, alkoxy of 1–20 carbons, cycloalkoxy of 5–12 carbons, aryloxy of 6–14 carbons, aralkoxy of 7–15 carbons, aliphatic acyloxy of 2–20 carbons, alicyclic acyloxy of 6–13 carbons, aryl acyloxy of 7–15 carbons, alkylthio of 1–12 carbons, trialkoxysilyl of 3–12 carbons or araliphatic acyloxy of 8–16 carbons, wherein any alkyl or cycloalkyl substituent group may contain isolated double bonds;

$R^{15}$ is hydrogen, substituted or unsubstituted aliphatic of 1–20 carbons, substituted or unsubstituted alicyclic of 5–12 carbons, substituted or unsubstituted aryl of 6–14 carbons or substituted or unsubstituted araliphatic of 7–22 carbons;

when Q is —C(=O)—, $R^{15}$ may also be 2-(3,5-dialkyl-4-hydroxyphenyl)ethyl of 13–21 carbons, 3,5-dialkyl-4-hydroxyphenyl of 11–19 carbons in which the alkyl groups are branched or unbranched alkyl of 1–8 carbons, 4-benzoyl-3-hydroxyphenoxymethyl, 2-alkylthioethyl of 3–20 carbons, alkylthiomethyl of 2–20 carbons, 2-(dialkylaminoalkylthio)ethyl of 5–30 carbons or $R^{16}$—N-H—C(=O)—$R^3$—;

when Q is —C(=O)—O—, $R^{15}$ may also be 2,2,6,6-tetramethyl-4-piperidinyl, in which the piperidinyl nitrogen is unsubstituted or substituted with methyl, ethyl, allyl, oxyl, hydroxyl, benzyl, benzoyl or acetyl; 2-(3-hydroxy-4-benzoylphenoxy)ethyl; 2-acryloyloxyethyl; 2-methacryloyloxyethyl; 2-(3-hydroxy-4-benzotriazol-2-ylphenoxy)ethyl; 3-(3-benzotriazol-2-yl-4-hydroxyphenyl)propyl, in which the benzotriazolyl may be substituted in the 5 position with chlorine, methoxy, ethoxy, methoxycarbonyl or ethoxycarbonyl and the phenyl group may be substituted ortho to the hydroxy group with an alkyl group of 1–12 carbons or an aralkyl group of 9–12 carbons; 2-(3,5-dialkyl-4-hydroxyphenyl)ethyl of 13–21 carbons, 3-(3,5-dialkyl-4hydroxyphenyl)propyl of 14–22 carbons or 2-[3-(3,5-dialkyl-4-hydroxyphenyl)propionyloxy]ethyl of 16–24 carbons, in which the alkyl groups are branched or unbranched alkyl of 1–8 carbons; with the proviso that when Q is —(C=O)—O—, $R^{15}$ is not hydrogen;

$R^{16}$ is substituted or unsubstituted aliphatic of 1–20 carbons, substituted or unsubstituted alicyclic of 5–12 carbons, substituted or unsubstituted aryl of 6–14 carbons, substituted or unsubstituted araliphatic of 7–22 carbons, 3,5-dialkyl-4-hydroxyphenyl of 11–19 carbons in which the alkyl groups are independently branched or unbranched alkyl of 1–8 carbons or 2,2,6,6-tetramethyl-4-piperidinyl, in which the nitrogen may be substituted with methyl, ethyl, allyl, oxyl, hydroxyl, benzyl, benzoyl or acetyl; and $R^{17}$ is a substituted or unsubstituted aliphatic diradical of 1–20 carbons, substituted or unsubstituted aryl diradical of 6–12 carbons, substituted or unsubstituted alicyclic diradical of 5–12 carbons or substituted or unsubstituted araliphatic diradical of 7–22 carbons, where the diradicals may contain 1–6 —O—, —S— or —NH— heteroatoms, with the proviso that multiple heteroatoms must be separated from each other and the diradical ends by at least one carbon atom;

substituents for any of R, $R^2$, $R^3$, $R^4$, $R^6$, $R^7$, $R^8$, $R^9$, $R^{11}$, $R^{12}$, $R^{15}$, $R^{16}$ or $R^{17}$ are independently selected from the group consisting of one or more of chloro, bromo, alkyl of 1–8 carbons, alkoxy of 1–8 carbons, phenoxy, cyano, hydroxy, epoxy, carboxy, alkoxycarbonyl of 2–6 carbons, alkanoyloxy of 1–4 carbons, alkanoyl of 1–4 carbons, acryloyl, acryloyloxy, methacryloyl, methacryloyloxy, hydroxymethyl, 2-hydroxyethyl, alkylthio of 1–4 carbons or trialkoxysilyl of 3–12 carbons, with the proviso that when Q is —C(=O)—, $R^{15}$ may not be substituted with a carboxy group; and where R is 2-hydroxy substituted aliphatic or 2-hydroxy substituted allcyclic, substituents for R are also selected from the group consisting of aliphatic of 1–20 carbons, alicyclic of 5–12 carbons, aryl of 6–14 carbons, araliphatic of 7–22 carbons, alkoxy of 1–20 carbons, cycloalkoxy of 5–12 carbons, aryloxy of 6–14 carbons, aralkoxy of 7–15 carbons, aliphatic acyloxy of 2–20 carbons, alicyclic acyloxy of 6–13 carbons, aryl acyloxy of 7–15 carbons or araliphatic acyloxy of 8–16 carbons, where any alkyl or cycloalkyl substituent group of the 2-hydroxy substituted group may contain isolated double bonds.

2. The compound according to claim 1 wherein

R is hydrogen, substituted or unsubstituted alkyl of 1–10 carbons, substituted or unsubstituted alkenyl of 3–8 carbons, substituted or unsubstituted benzyl of 7–9 carbons, 2-cyanoethyl, acetyl, substituted or unsubstituted benzoyl, 2-hydroxyalkyl of 2–10 carbons, 2-hydroxy-3-phenoxypropyl or 2-hydroxy-3-(2-ethylhexoxy)propyl;

$R^1$ is hydrogen or methyl;

$R^2$ is hydrogen, alkyl of 1–4 carbons or 2,2,6,6-tetramethyl-4-piperidinyl;

$R^3$ is a direct bond, an alkylene diradical of 1-8 carbons or an o-, m- or p-phenylene diradical; or $R^2$ and $R^3$ may be linked together to form a 5-membered lactam ring;

$R^4$ is hydrogen;

when n is 1, $R^5$ is —N=C($R^{11}$)($R^{12}$), —N($R^{13}$)($R^{14}$) or —N($R^6$)—Q—$R^{15}$;

Q is —C(=O)—, —C(=O)—O— or —C(=O)—N($R^4$)—;

$R^6$ is hydrogen, substituted or unsubstituted aliphatic of 1-18 carbons, substituted or unsubstituted phenyl or substituted or unsubstituted benzyl;

$R^{11}$ and $R^{12}$ are independently hydrogen, alkyl of 1-8 carbons, cycloalkyl of 5-8 carbons, substituted or unsubstituted aryl of 6-12 carbons, where the substituents are one or more of hydroxy or lower alkyl of 1-4 carbons or $R^{11}$ and $R^{12}$ are linked together to form an alicyclic ring of 5-8 carbons or are linked together through a nitrogen atom to form a 2,2,6,6-tetramethyl-4-piperidinyl ring;

$R^{13}$ is hydrogen and $R^{13}$ and $R^{14}$ are independently alkyl of 1-10 carbons, cycloalkyl of 5-8 carbons, aralkyl of 7-9 carbons, phenyl, substituted or unsubstituted 2-hydroxyalkyl of 2-12 carbons or substituted or unsubstituted 2-hydroxycycloalkyl of 5-8 carbons, where the substituents are alkyl of 1-8 carbons, cycloalkyl of 5-8 carbons, aryl of 6-10 carbons, alkoxy of 1-8 carbons, aryloxy of 6-14 carbons, aliphatic acyloxy of 2-8 carbons, cycloaliphatic acyloxy of 6-9 carbons, aromatic acyloxy of 7-10 carbons or araliphatic acyloxy of 8-10 carbons;

$R^{15}$ is aliphatic of 1-18 carbons, aryl of 6-12 carbons, araliphatic of 7-18 carbons or alicyclic of 6-8 carbons;

when Q is —C(=O)—, $R^{15}$ is also 3,5-di-t-alkyl-4-hydroxyphenyl of 14-18 carbons, 2-(3,5-di-t-alkyl-4-hydroxyphenyl)ethyl of 16-20 carbons, 4-benzoyl-3-hydroxyphenoxymethyl, 2-alkylthioethyl of 8-20 carbons or $R^{16}$—NH—C(=O)—$R^3$—, where $R^3$ is a direct bond or a 1,2-ethylene diradical;

when Q is —C(=O)—O—, $R^{15}$ is also 2,2,6,6-tetramethyl-4-piperidinyl in which the piperidinyl nitrogen is unsubstituted or substituted with methyl, benzoyl or acetyl; 2-(3-hydroxy-4-benzoylphenoxy)ethyl; 2-(3,5-di-t-butyl-4-hydroxyphenyl)ethyl; 3-(3,5-di-t-butyl-4-hydroxyphenyl)propyl; 2-(3-hydroxy-4-benzotriazol-2-ylphenoxy)ethyl; 2-acryloyloxyethyl or 2-methacryloyloxyethyl;

$R^{16}$ is hydrogen, alkyl of 1-12 carbons, aryl of 6-10 carbons, 3,5-di-t-alkyl-4-hydroxyphenyl of 14-18 carbons or 2,2,6,6-tetramethyl-4-piperidinyl which may be substituted on the piperidinyl nitrogen with methyl or acetyl; and when n is 2, $R^5$ is —N($R^6$)—Q—$R^{17}$—Q—N($R^6$)—, where Q is —C(=O)—, —C(=O)—O— or —C(=O)—N($R^4$)—; and $R^{17}$ is an aliphatic diradical of 2-12 carbons, a cycloalkylene diradical of 5-12 carbons, an alicyclic diradical of 7-12 carbons, an aryl diradical of 6-12 carbons, an aralkylene diradical of 7-12 carbons.

3. The compound according to claim 2 where
R is hydrogen, methyl, acetyl or benzoyl;
$R^1$ and $R^2$ are hydrogen;
$R^3$ is a direct bond or an alkylene diradical of 1-7 carbons;
$R^4$ is hydrogen;

when n is 1, $R^5$ is —N=C($R^{11}$)($R^{12}$), —N($R^{13}$)($R^{14}$) or —N($R^6$)—Q—$R^{15}$;

Q is —C(=O)—, —C(=O)—O— or —C(=O)—NH—;

$R^6$ is hydrogen, methyl or ethyl;

$R^{11}$ and $R^{12}$ are independently lower alkyl of 1-4 carbons or $R^{11}$ and $R^{12}$ are linked together to form a cyclopentyl, cyclohexyl or cyclooctyl ring or are linked together through a nitrogen atom to form a 2,2,6,6-tetramethyl-4-piperidinyl ring;

$R^{13}$ is hydrogen and $R^{13}$ and $R^{14}$ are independently alkyl of 1-4 carbons, cyclohexyl, benzyl, phenyl, substituted or unsubstituted 2-hydroxyalkyl of 2-10 carbons or substituted or unsubstituted 2-hydroxycyclohexyl where the substituents are alkyl of 1-8 carbons, phenoxy, acetoxy, acryloyloxy, methacryloyloxy or benzoyloxy;

R15 is alkyl of 1-18 carbons, phenyl, 2-hydroxyphenyl or dimethyl-m-isopropenylbenzyl;

when Q is —C(=O)—, $R^{15}$ is also 3,5-di-t-butyl-4-hydroxyphenyl, 2-(3,5-di-t-butyl-4-hydroxyphenyl)ethyl, 4-benzoyl-3-hydroxyphenoxymethyl, undecyl, heptadecyl or $R^{16}$—NH—C(=O)—$R^3$—;

when Q is —C(=O)—O—, $R^{15}$ is also allyl, methallyl, 2,2,6,6-tetramethyl-4-piperidinyl, 1,2,2,6,6-pentamethyl-4-piperidinyl, or 2-(3-hydroxy-4-benzoylphenoxy)ethyl;

$R^{16}$ is 3,5-di-t-butyl-4-hydroxyphenyl or 2,2,6,6-tetramethyl-4-piperidinyl;

when n is 2, $R^5$ is —NH—Q—$R^{17}$—Q—NH—, where Q is —C(=O)— or —C(=O)—NH—; and $R^{17}$ is an alkylene diradical of 2-10 carbons or an o-, m- or p-phenylene diradical which may be substituted with methyl, cycloalkylene of 9-10 carbons or aralkylene of 8-12 carbons.

4. The compound according to claim 3 where n is 1, R and $R^4$ are hydrogen, $R^3$ is a direct bond or a 1,2-ethylene diradical, $R^5$ is —NH—C(=O)—NH—$R^{15}$ and $R^{15}$ is methyl, ethyl, phenyl, isopropyl, n-butyl, octadecyl or dimethyl-m-isopropenylbenzyl.

5. The compound according to claim 4 where $R^3$ is a direct bond and $R^{15}$ is phenyl, n-butyl, octadecyl or dimethyl-m-isopropenylbenzyl.

6. The compound according to claim 4 where $R^3$ is a 1,2-ethylene diradical and $R^{15}$ is n-butyl.

7. The compound according to claim 3 where n is 2, R and $R^4$ are hydrogen, $R^3$ is a direct bond, $R^5$ is —NH—C(=O)—NH—$R^{17}$—C(=O)—NH— and $R^{17}$ is a 1,6-hexamethylene, 2,4-tolylene, 1,4-phenylenebis(1-methylethyl) or 1,3,3-trimethylhexahydrotoluene-alpha,5-diyl diradical.

8. The compound according to claim 3 where n is 1, R and $R^4$ are hydrogen, $R^3$ is a direct bond, $R^5$ is —NH—C(=O)—$R^{15}$ and $R^{15}$ is methyl, ethyl, propyl, isopropyl, butyl, pentyl, hexyl, heptyl, nonyl, undecyl, tridecyl, pentadecyl, heptadecyl, phenyl, 2-hydroxyphenyl, 3,5-di-t-butyl-4-hydroxyphenyl, 2-(3,5-di-t-butyl-4-hydroxyphenyl)ethyl or 4-benzoyl-3-hydroxyphenoxy-methyl.

9. The compound according to claim 3 where n is 1, R and $R^4$ are hydrogen, $R^3$ is a direct bond, $R^5$ is —NH—C(=O)—$R^{15}$ $R^{15}$ is $R^{16}$—NH—C(=O)— and $R^{16}$ is 3,5-di-t-butyl-4-hydroxyphenyl or 2,2,6,6-tetramethyl-4-piperidinyl.

10. The compound according to claim 3 where n is 2, R and $R^4$ are hydrogen, $R^3$ is a direct bond, $R^5$ is —NH—C(=O)—$R^{17}$—C(=O)—NH— and $R^{17}$ is a 1,2- ethylene, 1,4-butylene, 1,3-phenylene or 1,4-phenylene diradical.

11. The compound according to claim 3 where n is 1, R and $R^4$ are hydrogen, $R^3$ is a direct bond, $R^5$ is —N=C($R^{11}$)($R^{12}$), $R^{11}$ and $R^{12}$ are independently lower alkyl of 1–4 carbons or $R^{11}$ and $R^{12}$ are linked together to form a cyclohexyl ring or are linked together through a nitrogen atom to form a 2,2,6,6-tetramethyl-4-piperidinyl ring.

12. The compound according to claim 11 where $R^{11}$ and $R^{12}$ are methyl.

13. The compound according to claim 11 where $R^{11}$ is methyl and $R^{12}$ is ethyl.

14. The compound according to claim 11 where $R^{11}$ and $R^{12}$ are linked together to form a cyclohexyl ring.

15. The compound according to claim 11 where $R^{11}$ and $R^{12}$ are linked together through a nitrogen atom to form a 2,2,6,6-tetramethyl-4-piperidinyl ring.

16. The compound according to claim 2 where n is 1, R, $R^1$, $R^2$ and $R^4$ are hydrogen $R^3$ is a direct bond, $R^5$ is —N=C($R^{11}$)($R^{12}$), $R^{11}$ is hydrogen and $R^{12}$ is 3,5-di-t-butyl-4-hydroxyphenyl.

17. The compound according to claim 1 where n is 1, R, $R^1$, $R^2$ and $R^4$ are hydrogen $R^3$ is a direct bond and $R^5$ is —NH—S(=O)$_2$—C$_6$H$_5$.

18. The compound according to claim 1 where n is 1, R, $R^1$, $R^2$ and $R^4$ are hydrogen $R^3$ is a direct bond and $R^5$ is —NH—C(=S)—NH—n—C$_4$H$_9$.

19. The compound according to claim 3 where n is 1, R, $R^1$, $R^2$ and $R^4$ are hydrogen $R^3$ is a direct bond, $R^5$ is —NH—C(=O)—O—$R^{15}$ and $R^{15}$ is methyl, ethyl, propyl, isopropyl, n-butyl, allyl or methallyl.

20. The compound according to claim 3, where R, $R^1$, $R^2$ and $R^4$ are hydrogen, $R^3$ is a direct bond and $R^5$ is —NH—C(=O)—C$_2$H$_5$.

21. The compound according to claim 2 where n is 1, R, $R^1$, $R^2$ and $R^4$ are hydrogen, $R^3$ is a direct bond, $R^5$ is —NH—C(=O)—O—$R^{15}$ and $R^{15}$ is 2,2,6,6-tetramethyl-4-piperidinyl in which the piperidinyl nitrogen is unsubstituted or substituted with methyl, benzoyl or acetyl; 2-(3-hydroxy-4-benzoylphenoxy) ethyl; 2-(3,5-di-t-butyl-4-hydroxyphenyl)ethyl; 3-(3,5-di-t-butyl-4-hydroxyphenyl)propyl; 2-(3-hydroxy-4-benzotriazol-2-ylphenoxy)ethyl; 2-acryloyloxyethyl or 2-methacryloyloxyethyl.

22. The compound according to claim 21 where $R^{15}$ is 2,2,6,6-tetramethyl-4-piperidinyl, 1,2,2,6,6-pentamethyl-4-piperidinyl, or 2-(3-hydroxy-4-benzoylphenoxy)ethyl.

23. The compound according to claim 2 where n is 1, R is hydrogen or 2-hydroxy-3-phenoxypropyl, $R^1$, $R^2$ and $R^4$ are hydrogen $R^3$ is a direct bond, $R^5$ is —N($R^{13}$)($R^{14}$), $R^{13}$ is hydrogen or 2-hydroxy-3-phenoxypropyl or $R^{14}$ is 2-hydroxy-3-phenoxypropyl.

24. The compound according to claim 2 where n is 1, R is hydrogen or 2-hydroxy-3-(2-ethylhexoxy)propyl, $R^1$, $R^2$ and $R^4$ are hydrogen, $R^3$ is a direct bond, $R^5$ is —N($R^{13}$)($R^{14}$), $R^{13}$ is hydrogen or 2-hydroxy-3-(2-ethylhexoxy)propyl and $R^{14}$ is 2-hydroxy-3-(2-ethylhexoxy)propyl.

25. The compound according to claim 8 where $R^{15}$ is 2-(3,5-di-t-butyl-4-hydroxyphenyl)ethyl.

* * * * *